United States Patent [19]

Moehle

[11] Patent Number: 5,871,923
[45] Date of Patent: Feb. 16, 1999

[54] METHODS FOR SCREENING FOR ANTIMYCOTICS

[75] Inventor: Charles M. Moehle, Hayward, Calif.

[73] Assignee: Ribogene, Inc., Hayward, Calif.

[21] Appl. No.: 802,626

[22] Filed: Feb. 19, 1997

Related U.S. Application Data

[60] Division of Ser. No. 328,258, Oct. 24, 1994, Pat. No. 5,641,627, which is a continuation-in-part of Ser. No. 142, 880, Oct. 25, 1993, abandoned.

[51] Int. Cl.$^6$ .................................................. C12Q 1/68
[52] U.S. Cl. ............................................................ 435/6
[58] Field of Search ................................... 435/6, 254.21

[56] References Cited

U.S. PATENT DOCUMENTS 4,792,520  12/1988  Stambrook et al. ........................ 435/6

FOREIGN PATENT DOCUMENTS 9423041  10/1994  WIPO .

OTHER PUBLICATIONS

Leppert et al., *Genetics,* vol. 125, 1990, pp. 13–20.
Balei et al., *J. Biol. Chem.,* vol. 262, 1987, pp. 16871–16879.
Alani et al., "A Method for Gene Disruption That Allows Repeated Use of URA3 Selection in the Construction of Multiply Disrupted Yeast Strains," *Genetics* 116:541–545 (1987).
Balzi and Goffeau, "Multiple or pleiotropic drug resistance in yeast," *Biochem. Biophys. Acta* 1073:241–252 (1991).
Belcourt and Farabough, "Ribosomal Frameshifting in a Yeast Retrotransposon TY: tRNAs Induce Slippage on a 7 Nucleotide Minimal Site," *Cell* 62:339–352 (1990).
Boeke et al., A positive selection for mutants lacking orotidine–5'–phosphate decarboxylase activity in yeast *Saccharomyces cerevisiae*: 5–fluoro–orotic acid resistance,: *Mol. Gen. Genetics* 197:345–346 (1984).
Brugge, "New Intracellular Targets for Therapeutic Drug Design," *Science* 260:918–919 (1993).
Cashel and Rudd, "The Stringent Response, *Escherichia coli* and Salmonella Typhimurium," *Cellular and Molecular Biology,* ed. F.C. Neidhardt (Washington D.C., American Society for Microbiology 1987) 2:1410–1438.
Chien et al., "The two–hybrid system: A method to identify and clone genes for proteins that interact with a protein of interest," *Proc. Natl. Acad. Sci. USA* 88:9578–9582 (1991).
Christianson et al., "Multifunctional yeast high–copy number shuttle vectors," *Gene* 110:119–122 (1992).
Clare and Oliver, "The Regulation of RNA Synthesis in Yeast," *Mol. Gen. Genet.* 188:96–102 (1982).
Clark, "New Approaches for Antifungal Drugs," ed. P.B. Fernandes (Boston:Birkhauser 1992) pp. 1–19.
Colthurst et al., "Elongation factor 3 (EF–3) from *Candida albicans* show both structural and functional similarity to EF–3 from *Saccharomyces cerevisiae,"* *Molecular Microbiology* 6:1025–1033 (1992).

Colthurst et al., "Candida Albicans and three other Candida species contain an elongation factor structurally and functionally analogous to elongation factor 3," *FEMS Microbiology Letters* 80:45–50 (1991).
Dancis et al., Ferric reductase of *Saccharomyces cervisiae*: Molecular characterization, role in iron uptake, and transcriptional control, *Proc. Natl. Acad. Sci. USA* 89:3869–3873 (1992).
Dever et al., "Phosphorylation of Initiation Factor 2α by Protein Kinase GCN2 Mediates Gene–Specific Translational Control of GCN4 in Yeast," *Cell* 68:585–596 (1992).
Eberhart et al., "Species Differences in the Toxicity and Cytochrome P450 IIIA–Dependent Metabolism of Digitoxin," *Mol. Pharmacol.* 40:859–867 (1991).
Erickson and Johnston, "Direct Cloning of Yeast Genes from an Ordered Set of Lambda Clones in *Saccharomyces cerevisiae* by Recombination in vivo," *Genetics* 134:151–157 (1993).
Ezekial and Elkins, The Stimulation of Ribonucleic Acid Synthesis by Ribosome Inhibitors in Amino Acid–Starved *Escherichia coli, Biochem. Biophys. Acta* 166:466–474 (1968).
The Federal Register 47 (No. 56): 12558–12564 (1982).
Fields and Song, "A novel genetic system to detect protein–protein interactions," *Nature* 340:245–246 (1989).
Firoozan et al., "Quantitation of Readthrough of Termination Codons in Yeast using a Novel Gene Fusion Assay," *Yeast* 7:173–183 (1991).
Graybill, "New Antifungal Agents," *Eur. J. Clin. Microbiol. Infect. Dis.* 8:402–412 (1989).
Gross and Pogo, "Control of Ribonucleic Acid Synthesis in Eukaryotes 3. The Effect of Cycloheximide and Edeine on RNA Synthesis in Yeast," *Biochemistry* 15:2082–2086 (1976).
Hershey, "Translation Control in Mammalian Cells," C.C. Richardson ed., *Ann. Rev. of Biochem.* (Annual Review, Inc. 1991) 60:717–755.
Higgins et al., "Turnover of mRNA in prokaryotes and lower eukaryotes," *Curr. Opin. in Gen. and Dev.* 2:739–747 (1992).
Hinnebusch and Liebman, "Protein Synthesis and Translational Control in *Saccharomyces cerevisiae,"* *The Molecular Biology of the Yeast Saccharomyces,* eds. J.R. Broach, J.R. Pringle and E.W. Jones (New York: CSH Laboratory Press, 1991) pp. 627–735.
Hinnenbush et al., "A synthetic HIS4 regulatory element confers general amino acid control on the cytochrome c gene (2CYC1) of yeast," *Proc. Natl. Acad. Sci. USA* 82:498–502 (1985).
Huston and Logan, "Detoxification of the organophosphorus insecticide chlorfenvinphos by rat, rabbit and human liver enzymes," *Xenobiotica* 16:87–93 (1986).

(List continued on next page.)

*Primary Examiner*—James Ketter
*Attorney, Agent, or Firm*—Pennie & Edmonds LLP

[57] ABSTRACT

Screening methods for identification of antimy-cotic agents active in mycotic cell translation, the agents identified thereby, and uses of these agents.

72 Claims, 8 Drawing Sheets

OTHER PUBLICATIONS

Hwang et al., "Construction of a Promoter–Probe Vector with the PH05 Gene Encoding Repressible Acid Phosphate in *Saccharomyces cerevisiae*," *Appl. Microbiol. Biotechnol.* 28:155–159 (1988).

Hwang et al., "The Identification of a Domain in *Escherichia coli* Elongation Factor Tu That Interacts with Elongation Factor Ts," *J. Biol. Chem.* 267–22198–22205 (1992).

Hwang et al., "Mutagenesis of Bacterial Elongation Factor Tu at Lysine 136," *J. Biol. Chem.* 264:8304–8309 (1989).

Koltin, "Targets for Antifungal Drug Discovery," *Annual Reports in Medicinal Chemistry,* ed. James A. Bristol, Harcourt Brace Jovanovich, San Diego, Academic Press, Inc., 25:141–148 (1989).

Lanker et al., "Autoregulation of the Yeast Lysyl–tRNA Synthetase Gene Gcd5/KRS1 by Translation and Transcriptional Control Mechanisms," *Cell* 70:647–657 (1992).

Leeds et al., "Gene Products That Promote mRNA Turnover in *Saccharomyces cerevisiae*," *Mol. Cell. Biol.* 12:2615–2177 (1992).

Lindahl and Hinnebusch, "Diversity of mechanisms in the regulation of translation in prokaryotes and lower eukaryotes," *Curr. Opin. in Gen. and Dev.* 2:720–726 (1992).

Merrick, "Mechanism and Regulation of Eukaryotic Protein Synthesis," *Microbiological Reviews* 56:291–315 (1992).

Min and Zassenhaus, "Identification of a Protein Complex That Binds to a Dodecamer Sequence Found at the 3' Ends of Yeast Mitochondrial mRNAs," *Mol. Cell. Biol.* 13:4167–4173 (1993).

Miranda et al., "Falvin–Containing Monooygenase: A Major Detoxifying Enzyme for the Pyrrolizidine Alkaloid Senecionine in guinea Pig Tissues," *Biochem. Biophys. Res. Commun.* 178:546–552 (1991).

Moehele and Hinnebusch, "Association of RAP1 Binding Sites With Stringent Control of Ribosomal Protein Gene Transcription in *Saccharomyces cerevisiae*," *Mol. Cell. Biol.* 11:2723–2735 (1991).

Nieuwint et al., "Mutational analysis of the upstream activation site of yeast ribosomal protein genes," *Cell* 71:97–105 (1992).

Nelson et al., "The Translation Machinery and 70 kd Heat Shock Protein Cooperate in Protein Synthesis," *Current Genetics* 15:247–251 (1989).

Oliver and McLaughlin, "The Regulation of RNA Synthesis in Yeast 1: Starvation Experiments," *Mol. Gen. Genetics* 154:145–153 (1977).

Paull et al., "The Synthesis of XTT: A New Tetrazolium Reagent that is Bioreducible to a Water–Soluble Formazan," *J. Heterocyclic Chem.* 25:911–914 (1988).

Pon and Schatz, "Biogenesis of Yeast Mitochondria," *The Molecular Biology of the Yeast Saccharomyces,* eds. J.R. Broach, J.R. Pringle, and E.W. Jones (New York: CSH Laboratory Press 1991) pp. 333–406.

Qin et al., "Sequence Analysis of the Translational Elongation Factor 3 From *Saccharomyces cerevisiae*," *J. Biol. Chem.* 265:1903–1912 (1990).

Rameriz et al., "Mutations Activating the Yeast eIF–2α Kinase GCN2: Isolation of Alleles Altering the Domain Related to Histidyl–tRNA Synthetases," *Mol. Cell. Biol.* 12:5801–5815 (1992).

Ray and Butow, "Regulation of Mitochondrial Ribosomal RNA Synthesis in Yeast," *Mol. Gen. Genet.* 173:227–238 (1979).

Sandbaken et al., "Protein Synthesis in Yeast. Structural and functional analysis of the gene encoding elongation factor 3," *J. Biol. Chem.* 200:15838–15844 (1990).

Sandbaken et al., "Isolation and characterization of the structural gene encoding elongation factor 3," *Biochem. Biophys. Acta* 1050:230–234 (1990).

Siegel, "Effect of Fungicides on Protein Synthesis," *Antifungal Compounds,* sr. ed. Hugh D. Sister (New York, Marcel Dekker, Inc. 1977) vol. 2:399–348.

Sikorski and Hieter, "A System of Shuttle Vectors and Yeast Host Strains Designed for Efficient Manipulation of DNA in *Saccharomyces cerevisiae*," *Genetics* 122:19–27 (1989).

Silver and Bostian, "Screening of Natural Products for Antimicrobial Agents," *Euro. J. Clin. Microbiolog. Infect. Dis.* 9:455–461 (1990).

Stateva and Venkov, "Genetic Analysis of *Saccharomyces cerevisiae* SY 15 relaxed mutant," *Mol. Gen. Genet.* 195:234–237 (1984).

Tuite and Plesset, "mRNA–Dependent Yeast Cell–Free Translation Systems: Theory and Practice," *Yeast* 2:35–52 (1986).

Tuite, "Antifungal drug development: the identification of new targets," *Trends in Biotechnology,* 10:235–239 (1992).

Vignais and Sentenac, "Asymmetric DNA Bending Induced by the Yeast Multifunctional Factor TUF," *J. Biol. Chem.* 264:8463–8466 (1989).

Vignais et al., "Contacts between the Factor TUF and RPG Sequences," *J. Biol. Chem.* 265:14669–14674 (1990).

Waltschewa et al., "Relaxed Mutant of *Saccharomyces cerevisiae*: Proper Maturation of Ribosomal RNA in Absence of Protein Synthesis," *Cell* 33:221–230 (1983).

Warner and Gorenstein, "Yeast has a true stringent response," *Nature* 275:338–339 (1978).

Waxman et al., "Gene–Specific Oligonucleotide Probes for α, μ, η and Microsomal Rat Glutathione–S–Transferases: Analysis of Liver Transferase Expression and Its Modulation by Hepatic Enzyme Inducers and Platinum Anticancer Drugs," *Cancer Res.* 52:5797–5802 (1992).

Weislow et al., "New Soluble–Formazan Assay for HIV–1 Cytopathic Effects: Application to High–Flux Screening of Synthetic and natural Products for AIDS–Antiviral Activity," *J. Canc. Inst.* 81:577–586 (1989).

Wek et al., "Truncated Protein Phosphatase GLC7 Restores Translational Activation of GCN4 Expression in Yeast Mutants Defective for the eIF–2α Kinase GCN2," *Mol. Cell. Biol.* 12:5700–5710 (1992).

Widner and Wickner, "Evidence that the SKI Antiviral System that *Saccharomyces cerevisiae* Acts by Blocking Expression of Viral mRNA," *Mol. Cell. Biol.* 13:4331–4341 (1993).

Yang et al., "A Protein Kinase Substrate Identified by the Two–Hybrid System," *Science* 257:680–682 (1991).

Yoshida et al., "Function of the PHO regulatory genes for repressible acid phosphatase synthesis in *Saccharomyces cerevisiae*," *Mol Gen Genet* 217:40–46 (1989).

Zhong and Arndt, "The Yeast SIS 1 Protein, a DnaJ Homolog, is Required for the Initiation of Translation," *Cell* 73:1175–1186 (1993).

Paluh et al., 1988, "The cross–pathway control gene of *Neurospora crassa,* cpc–1, encodes a protein similar to GCN4 of yeast and DNA–binding domain of the oncogene v–jun–encoded protein, "*Proc. Natl. Acad. Sci. U.S.A.* 85:3728–3732.

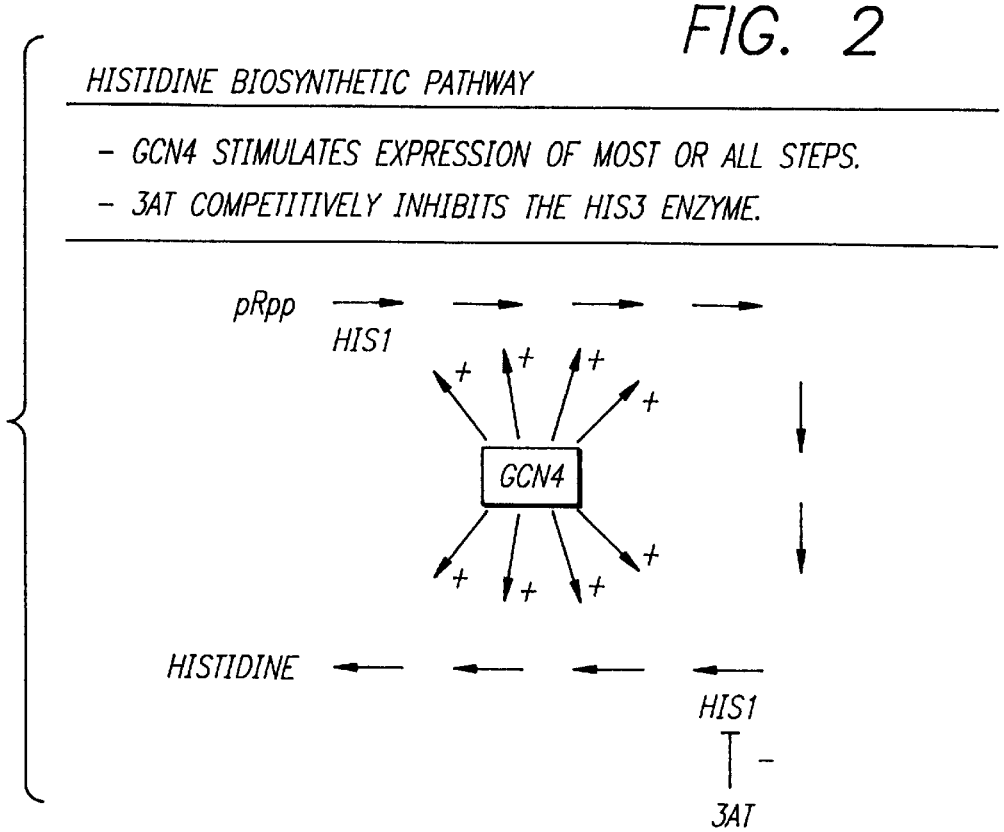

FIG. 2

HISTIDINE BIOSYNTHETIC PATHWAY
- GCN4 STIMULATES EXPRESSION OF MOST OR ALL STEPS.
- 3AT COMPETITIVELY INHIBITS THE HIS3 ENZYME.

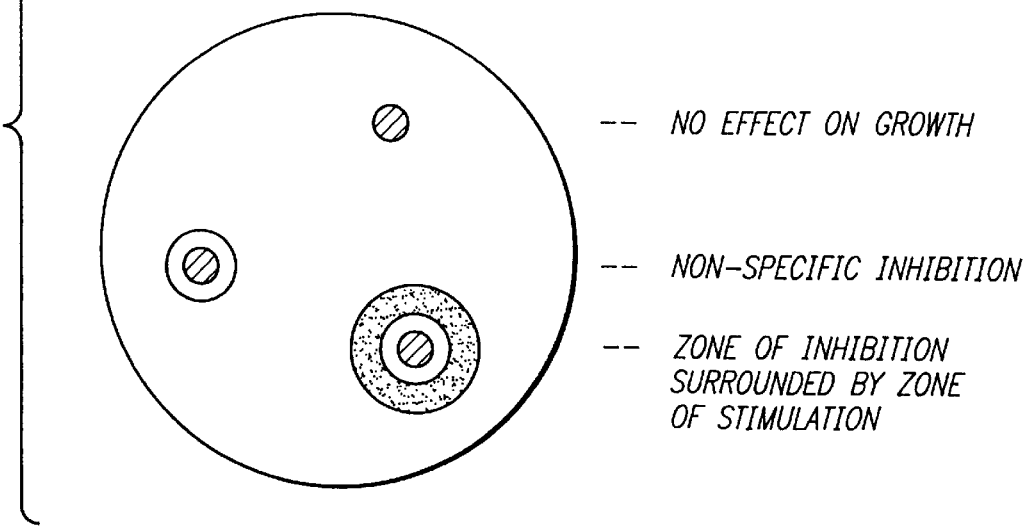

FIG. 3

PARADOXICAL GROWTH ASSAY
- CELLS ARE PLATED ON MEDIUM THAT ALLOWS VERY LITTLE GROWTH.
- AT A SUB-LETHAL CONCENTRATION, A TRANSLATION BLOCKER STIMULATES EXPRESSION OF A GENE NEEDED FOR GROWTH.

-- NO EFFECT ON GROWTH

-- NON-SPECIFIC INHIBITION

-- ZONE OF INHIBITION SURROUNDED BY ZONE OF STIMULATION

FIG. 4

STRINGENT CONTROL AS A MONITOR OF TRANSLATIONAL STATUS

- TRANSLATING RIBOSOMES WITH "HUNGRY CODONS" GENERATE STARVATION SIGNAL WHICH REPRESSES RPL16A EXPRESSION.
- INHIBITORS OF ELONGATION BLOCK STARVATION SIGNAL.
- RPL16A EXPRESSION IS MONITORED WITH GENE FUSIONS.

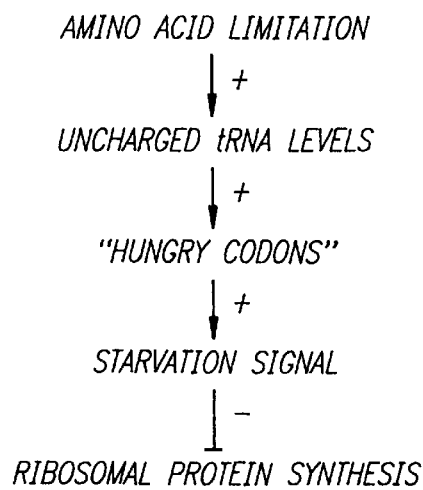

AMINO ACID LIMITATION
↓ +
UNCHARGED tRNA LEVELS
↓ +
"HUNGRY CODONS"
↓ +
STARVATION SIGNAL
↓ −
RIBOSOMAL PROTEIN SYNTHESIS

FIG. 5

TERMINATION SUPPRESSION ASSAY

- PICK A GENE ENCODING A USEFUL REPORTER, E.G., PHO5.
- INTRODUCE A TERMINATION CODON NEAR 5' END OF THE ORF.
- SCREEN FOR COMPOUNDS THAT RESTORE ENZYME ACTIVITY.

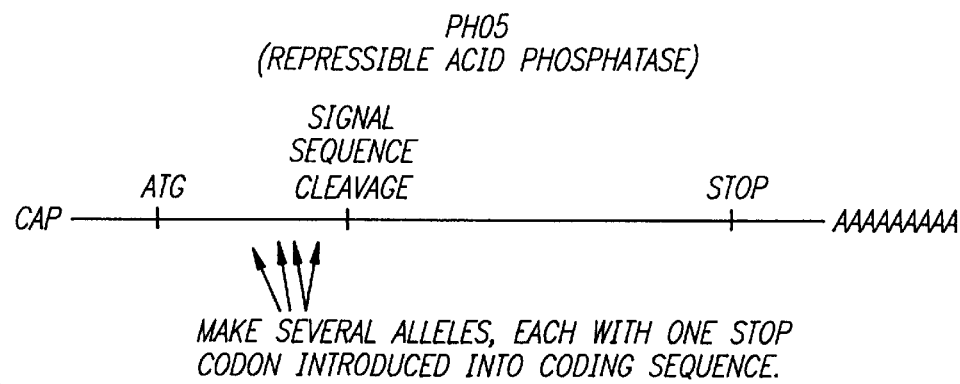

PHO5
(REPRESSIBLE ACID PHOSPHATASE)

CAP —— ATG —— SIGNAL SEQUENCE CLEAVAGE —— STOP —— AAAAAAAA

MAKE SEVERAL ALLELES, EACH WITH ONE STOP CODON INTRODUCED INTO CODING SEQUENCE.

FIG. 6A

A. PHENOTYPIC RELAXATION ASSAY RESULTS WITH KNOWN TRANSLATION BLOCKERS

- DESIRED COMPOUNDS STIMULATE GROWTH OF RPL16A-HIS3 STRAIN IN THE PRESENCE OF MIC OF 3AT.
- SOME COMPOUNDS ARE TOXIC TO GROWTH OF CELLS ON NON-STARVATION CONDITIONS.

|  |  | FUNGITOXIC | |
|---|---|---|---|
|  |  | YES | NO |
| GROWTH ON 3AT | YES | ANISOMYCIN<br>CYCLOHEXIMIDE<br>G418<br>HYGROMYCIN B<br>T-2 TOXIN | EMETINE    KANAMYCIN B<br>GENTAMYCIN    PUROMYCIN<br>GOUGEROTIN |
| | NO | | CLORAMPHENICOL    RIBOSTAMYCIN<br>CHLORTETRACYCLINE    SPECTINOMYCIN<br>diOHstrep.    STREPTOMYCIN<br>ERYTHROMYCIN    TETRACYCLINE<br>FUSIDIC ACID    THIOSTREPTON<br>LINCOMYCIN    TYLOSIN TARTRATE<br>PAROMOMYCIN    VIOMYCIN |

FIG. 6B

B. PHENOTYPIC RELAXATION ASSAY RESULTS WITH NON-TRANSLATION BLOCKERS

- FALSE POSITIVES STIMULATE GROWTH OF RPL16A-HIS3 STRAIN IN THE PRESENCE OF MIC OF 3AT
- SOME COMPOUNDS ARE TOXIC TO GROWTH OF CELLS ON NON-STARVATION CONDITIONS.

|  |  | FUNGITOXIC | |
|---|---|---|---|
|  |  | YES | NO |
| GROWTH ON 3AT | YES | CACODYLIC ACID<br>HCL, CONC.<br>NaOH, 10 N<br>NYSTATIN<br>4 OTHERS | AMMONIUM PERSULFATE<br>GUANIDINE THIOCYANATE<br>KOH, 1 M<br>NaAc, 3 M pH 8.3 |
| | NO | CANAVANINE<br>EDTA, 0.5 M<br>HAc, GLACIAL<br>NYSTATIN<br>4 OTHERS | HAc, 1 M    TE, pH 8.0<br>HCl, 1 M    TRIS, 1 M<br>PBS, 10X    TRITON X-100<br>NaPO4, 0.2 M pH 9.3    TWEEN 20<br>PABA    24 OTHERS |

FIG. 8

*TRANSLATION-COMPONENT-SPECIFIC ASSAY*

- *ISOGENIC YEAST STRAINS. EACH ONE EITHER OVER- OR UNDER-EXPRESSES A SINGLE TRANSLATION COMPONENT.*
- *TEST STRAINS FOR GROWTH IN PRESENCE OF INHIBITORS.*
- *COMPOUND INTERACTING WITH A SPECIFIC TRANSLATION STEP IS MORE POTENT AGAINST SPECIFIC MUTANT(S).*

NO INHIBITOR.
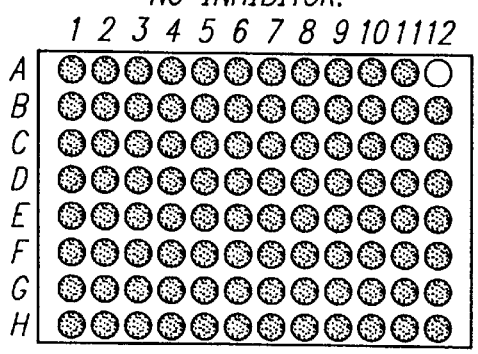

INHIBITOR 1.
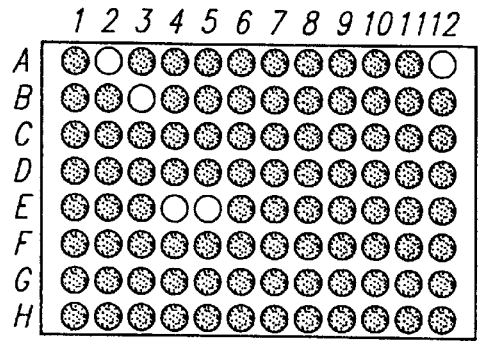

NON-SPECIFIC INHIBITOR
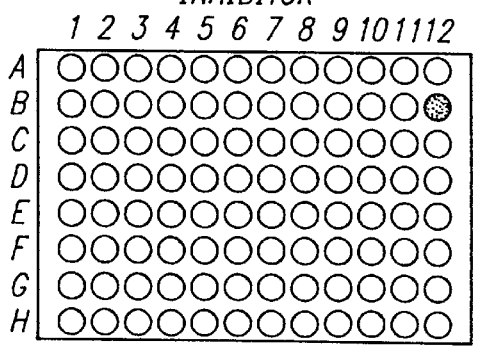

INHIBITOR 2.
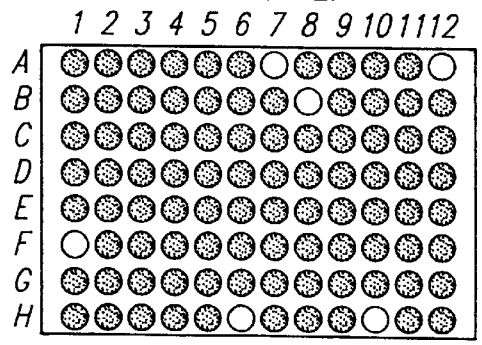

● — GROWTH
○ — NO GROWTH

METHODS FOR SCREENING FOR ANTIMYCOTICS

RELATED APPLICATION

This is a division, of application Ser. No. 08/328,258, filed Oct. 24, 1994, now U.S. Pat. No. 5,641,627, which is a continuation-in-part of Moehle, U.S. patent application Ser. No. 08/142,880, filed Oct. 25, 1993, now abandoned, entitled "Methods for Screening for Antimycotics," the whole of which is hereby incorporated by reference.

This invention relates to methods for screening for agents useful for treatment of mycoses, fungal infections or infestations, the novel agents identified using such screening methods, and their use as antifungal or antimycotic agents.

BACKGROUND OF THE INVENTION

Fungal and other mycotic pathogens (some of which are described in *Human Mycoses*, E. S. Beneke, Upjohn Co.:Kalamazoo, Mich., 1979; *Opportunistic Mycoses of Man and Other Animals*, J. M. B. Smith, CAB International:Wallingford, UK, 1989; and *Scrip's Antifungal Report*, by PJB Publications Ltd, 1992) are responsible for a variety of diseases in humans, animals, and plants ranging from mycoses involving skin, hair, or mucous membranes, such as, but not limited to, Aspergillosis, *Black piedra*, Candidiasis, Chromomycosis, Cryptococcosis, Onychomycosis, or *Otitis externa* (otomycosis), Phaeohyphomycosis, Phycomycosis, *Pityriasis versicolor*, ringworm, *Tinea barbae, Tinea capitis, Tinea corporis, Tinea cruris, Tinea favosa, Tinea imbricata, Tinea manuum, Tinea nigra* (palmaris), *Tinea pedis, Tinea unguium*, Torulopsosis, *Trichomycosis axillaris, White piedra*, and their synonyms, to severe systemic or opportunistic infections, such as, but not limited to, Actinomycosis, Aspergillosis, Candidiasis, Chromomycosis, Coccidioidomycosis, Cryptococcosis, Entomophthoramycosis, Geotrichosis, Histoplasmosis, Mucormycosis, Mycetoma, Nocardiosis, North American Blastomycosis, Paracoccidioidomycosis, Phaeohyphomycosis, Phycomycosis, pneumocystic pneumonia, Pythiosis, Sporotrichosis, and Torulopsosis, and their synonyms, some of which may be fatal. Known fungal and mycotic pathogens include, but are not limited to, *Absidia spp., Actinomadura madurae, Actinomyces spp., Allescheria boydii, Alternaria spp., Anthopsis deltoidea, Apophysomyces eleqans, Arnium leoporinum, Aspergillus spp., Aureobasidium pullulans, Basidiobolus ranarum, Bipolaris spp., Blastomyces dermatitidis, Candida spp., Cephalosporium spp., Chaetoconidium spp., Chaetomium spp., Cladosporium spp., Coccidioides immitis, Conidiobolus spp., Corynebacterium tenuis, Cryptococcus spp., Cunninghamella bertholletiae, Curvularia spp., Dactylaria spp., Epidermophyton spp., Epidermophyton floccosum, Exserophilum spp., Exophiala spp., Fonsecaea spp., Fusarium spp., Geotrichum spp., Helminthosporium spp., Histoplasma spp., Lecythophora spp., Madurella spp., Malassezia furfur, Microsporum spp., Mucor spp., Mycocentrospora acerina, Nocardia spp., Paracoccidioides brasiliensis, Penicillium spp., Phaeosclera dematioides, Phaeoannellomyces spp., Phialemonium obovatum, Phialophora spp., Phoma spp., Piedraia hortai, Pneumocystis carinii, Pythium insidiosum, Rhinocladiella aquaspersa, Rhizomucor pusillus, Rhizopus spp., Saksenaea vasiformis, Sarcinomyces phaeomuriformis, Sporothrix schenckii, Syncephalastrum racemosum, Taeniolella boppii, Torulopsosis spp., Trichophyton spp., Trichosporon spp., Ulocladium chartarum, Wangiella dermatitidis, Xylohypha spp.*, and their synonyms. Other fungi that "obviously have pathogenic potential" (Smith, op. ct.) include, but are not limited to, *Thermomucor indicae-seudaticae, Radiomyces spp.*, and other species of known pathogenic genera. There are also reports implicating Saccharomyces as a human pathogen (e.q., Fungemia with Saccharomycetacea, H. Nielson, J. Stenderup, & B. Bruun, Scand. J. Infect. Dis. 22:581–584, 1990). In recent years there has been a marked increase in the number of serious mycoses as a result of the growing number of immunosuppressed and immunocompromised individuals, such as transplant recipients, patients receiving chemotherapy, and HIV-infected individuals.

Fungal infection is also a significant problem in veterinary medicine including, but not limited to, candidiasis, cryptococcosis, aspergillosis, mucormycosis, pythiosis, entomophthoramycosis, oomycosis, chromomycosis, torulopsosis, infections with *Penicillium spp., Trichosporon spp., Paecilomyces spp., Microsporum spp.*, and a variety of miscellaneous/rarer opportunistic mycoses (Opportunistic Mycoses of Man and Other Animals, J. M. B. Smith, CAB International, Wallingford, UK, 1989). Fungal infections are a common cause of nasal disease in dogs and cats (Fungal Diseases of the Nasal Cavity of the Dog and Cat, Wolf, A. M., 1992, Vet. Clin. of North Amer.:Small Anim. Prac. 22, 1119–1132). A variety of fungi, including, but not limited to, *Aspergillus spp., Candida spp., Paecilomyces spp., Penicillium spp., Alternaria spp., Geotrichum spp.*, and *Cladosporium spp.*, have been isolated from animal eyes and may cause fungal keratitis in several species including, but not limited to, horses, dogs, and cats (Microbiology of the Canine and Feline Eye, P.A. Gerding and I. Kakoma, 1990, Vet. Clin. of North Amer.:Small Anim. Prac. 20, 615–625). Skin infections by fungi, including, but not limited to, *Microsporum canis, Trichophyton mentagrophytes, Trichophyton verucosum, Microsporum eguinum, Microsporum gallinae*, and *Microsporum nanum*, occur in many different animals, ,both wild and domestic with some infections being specific to a given host species (Fungal Skin Infections Associated with Animal Contact, W. H. Radentz, 1991, AFP 43, 1253–1256).

Some of the fungi that infect animals can be transmitted from animals to humans. Fungal zoonotic diseases are most commonly associated with animals used as pets, with a higher frequency found among veterinary personnel owing to higher levels of contact with animals (ibid., M. R. Lappin, Vet. Clin. of North Amer. :Small Anim. Prac. 23, 57–78.). Topical and systemic antifungal agents are used to treat both humans and animals.

Fungal infections or infestations are also a very serious problem in agriculture with fungicides being employed to protect vegetable, fruit, and nut crops (F. L. McEwen and G. R. Stephenson, 1979, The Use and Significance of Pesticides in the Environment. Wiley, N.Y.). Fungicides are applied to soil, seeds, propagating material, growing plants, and produce to combat pathogens. Seed and soilborne pathogens include but are not limited to *Aphanomyces spp., Armillaria spp., Cephalosporium spp., Cylindrocladium spp., Fusarium spp., Helminthosporium spp., Macrophomina spp., Magnaporthe spp., Ophiobolus spp., Phymatotrichum spp., Phytophthora spp., Pythium spp., Rhizoctonia spp., Scerotium spp., Sclerotinia spp., Thielaviopsis spp., Ustilago spp., Verticillium spp.*, and *Whetxelinia spp.*, (R. Rodriguez-Kabana, P. A. Backman, and E. A. Curl, Control of Seed and Soil-Borne Plant Diseases. In Antifungal Compounds, M. Siegel and H. Sisler, eds., Marcel Dekker Inc., N.Y., 1977). Post-harvest diseases of fresh fruits and vegetable are caused by fungi including, but not limited to, *Alternaria spp.,*

*Botrytis spp., Centrospora spp., Ceratocystis spp., Colletotrichum spp, Cryptoporiopsis spp., Diplodia spp., Fusarium spp., Helminthosporium spp. Monilinia spp., Nectria spp., Oospora spp., Penicillium spp., Phlyctaena spp., Phoma spp., Phomopsis spp., Rhizopus spp., Sclerotinia spp.,* and *Verticillium spp.*

It has been estimated that fungicides are employed in the growing of one-half of the world's crops (G.

Ordish and J. F. Mitchell. 1967, World Fungicide Usage. In Fungicides, an Advanced Treatise, Vol. 1, pp.39–62. D.C. Torgeson, ed. Academic Press, N.Y.) either to control disease during crop development, to improve the storage of produce, or to increase production of a particular crop. Approximately 20% of U.S. non-pasture crop land is treated with fungicides (E. W. Palm, Estimated Crop Losses Without the Use of Fungicides and Nematicides and Without Nonchemical Controls. CRC Handbook of Pest Management in Agriculture, Vol. 1, p.139f.). In economic terms, the cessation of fungicide use would result in losses to field crops, vegetable crops, and fruit and nut crops estimated to total over two billion dollars (ibid.). Some crops would be particularly hard hit, e.cr, peanut losses would be expected to be >70% of the total crop, pecan losses >65% of the total crop, tomato losses >60% of the total crop, potato losses >40% of the total crop, and fruits such as apples, cherries, peaches, and pears each >50% of their total crop (ibid.).

Fungal attack of wood products is also of major economic importance with an estimated one billion dollars in damage annually (not including damage to living trees) in the U.S., even with the extensive use of existing preservatives (M. P. Levi, Fungicides in Wood Preservation, In *Antifungal Compounds*, M. Siegel and H. Sisler, eds., Marcel Dekker Inc., N.Y., 1977). Hundreds of fungal species have been isolated from wood products. Surface molds result from infestation by genera including, but not limited to, *Trichoderma spp., Gliocladium spp., Penicillium spp., Aspergillus spp.,* and *Alternaria spp.* Sap stain fungi include, but are not limited to, *Ceratocystis spp., Diplodia spp., Graphium spp., Aureobasidium spp.,* and *Cytospora spp.* Decay fungi responsible for a large proportion of the economic losses include, but are not limited to, *Coniophora spp., Lentinus spp., Lenzites spp., Polyporus spp., Poria spp.,* and *Merulius spp.* Soft-rot fungi include, but are not limited to, *Ascomycetes spp., Chaetomium spp.,* and Fungi Imperfecti.

Additional products that are susceptible to fungal infestation include textiles, plastics, paper, rubber, adhesives, emulsion polymers, leather, cosmetics, household disinfectants, deodorants, and paint. (C.C. Yeager, Fungicides in Industry, in *Antifungal Compounds*, M. Siegel and H. Sisler, eds., Marcel Dekker Inc., N.Y., 1977). More work has been done on paint than on any other substrate. Fungi that attack painted surfaces often disfigure the paint film to the point where replacement is required. Repainting can solve the problem only temporarily as the organism may erupt through the new coating. Paint infestations include, but are not limited to, *Pullularia spp., Cladosporium spp., Aspergillus spp.,* and *Penicillium spp.* The only successful method of combating fungal growth on paint systems requires the addition of a suitable fungistat or fungicide.

The development of antifungal drug therapies has not evolved as rapidly as the development of antibacterial drug therapies in large part because the human or animal host and the fungal pathogen are both eukaryotes and have many drug targets in common. To date, most of the antifungal drugs and lead compounds have been active against components of the fungal cell surface or membrane (New Antifungal Agents, J. R. Graybill, Eur. J. Clin. Microbiol. Dis. 8:402–412, 1989; Targets for Antifungal Drug Discovery, Y. Koltin, Annual Reports in Medicinal Chemistry 25:141–148, 1989; Screening of Natural Products for Antimicrobial Agents, L. Silver & K. Bostian, Eur. J. Clin. Microbiol. Dis. 9:455–461, 1990; *New Approaches for Antifunqal Drugs*, P. B. Fernandes, ed, Birkhauser:Boston, 1992; *Scrip's Antifungal Report*, by PJB Publications Ltd, 1992). For example, polyene macrolides bind to fungal-specific ergosterol on the cell surface and azole drugs inhibit an ergosterol biosynthetic enzyme. While there has been some effort directed at intracellular targets, such as tubulin and nucleotide metabolism, the resulting compounds, such as benomyl and fluorocytosine, have problems with toxicity and resistance. Cycloheximide (Actidione) is used as a fungicide on some crops even though it is not particularly specific for fungi. Blasticidin S is also used as an antifungal agent on crops.

Not only are fungal-specific therapeutics difficult to identify, but many of the drugs currently available for treatment of mycoses have significant side effects or lack effectiveness against some important pathogens. For example, amphotericin B, an antifungal polyene macrolide antibiotic, has both short-term and long-term adverse effects, ranging from nausea and vomiting to kidney damage. Azole drugs such as clotrimazole and miconazole have such adverse side effects that their use is generally limited to the treatment of topical or superficial infections. The more recently developed triazole drugs, such as fluconazole, have fewer side effects but are not completely effective against all pathogens. Also, some evidence exists for the development of resistance to these drugs. There is therefore an ongoing need for novel antifungal drugs with few side effects and with effectiveness against pathogens for which current drugs are inadequate.

Furthermore, fungal and mycotic pathogens often are either naturally resistant, or develop resistance, to many therapeutics by virtue of cellular permeability barriers to drug entry. Development of fungicide resistance occurs when a fungal cell or a fungal population that originally was sensitive to a fungicide becomes less sensitive by heritable changes after a period of exposure to the fungicide. Most instances of resistance are related to a change at the site of action or a change in the uptake of the fungicide, with detoxification being a rare event (J. Dekker, Preventing and Managing Fungicide Resistance, Pesticide Resistance: Strategies and Tactics in Man). In certain applications (e.g., agriculture) it is possible to combat resistance through alternation of fungicides or the use of fungicide mixtures. To prevent or delay the buildup of a resistant pathogen population, different chemicals that are effective against a particular disease must be available. One way of increasing the number of available chemicals is to search for new sitespecific inhibitors (ibid.). Thus, the challenge is to develop methods for identifying compounds which can penetrate the pathogen and specifically kill it or arrest its growth without also adversely affecting the human, animal, or plant host.

Classical approaches for identifying antifungal compounds have relied almost exclusively on inhibition of fungal growth as an endpoint. Libraries of natural products, semisynthetic, or synthetic chemicals are screened for their ability to kill or arrest growth of the target pathogen or a related nonpathogenic model organism. These tests are cumbersome and provide no information about a compound's mechanism of action. The promising lead compounds that emerge from such screens must then be tested for possible toxicity to the human, animal, or plant host, and detailed mechanism-of-action studies must subsequently be conducted to identify the affected molecular target and precisely how the drug interacts with this target.

Because mycoses are assuming even greater clinical importance, especially with the growing number of immunocompromised or immunosuppressed individuals, pressure has mounted to develop more effective methods for antifungal and antimycotic drug discovery. One approach uses different in vitro assays to target specific pathways that are deemed either to be unique to fungi, or sufficiently different from their human, animal, or plant counterparts that one might reasonably expect the fungal pathway to be differentially sensitive to the desired drug. Examples of pathways that are unique to fungi include chitin synthesis and degradation. Individual enzymes responsible for key steps in these pathways are being purified and used for in vitro studies to identify potential inhibitors. Examples of fungal targets that might be differentially sensitive to a drug compared to their human, animal, or plant counterparts include components required for mRNA splicing and topoisomerases. The specific molecular targets can be purified and used for in vitro studies to identify potential inhibitors. The in vitro studies in use are of two broad types: 1) purified target macromolecules are used in in vitro assays to screen large compound libraries for inhibitory drugs, or 2) the purified target molecule is used for a rational drug design program which requires first determining the structure of the macromolecular target or, preferably, the structure of the macromolecular target in association with its customary substrate or ligand. This information is then used to design inhibitory compounds which must be synthesized and tested further. Test results are used to refine the molecular models and drug design process in an iterative fashion until a lead compound emerges.

While these current methods offer certain improvements over the traditional screens that simply evaluate fungal growth in the presence and absence of a test compound, they still have limitations. On the positive side, these methods represent a relatively efficient, focused approach to drug discovery and the lead compounds they identify, by definition, will have known targets and mechanisms of action. However, because these methods are performed in vitro using a purified macromolecular target, the lead compounds that emerge may fail to kill or arrest the growth of fungal pathogens for a variety of reasons. The potential lead may not get into the fungal cell because of transport or permeability barriers. If it does get into the cell it may be inactivated by sequestration, modification or degradation. Conceivably, the cell may have a redundant biochemical pathway or a target that is not sensitive to the drug. Also, the theoretical basis for selecting a single macromolecule as the target for an in vitro drug development program may rest on assumptions that later prove unwarranted.

It has been recognized by several authors that the fungal translational elongation factor EF-3 would be a good target for antifungal compounds. However, as is clear from the following citations, none of these authors have suggested specific m ds for exploiting EF-3 to identify new anti-fungal or anti-mycotic agents. M. F. Tuite, Trends in Biotechnol. 10:235–239, 1992, describes the identification and exploitation of new antifungal targets. He states that:

"EF-3 is an absolute requirement for protein synthesis on S. cerevisiae ribosomes but not on the mammalian ribosome.

Subsequent studies have confirmed that soluble EF-3 is found only in fungi. . . . While its precise role in translation remains to be defined, biochemical studies have suggested that EF-3 provides an essential nucleotidase activity. . . . Preventing EF-3 binding to the fungal ribosome may therefore represent a new antifungal strategy and, while studies to date have focused on EF-3 from S. cerevisiae, the recent isolation and demonstration that C. albicans EF-3-encoding gene can substitute functionally for its S. cerevisiae counterpart, will provide a means of bypassing the difficulties of undertaking molecular-genetic studies in C. albicans. . . Identification of a potential antifungal target, however, is only the first step in ultimately producing an effective antifungal compound to combat the increasing occurrence of life-threatening fungal diseases. Either (1) a high throughput screen must then be developed to identify potential inhibitors that act specifically on the target, or (2) detailed structural information must be obtained for the target molecule to facilitate the rationale design of effect antifungal drugs. These are not trivial tasks, and they both rely on the identification of new antifungal targets." [citations omitted.] Colthurst et al., Mol. Microbiol. 6:1025, 1992 state:

"EF-3 therefore represents an almost unique example of an essential polypeptide apparently unique to fungal species yet which has no apparent mammalian counterpart (although the essential activity EF-3 supplies to fungal ribosomes actually may be an intrinsic property of a mammalian ribosomal protein). The demonstration of its essential nature in S. cerevisiae highlights the potential of EF-3 as a target for rationally designed antifungal drugs. While inhibition of the ribosome-dependent nucleotidase activity associated with EF-3 may not represent an effective target, an ability to block its association with the ribosome may be a more realistic goal. The demonstration that EF-3 from an important human pathogenic yeast, namely C. albicans, can be functionally expressed in a genetically manipulable host such as S. cerevisiae will greatly assist a molecular genetic dissection of the functional role of this translation factor in protein synthesis and thereby facilitate attempts to rationally design antifungal agents targeted at EF-3." [citations omitted.] Colthurst et al., 80 FEMS Microbiology Letters 45, 1991 states "EF-3 may also represent an important potential target for anti-fungal agents particularly given the increasing prevalence of Candida infections amongst individuals with suppressed immune systems."

SUMMARY OF THE INVENTION

The present invention relates to methods for identifying new antimycotic agents and for using these agents to treat mycotic diseases and prevent other mycotic infestations, such as, but not limited to, those described in Human Mycoses, E. S. Beneke, Upjohn Co.:Kalamazoo, Mich., 1979. These methods identify antimycotic agents that affect mycotic translation, the process by which mycotic cell systems synthesize proteins. By combining the convenience and target specificity of in vitro biochemical methodology with all the attributes of whole-cell assays, these methods make it possible to screen large collections of natural, semisynthetic, or synthetic compounds for antimycotic agents.

Although it has been recognized that translation may be a fertile area: for targeting antifungal agents (Targets for antifungal drug discovery Y. Koltin, Annual Reports in Medicinal Chemistry 25:141–148, 1989; Screening of natural products for antimicrobial agents, L. Silver & K. Bostian, Eur. J. Clin. Microbiol. Dis. 9:455–461, 1990; Antifungal drug development: the identification of new targets, M. F.

Tuite, Trends in Biotechnol 10:235–239, 1992), to Applicant's knowledge, these authors have not suggested specific methods for identifying translation-specific antifungal agents.

Inhibitors of translation have proven their value in treating bacterial infections. Although specific inhibitors of mycotic translation are desirable for treating mycotic infestations, this type of therapy has not been used due to the inability of previous methods to identify these compounds.

The methods of the present invention provide an efficient, focused approach to drug discovery with significant improvements over previous methods. One major improvement is a set of methods for identifying compounds that inhibit protein translation without knowing, a priori, the specific macromolecular target of the compound, while still permitting the subsequent identification of the macromolecular target. A second major improvement is a method for increasing the efficiency of drug discovery by ensuring that lead compounds are more likely to reach their molecular target inside the test organism.

By "mycotic cell system" is generally meant the cell translation system of a mycotic cell. Such a system will preferably include all the enzymes and cofactors necessary for translation to occur. In preferred embodiments, it means a whole mycotic cell, most preferably a living and growing cell.

For the purposes of this Application, the terms "fungal cell" and "mycotic cell" are used interchangeably, and include all organisms, including *Pneumocystis carinii*, belonging to the taxonomic group Fungi, as recognized by those skilled in the art, as well as all organisms known or believed to cause diseases known as mycoses, using a broad definition of the term mycoses, which includes nonfungal pathogens, such as "fungal-like" bacteria, e.g., Actinomyces and Mycobacteria, as recognized by those skilled in the art (*Human Mycoses*, E. S. Beneke, Upjohn Co.:Kalamazoo, Mich., 1979).

Target mycotic pathogens include fungal pathogens, fungal pests, and non-fungal pathogens, such as "fungal-like" bacteria. Some of the compounds identified by the methods of this invention also will be effective against other so-called non-bacterial "lower eukaryotes," such as, but not limited to, protozoa, giardia, dinoflagellates, and helminths, as well as fungal pathogens of animals and plants, and fungal infestation of non-living materials, such as, but not limited to, grains and other foodstuffs, wood, paper, and other natural products, and paint, rubber, adhesives, emulsion polymers, and other synthetic products.

The present invention features methods for identifying any agents which cause a significant reduction in mycotic translation. Such agents can then be screened to ensure that they are specific to mycotic translation systems and have little or no effect on host cell translation systems such that the agents can be used in a therapeutic or prophylactic manner. If such agents have some effect on host cell systems they may still be useful in therapeutic treatment, particularly in those diseases which are life threatening, such as systemic candidiasis.

Such agents may either interact directly with mycotic RNA, for example, by hybridizing with mycotic RNA, or bind or interact with other components of the mycotic translation system. While antisense nucleic acids, antibodies, and other proteins may exemplify antimycotic agents identified by the present invention, the applicant is particularly interested in the identification of agents of low molecular weight (less than 10,000 daltons, preferably less than 5,000, and most preferably less than 1,000) which can be readily formulated as useful antimycotic agents. The invention features such low molecular weight agents in preferred embodiments.

Once isolated, the mycotic-specific agents can be put in pharmaceutically acceptable formulations, and used for specific treatment of fungal disease or other mycoses with little or no effect on cells of the host organism.

Many of the following methods make use of systems in which a mycotic inhibitor actually enhances growth of a mycotic cell in some compositions, and yet is useful to kill or reduce mycotic cell growth in pharmaceutical compositions. This is possible because the systems described below are generally designed to allow growth under defined environment-inwhich mutant mycotic cells are used. However, in the absence of such mutations and specific environment, and at a higher dose, the inhibitor will act as an inhibitor of mycotic translation and can be an effective antimycotic agent.

These methods make use of many systems which have been used previously for other purposes, but have not been recognized as useful for detection of antimycotic agents. Such systems may need modifications to optimize their utility, by methods known in the art. For example, Moehle and Hinnebusch, Mol. Cell. Biol. 11:2723, 1991; Firoozan et al., Yeast 7:173, 1991; Ray and Butow, Mol. Gen. Genet. 173:227, and 173:239, 1979; Warner and Gorenstein, Nature 275:339, 1978; Ezekiel and Elkins, Biochem. Biophys. ACTA 166:466, 1968; Gross and Pogo, Biochemistry 15:2082, 1976; Oliver and McLaughlin, Mol. Gen. Genet. 154:145, 1977; Clare and Oliver, Mol. Gen. Genet. 188:96, 1982; Waltschewa et al., Cell 33:221, 1983; and Stateva and Venkov, Mol. Gen. Genet. 195:234, 1984 describe systems which can be used in the present invention. These publications are hereby incorporated by reference. In some of these publications, known translation inhibitors of fungal cells are used, whereas in the present invention screening of unknown inhibitors is proposed as well.

In a first aspect, the present invention features a method for identifying antimycotic agents relying upon a translation-responsive gene product. This method involves constructing a mycotic cell in which the production of a reporter molecule, measured as a percentage of overall translation, increases under conditions in which overall mycotic cell translation is reduced. Specifically, the reporter molecule is encoded by nucleic acid either translationally linked or transcriptionally linked to a sequence constructed and arranged to cause a relative increase in the production of the reporter molecule when overall translation is reduced. Preferably, the overall translation is measured by the expression of a second indicator gene whose expression, when measured as a percentage of overall translation, remains constant when the overall translation is reduced. The method further involves contacting the mycotic cell with a test compound, and determining whether the test compound increases the production of the first reporter molecule in the mycotic cell.

By "translationally linked" is meant that the leader sequence involved in translational control is linked appropriately to cause proper translation of the linked gene at the desired time.

By "transcriptionally linked" is similarly meant that the promoter is constructed and arranged to cause transcription of the linked gene at the desired time in an appropriate manner.

By "translation-responsive gene product" is meant a gene product whose synthesis is sensitive to the overall rate of translation. Two general classes of translation-responsive gene products may be used.

The first class consists of gene products whose synthesis is regulated at the level of translation in a way which is sensitive to the overall rate of translation. An example of such a translation-responsive gene is a GCN4-type gene.

By "GCN4-type gene" is meant a gene including a regulatory sequence which increases the expression of genes translationally linked to it when overall cell translation decreases. In the example of GCN4 of S. cerevisiae, the regulatory sequence is in the mRNA 5' to the open reading frame (ORF) that encodes the GCN4 polypeptide. However, the regulatory sequence may be found anywhere within the mRNA of a GCN4-type gene. Those skilled in the art will recognize equivalents in other mycotic cells.

When using a GCN4-type gene product, either directly or indirectly, as the reporter molecule, a GCN-type gene may be mutated in the cell system because compounds that do not inhibit translation but do activate the General Amino Acid Control pathway would also cause an increase in the translation of the GCN4-type gene product. That is, the cell system is devised so that translation inhibitory compounds can be detected without detection of non-useful compounds. In a preferred embodiment, the GCN-type gene that is mutated is the S. cerevisiae GCN2 gene.

By "GCN-type" gene is meant a gene necessary for regulation of amino acid biosynthesis by the General Amino Acid Control pathway, also known as the Cross-Pathway Control. Mutants defective for a GCN-type gene are defective for the ability to regulate multiple amino acid biosynthetic pathways in response to an amino acid limitation. This definition of GCN-type gene includes, but is not limited to, S. cerevisiae genes designated GCN or GCD, and their cognates in other organisms.

The term "General Amino Acid Control" is used in its art recognized manner.

The second class consists of gene products whose synthesis is regulated at the level of transcription in a way which is sensitive to the overall rate of translation. An example of such a translation-responsive gene is an RPL16A-type gene. An RPL16A-type gene is one that has a promoter that causes transcription of the gene transcriptionally linked to it to increase when overall cell translation decreases. In the example of RPL16A gene of S. cerevisiae, the cells must first be placed in a special condition, namely, an amino-acid-limitation medium, so that the RPL16A gene would respond in the described manner. Those skilled in the art will recognize equivalents in other fungal or mycotic cells. When using a RPL16A-type gene product as the reporter molecule, a GCN-type gene is preferably mutated because compounds that do not inhibit translation but do activate the GCN-type gene would cause a reversal of the special amino-acid-limitation condition; such a reversal would be difficult to distinguish from a translational inhibition in the assay described herein. With the aforesaid mutation, the cell system will specifically detect translational inhibitors.

In a preferred embodiment, the reporter molecule is itself the translation-responsive gene product whose production increases when overall translation is reduced.

In another preferred embodiment, the reporter is a different molecule whose production is linked to that of the translation-responsive gene product. Such linkage between the reporter and the translation-responsive gene product can be achieved in several ways. A gene sequence encoding the reporter may, for example, be fused to part or all of the gene encoding the translation-responsive gene product and/or to part or all of the genetic elements which control the production of the gene product. Alternatively, the translation-responsive gene product may stimulate transcription and/or translation of the gene encoding the reporter, either directly or indirectly.

In a further preferred embodiment, the production of the reporter molecule is measured by the enzymatic activity of the reporter gene product, such as β-galactosidase.

In other preferred embodiments, the cell system is a whole mycotic cell and the method involves measuring the growth of the whole cell under defined conditions. Such defined conditions are chosen so that growth is observed when a translation inhibitor is present, but little or no growth occurs in the absence of such an inhibitor. Such conditions may be achieved in several ways. One way is to grow a mycotic cell system with a competitive inhibitor of the reporter gene product. In a further prefered embodiment, a mycotic cell system is grown with 3-amino-1,2,4,-triazole (3AT), which is an inhibitor of the reporter gene product imidazoleglycerol dehydrogenase, the S. cerevisiae HIS3 gene product. Increased expression of the HIS3 gene causes increased resistance to 3AT. Alternatively, a partially defective, or bradytrophic, allele of a reporter gene can be used. In another further preferred embodiment, the S. cerevisiae his1-29 gene is used. Increased expression of the bradytrophic allele can compensate for its intrinsic defect, and convert some cell lines from a His$^-$ to a His$^+$ phenotype.

In yet another preferred embodiment, the production of the reporter molecule is measured by its ability to ameliorate the deleterious effects of a toxic agent such as 5-fluorotryptophan (5-FT) or 3AT.

In other preferred embodiments, the cell system is an extract of a fungal or mycotic cell that was grown under defined conditions, and the method involves measuring transcription or translation in vitro. Such defined conditions are selected so that transcription or translation of the reporter is increased by the addition of a translation inhibitor to the cell extract.

In a second aspect, the invention features a method for identifying antimycotic agents utilizing mycotic cell systems that are sensitive to perturbation to one or several translational components.

This method involves constructing mutant mycotic cells in which one or more of the translational components is present in altered form or in a different amount compared with a corresponding wild-type cell. Such wild-type cell is isogenic with each such mutant cell, by which is meant that the allelic forms of all other genes except those which encode the altered translation component(s) are the same in the wild-type as in the mutant cell.

This method further involves examining a test compound for its ability to perturb translation by assessing the impact it has on the growth of the mutant and wild-type cells. Compounds which perturb translation by acting on a particular component that participates in translation cause a mutant mycotic cell which has an altered form or amount of that component to grow differently from the corresponding wild-type cell, but do not affect the growth, relative to that of the wild-type cell, of other mutant cells bearing alterations in other components participating in translation. This method thus provides not only a means to identify whether a test compound perturbs translation but also an indication of the site at which it exerts its effect. The translation component which is present in altered form or amount in a cell whose growth is affected by a test compound is likely to be the site of action of the test compound.

In a third aspect, the invention features a method for identifying antimycotic agents which interfere with steps in translational accuracy, such as maintaining a proper reading frame during translation and terminating translation at a stop codon.

This method involves constructing mutant mycotic cells in which a detectable reporter polypeptide can only be produced if the normal process of staying in one reading frame or of terminating translation at a stop codon has been disrupted. This method further involves contacting the mutant mycotic cells with a test compound to examine whether it increases the production of the reporter polypeptide.

In a preferred embodiment, the mutant mycotic cells contain a gene fusion whose transcript contains the coding sequence for a reporter polypeptide with either a reading frame shift or a translation stop codon, either of which will significantly reduce translation of a functional product. Only if the normal translation process is disrupted will the coding sequence for the reporter polypeptide be translated.

In a fourth aspect, the invention features methods for identifying antimycotic agents which either activate or inhibit the function of a GCN2-type kinase responsible for inhibiting mycotic cell translation such as the *S. cerevisiae* eIF-2alpha kinase (also known as the GCN2 kinase).

One method involves growing mycotic cells in the presence of a test compound and a metabolite analog that is toxic to the cell unless the availability of the normal form of the metabolite is increased due to the activity of a GCN2-type kinase. This method further involves selecting compounds which at low concentrations either partially activate the kinase or inactivate a function that antagonizes the kinase, such as a phosphatase, thereby conferring a growth advantage on cells grown in the presence of toxic analogs. At higher concentrations, such compounds activate the kinase to levels deleterious for growth because hyper-activation of the kinase causes a severe reduction of overall translation. Such compounds are effective antimycotic agents.

Such toxic analogs are well known in the art, including substituted amino acids or purines which are recognized sufficiently well by the cell to be included or used as the normal amino acid or purine, but produces a harmful product or causes blockage of a critical enzyme activity.

A related method involves contacting a mutant mycotic cell bearing a constitutively activated allele of a GCN2-type kinase with a test compound. Compounds which at low concentrations partially inactivate the kinase, or antagonize the activity of the kinase in another manner, also ameliorate the deleterious effect conferred by the constitutively activated allele of the kinase. At higher concentrations, such compounds inactivate the kinase to an extent detrimental for mycotic growth. Such compounds are also effective antimycotic agents.

By "GCN2-type kinase" is meant a protein kinase which phosphorylates a translation component in such a way as to inhibit overall translation. In the preferred embodiment, a GCN2-type kinase is one which can specifically phosphorylate the serine residue at position 51 of the *S. cerevisiae* translation component eIF-2alpha.

By "function" is meant an activity which has the opposite effect of said GCN2-type kinase. It includes, but is not limited to, phosphatase, translation components that are normally inhibited by said GCN2-type kinase, such as eIF-2 and eIF-2B.

By "constitutively activated allele" is meant an allele (version) of a gene encoding a protein which is phenotypically active under all conditions tested.

By "constitutively activated allele of a GCN2-type kinase" is meant an allele of a gene encoding a GCN2-type kinase which is phenotypically active under conditions that would keep the wild-type GCN2-encoded protein inactive, e.g., on amino-acid-balanced medium, which is also referred to as a repressing condition.

For translation to proceed, components of the translational machinery must make reversible physical contacts with one another. If these contacts could be made either more permanent or prevented from occurring, translation would be blocked.

Thus, in a fifth aspect, the invention features methods for generating and/or identifying antimycotic agents which interfere with specific interactions between components of the translational apparatus.

One method involves constructing mycotic cells that will synthesize a mutagenized form of a translational component in response to an external signal. Some of the mutant forms of translational components, e.g., dominant negative alleles of such components, make more permanent contacts to their translational component partners than their wild-type counterparts. This method further involves identifying mutant translational components that have a deleterious effect on mycotic growth. Such mutant translational components are effective antimycotic agents.

In a preferred embodiment, the smallest possible domains that mediate these more permanent contacts are identified by successively reducing the size of the mutant form, and the smallest functional domain and its derivatives and analogs are then tested for antimycotic activity.

Another method involves constructing mycotic cells in which one translational component is fused to a first heterologous domain, e.g., a DNA-binding peptide, and another translational component is fused to a second heterologous domain, e.g., a transcription-activation domain. These heterologous domains are chosen for their ability to generate a measurable signal when the two translational components physically interact with each other. For example, the transcription-activation domain can activate transcription and subsequent translation of a detectable reporter when the two translational components physically interact with each other. The interacting translational component domains are then reduced to peptides of the minimum size which retain the activation function. The peptides and derivatives and analogs of the peptides are tested for their efficacy as competitive inhibitors of the bona fide interaction by first determining if they decrease the production of the reporter polypeptide, and then determining if they interfere with the relevant step in the translation process. An efficient competitive inhibitor of a mycotic translation component is an effective antimycotic agent.

By "derivative" or "analog" is meant a compound having the desired biological properties of the peptide but altered at one or more amino acid positions. Such alternatives may be substitution of one amino acid for another amino acid at up to three locations, preferably a charged amino acid for another charged amino acid, or may be substitution of one chemical group for another chemical group at up to three locations within the peptide.

In yet another method, a test compound with no known relationship to the peptide sequence is tested for its ability to inhibit the specific interaction in the same manner as just described.

In a sixth aspect, the invention features a method for identifying antimycotic agents which inhibit translation specifically in mitochondria, by measuring protein synthesis in the presence of a test compound in a mycotic cell in which non-mitochondrial translation has been stopped.

By "non-mitochondrial translation has been stopped" is meant that the process of translation in the non-mitochondrial cellular compartments, and particularly the cytoplasm, has been preferentially blocked with little or no effect on the process of translation in the mitochondria.

In a preferred embodiment, the non-mitochondrial translation is stopped by cycloheximide. In another preferred embodiment, the non-mitochondrial translation is stopped by another small-molecule inhibitor. In yet another preferred embodiment, the non-mitochondrial translation is stopped by using a mycotic cell with a temperature-sensitive allele of one or more cytoplasmic-translation components, and shifting the cell to a nonpermissive temperature.

In a seventh aspect, the present invention features a method that enhances the access of test compounds to a cell or an organism, by mutating or deleting a gene or genes which encode a protein or proteins responsible for providing a permeability barrier for a cell or an organism.

By "permeability barrier" is meant any mechanism which allows a cell or an organism to preclude uptake, pump out, sequester, or detoxify any compounds which may damage them. In mycotic cells, such mechanisms include those encoded by, or whose production is regulated by, the products of the pleiotropic drug resistance (PDR) genes.

In a preferred embodiment, one or more of the PDR genes are inactivated or removed from mycotic cells, making possible the detection of a test compound's ability to interfere in a biochemical pathway, which might otherwise go undetected because of the rapid excretion of the test compound from the mycotic cell mediated by an active PDR gene product.

Thus, the applicant has determined many ways for screening for specific mycotic translation inhibitors, including those not active at the elongation factor EF-3 of *S. cerevisiae*. Those in the art will recognize that the invention has significant advantages for screening for antimycotics as discussed above. Many reporter genes can be used in the above methods. Those skilled in the art will recognize any desired such genes that can be used, many of which are commonly used in other systems to give readily detectable signals, such as a fluorescent signal, or simply cell growth. The antimycotics discovered are useful in in vitro assays as well as in in vivo treatments. Such assays include routine scientific experiments performed by laboratory researchers.

The invention also features novel agents discovered by the claimed methods and the uses of these agents, including, but not limited to, the treatment or prophylactic treatment of mycotic infections.

Other features and advantages of the invention will be apparent from the following detailed description of the preferred embodiments, and from the claims.

DESCRIPTION OF THE PREFERRED EMBODIMENTS

Drawings

The figures will first be described.

Figure 1A:
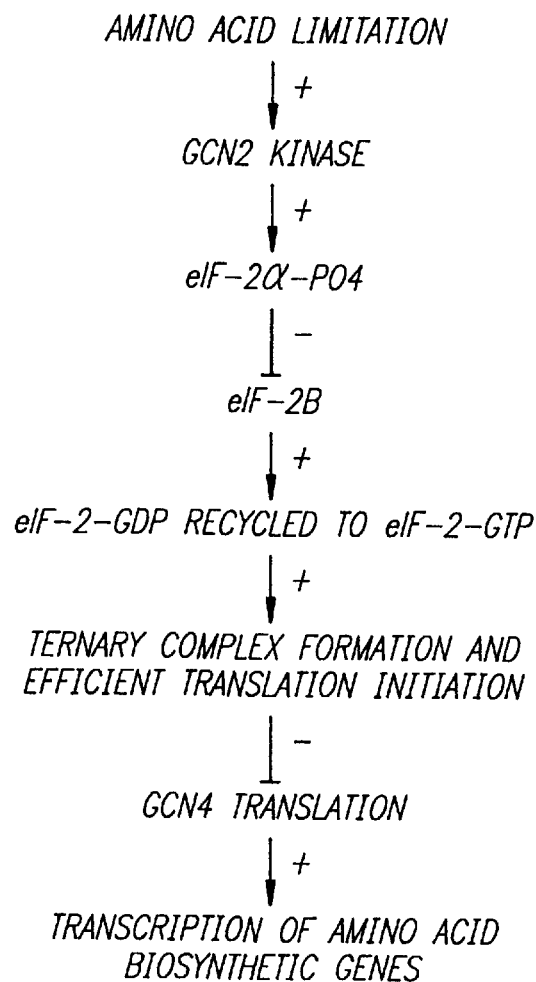
Figure 1B:
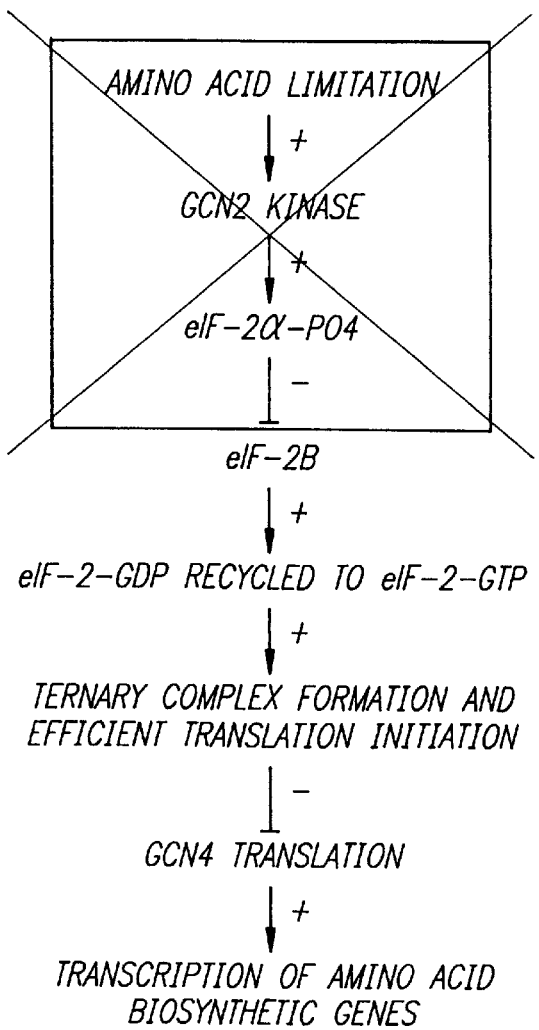

FIG. 1 (A) shows the general control as a monitor of translational status. Translation of the GCN4 MRNA is regulated by the pathway shown. Amino acid limitation activates (+) the kinase GCN2, which specifically phosphorylates the serine-51 residue on the alpha subunit of the trimeric translation initiation factor eIF-2. The serine-51-phosphorylated form of eIF-2alpha is an inhibitor (-) of the translation initiation factor eIF-2B, which is also known as GEF. The factor eIF-2B is responsible for recycling the factor eIF-2 from the inactive, GDP-bound state to the active, GTP-bound state. Efficient recycling during amino-acid-sufficient conditions results in efficient formation of ternary complexes (eIF-2-GTP-tRNA-met;) and efficient translation initiation. Efficient translation initiation results in very little translation of the GCN4 ORF due to the presence of short upstream ORFs in the mRNA leader. In contrast, during conditions of amino acid limitation, the GCN2 kinase is activated. Its phosphorylation product inhibits recycling of eIF-2, thereby reducing ternary complex formation and inhibiting translation initiation. The reduction in translation initiation causes a dramatic increase in the translation of GCN4, a transcriptional activator of amino-acid-biosynthetic genes. Translation of GCN4 can be monitored by its effect on growth with in vivo assays of amino acid biosynthesis, or by its effect on expression of a reporter gene with in vivo or in vitro enzyme assays.

FIG. 1 (B) is a schematic for general amino acid control assay. Knowledge of the general amino acid control pathway is exploited to screen for inhibitors of translation. GCN2 is the only kinase known in yeast that phosphorylates the serine-51 of eIF-2alpha. In an otherwise wild-type strain lacking GCN2, GCN4 translation is always low, even during amino-acid-limitation conditions. Genetic defects in genes encoding eIF-2 and eIF-2B can cause high level GCN4 translation, even during amino-acid-sufficient conditions. Small molecules that inhibit translation initiation will mimic the effect of serine-51-phosphorylated eIF-2alpha or genetic defects in translation factor genes, and cause high level GCN4 translation.

In both FIG. 1 (A) and FIG. 1 (B), (+) indicates the item above the arrow stimulates formation of the item or condition below the arrow; (-) indicates the item above the arrow inhibits formation of the item or condition below the arrow.

FIG. 2 shows the histidine biosynthetic pathway. Synthesis of histidine starts with the precursor phosphoribosylpyrophosphate (pRpp) and the enzyme encoded by the HIS1 gene. The enzyme encoded by the HIS3 gene can be competitively inhibited with 3-aminotriazole (3AT). Transcription of most or all of genes encoding enzymes in this pathway is stimulated by GCN4.

FIG. 3 shows a general control growth assay. In several of the methods in this application, putative translation blockers are screened with a "Paradoxical growth assay". The assays are designed such that a low dose of a translation blocker actually stimulates the growth of the test organism, while a higher dose inhibits the growth or even kills the test organism. These conditions require a growth medium that allows little or no growth of the test organism, and a reporter gene which both encodes a product that overcomes the growth limitation, and a transcriptional or translational control sequence that links partial translation inhibition with increased expression of the reporter. In each assay, a parallel culture is incubated with the test compound in parallel conditions, except that the growth limitation condition has been fulfilled, for example, by adding histidine when the reporter encodes a histidine biosynthetic enzyme. As shown in this figure, the cultures are grown as a lightly seeded lawn on solid medium, and the test compounds are applied to porous disks which are laid on top of the lawn. In these assays, many compounds have no effect on growth, some simply inhibit growth, while some inhibit growth at high concentrations but stimulate growth at lower concentrations. This last class of compounds are putative translation blockers. Note that depending on the amount of compound applied to the disk, the zone of growth inhibition could be small or nonexistent without jeopardizing the interpretation. These assays are very sensitive because they can identify lead compounds which have a sub-lethal effect on translation.

FIG. 4 depicts stringent control as a monitor of translation status. Transcription of many ribosomal protein genes, typified by RPL16A, which is one of a pair of genes encoding the ribosomal protein L16, is regulated by the pathway shown. Amino acid limitation increases the ratio of uncharged to charged tRNAs, where "charged" means aminoacylated. As this ratio increases, a translating ribosome is likely to stall at a codon for which the cognate charged tRNA is not available. Such a codon is called a "hungry" codon. It is believed that a yeast protein recognizes hungry codons and generates a form of starvation signal which causes a specific reduction in the transcription of ribosomal protein genes and other genes responsive to the stringent control pathway. When a sublethal concentration of a translation-elongation blocker is added to an amino-acid-limited cell culture, translation elongation, as well as charged tRNA consumption, is slowed, and, even though the amino acid limitation itself has not been,alleviated, the starvation signal is attenuated. As a result, transcription of stringent-control-responsive genes increases with the addition of the translation-elongation blocker. This phenomenon is known as "phenotypic relaxation of the stringent response". In this figure, (+) indicates the item above the arrow stimulates formation of the item or condition below the arrow; (−) indicates the item above the arrow inhibits formation of the item or condition below the arrow.

FIG. 5 shows a termination suppression assay. This assay is designed to identify inhibitors of translation termination. A translational stop codon (a nonsense codon) is introduced in the ORF, causing the full-length ORF to be translated at very low levels. A test compound that interferes with translation termination and causes the nonsense codon to be misread as a sense codon at a measurable frequency will increase the translation of the full-length ORF.

In the current embodiment the repressible acid phosphatase encoded by PHO5 is used, but there is nothing unique about this particular reporter that necessitates its use. This reporter is chosen because background levels of enzyme activity are sufficiently low, the enzyme assay is relatively simple, and the enzyme is localized on the external cell surface. These factors favor high through-put assays with intact cells. The native PHO5 mRNA has a large ORF that is not interrupted by a translational stop codon (or frameshift). For the purpose of this assay, a single stop codon is introduced into the open reading frame; several such alleles are made in parallel, as denoted by the arrows. It is preferred that the stop codon is introduced near the signal sequence cleavage site, because it is less likely at that location for the incorrectly inserted amino acid to interfere with enzyme activity or localization.

FIG. 6 (A) shows results of phenotypic relaxation assays with known translation blockers as test compounds. The known translation blockers were tested with a "paradoxical growth assay" similar to the one depicted in FIG. 3, using a strain of the relevant genotype RPL16A-HIS3 his3 gcn4 and the medium described in Example 2. The test compounds were dissolved in water, ethanol, or dimethylsulfoxide (DMSO); none of these solvents alone showed any effect in the assay. Ten of the test compounds scored positive in the assay: growth on 3AT was stimulated. Five of the test compounds were fungitoxic, that is, at higher concentrations they killed or prevented the growth of the yeast cells. Fourteen of the test compounds had no visible effect on the assay; most of these are known to be specific for prokaryotic ribosomes. Note that this assay was sensitive enough to identify emetine, gougerotin, and puromycin as positives. It has been reported that these three compounds inhibit yeast translation in vitro, but have no effect on intact yeast cells.

FIG. 6 (B) shows results of phenotypic relaxation assays with non-translation blockers. Assays were performed as for FIG. 6 (A), except that compounds and chemicals not known as translation blockers were tested to see how frequently a positive result (stimulation of growth on 3AT) was obtained. Compounds that stimulate growth on 3AT without affecting translation are called false positives. Many of these false positives are strong acids or bases; for each of these, neutralization of the pH resulted in loss of the growth stimulation on 3AT medium. (Note that it is formally possible that any of these compounds does affect translation in an unanticipated manner.) Nystatin stimulated 3AT-medium growth at higher concentrations, but not at lower concentrations.

Figure 7:
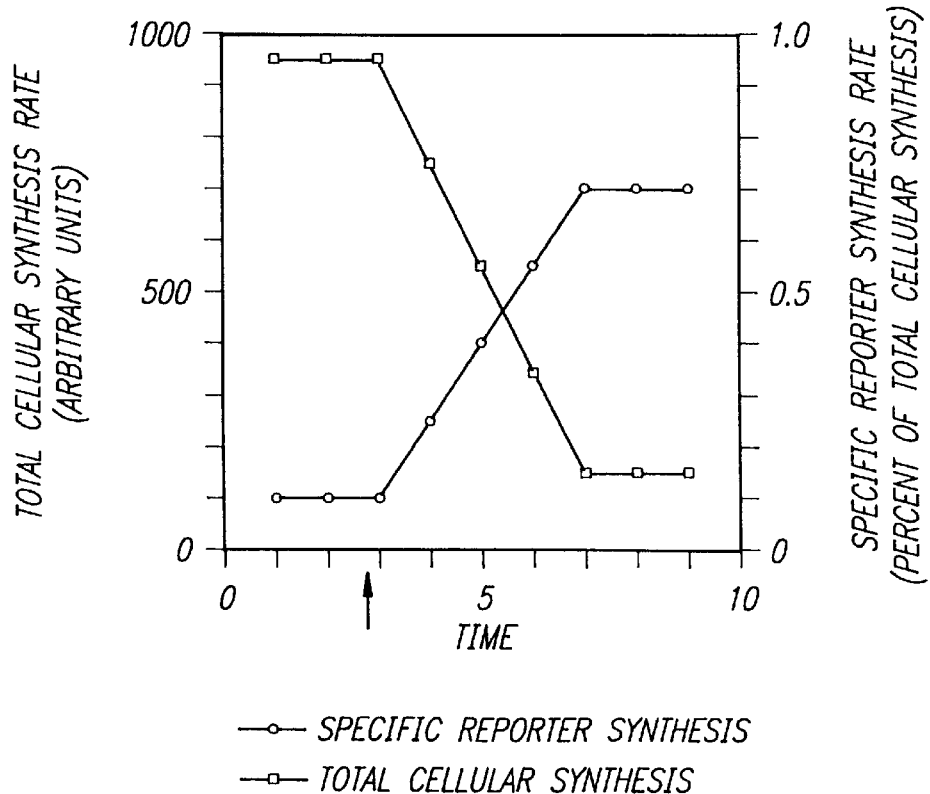

FIG. 7 is a graphical representation of a general assay scheme for overall translation assay methods. These assays rely on specific reporter genes whose translation or transcription increases, relative to total cellular translation or transcription, upon addition of a translation blocker. In these assays, total cellular, or even specific reporter gene, translation or transcription may go down. However, the translation or transcription of the specific reporter gene must increase relative to the total after addition of the translation blocker. The arrow denotes addition of the translation blocker.

FIG. 8 is a diagrammatic representation of a translation-component-specific assay. The preferred embodiment employs a set of isogenic strains where each one differs from the others only by alteration(s) of a translation-component gene(s). The set of strains are incubated in parallel in growth-permissive medium with various test compounds. In the absence of a translation-specific agent, or in the presence of such an agent below a certain threshold concentration, all strains grow except for a negative growth control shown in position A12. In the presence of a non-specific inhibitor, or of a translation-specific agent at a concentration that is too high, none of the strains grow except for a positive-growth control, shown in position B12. In the presence of a translation-specific agent in the appropriate concentration range, a subset of strains will not grow. The pattern of mutant- strains inhibited by the test compound will indicate the likely target(s) of the compound.

Figure 9:
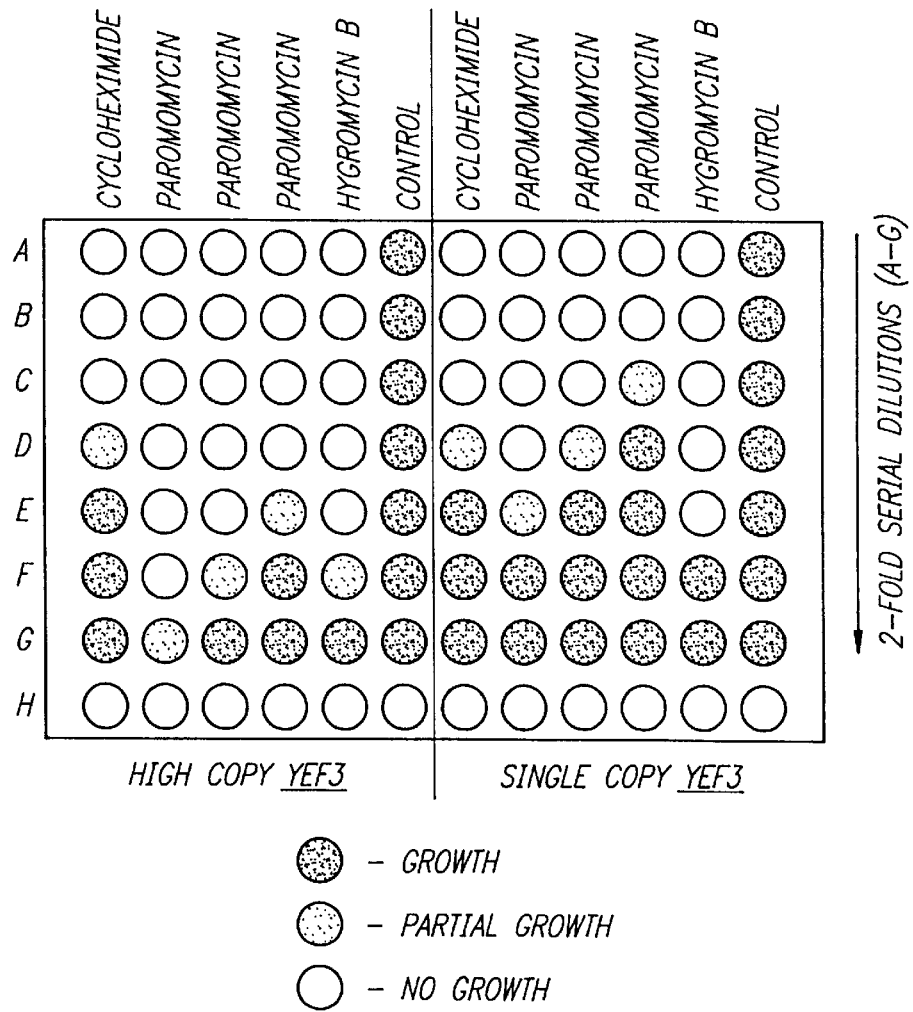

FIG. 9 is a representation of results obtained with isogenic yeast strains bearing *Saccharomyces cerevisiae* YEF3 gene. The yeast strains and culture conditions are described in Example #4 with the following, slight modification: 0.3 ml of fully diluted culture and 4 $\mu$l of test solution are added to wells "A", 0.15 ml of fully diluted culture is added to wells "B" through "G", and 0.15 ml of medium without cells is added to wells "H". After mixing the culture and test solution in each of wells "A", 0.15 ml is removed and added to the adjacent well "B", which already contains 0.15 ml of culture. After mixing, 0.15 ml is removed and added to the adjacent well "C", and so on through to wells "G", with the 0.15 ml removed from wells "G" being thrown away. The test solutions are indicated at the top of the grid: Cycloheximide (0.13 $\mu$/ml), Paromomycin (2.7, 1.3, and 0.67 mg/ml, from left to right, respectively), Hygromycin B (0.67 mg/ml, Control (deionized water).

The following are specific descriptions of various components or methods required in specific assays of this invention. These descriptions are not limiting in the invention and those of ordinary skill in the art will recognize that any mycotic cell system can be adapted for use in assays of this invention for screening for antimycotic compounds which are active in the translational system of that mycotic cell. Thus, while many of the examples below relate to the use of S. cerevisiae as a test system, those of ordinary skill in the art will recognize that other mycotic cell systems can be manipulated in a manner analogous to that in S. cerevisiae so that equivalent mycotic cell systems can be derived. In addition, while many of the examples provide growth assays, i.e., whole cell systems are used, those of ordinary skill in the art will recognize that extracts of such whole cells can be used so long as those extracts include all of the necessary translation components so that a translational assay system can be derived.

1. Choice of Test Organism

In a preferred embodiment, the assays make use of Saccharomyces cerevisiae (baker's yeast) as the test mycotic cell system. This organism is easy to grow, has a powerful molecular genetic repertoire which facilitates assay development, and has features in common with pathogenic fungi, e.g., the translation elongation factor EF-3 of C. albicans can functionally replace its counterpart in S. cerevisiae. There have also been reports that S. cerevisiae can be pathogenic in rodents or humans under certain conditions (e.g., Fungemia with Saccharomycetacea, H. Nielson, J. Stenderup, & B. Bruun, Scand. J. Infect. Dis. 22: 581–584, 1990). The preferred use of Saccharomyces cerevisiae is in no way meant to preclude using in the methods of this application other mycotice cell systems, such as, but not limited to, those listed in the background section of this application.

2. Genes that Act as Indicators of the Translational Status of the Cell

Two of the assays described below, namely the General Control Assay and the Phenotypic Relaxation Assay, center on monitoring the expression of genes GCN4 and RPL16A respectively, which are especially sensitive to the translational status of the cell. Other genes having advantageous properties to the current application can be identified through systematic searches. Explicitly, the advantageous properties of these genes to the current application are: 1) an increase or decrease in expression, as measured by its percent representation relative to total cellular mRNA or protein, during conditions of impaired translation, and 2) the ability to identify and manipulate the sequence elements conferring this regulation.

One such systematic search entails pulse-labeling cell cultures with a radioactive amino acid or amino-acid precursor in parallel during conditions of normal and impaired translation. After the labeling some or all of the individual proteins are separated by methods known to those skilled in the art, such as two-dimensional gel electrophoresis. Individual proteins which are differentially expressed during the two conditions with respect to total protein synthesis can be identified and isolated, and the corresponding genes cloned by methods known to those skilled in the art.

Another such systematic search entails searching for mRNAs that are differentially expressed, relative to total mRNA, under the two conditions. mRNAs can be identified by methods known to those skilled in the art (Molecular Cloning, a Laboratory Manual (2nd ed.). J. Sambrook, E. F. Fritsch, T. Maniatis, eds. Cold Spring Harbor Laboratory Press: N.Y., 1989). The properties of such genes are illustrated in FIG. 7, where a desired reporter gene has an increased level of expression compared to overall levels of translation.

3. General Control Assay

The invention features a method for screening for an antifungal agent, in which particular yeast genes exhibiting translational regulation that is sensitive to the translational capability of the cell are identified and used as indicators of test compound activity. Expression of these genes may be used to directly report test compound activity, either by measuring the gene products directly, by in vivo or in vitro assay, or by fusing their regulatory elements to suitable reporter genes and measuring production of the hybrid gene product in vivo or in vitro. Alternatively, the expression of the translational indicators may be eYed to drive expression of other genes that in turn function as the reporters of test compound activity. This method utilizes a mycotic, e.g., fungal, translation-responsive translational control nucleic acid sequence that allows preferential translation of a specific RNA or RNAs under translation-inhibiting conditions. In a preferred embodiment, the sequence is translationally linked to an RNA encoding a reporter polypeptide.

The method further includes contacting a cell or cell extract, e.g., a yeast cell or cell extract containing the sequence with a-potential antifungal agent under conditions that allow little or no synthesis of the reporter polypeptide in the absence of the agent.

The method finally includes determining whether the agent increases the level of translation of the reporter polypeptide. Paradoxically, any agent that increases this level is potentially useful as an antifungal agent, albeit at higher doses.

In a further preferred embodiment (See, FIG. 1A), referred to as the "General Amino Acid Control Assay", the activity of GCN4, a transcriptional activator of yeast biosynthetic genes (Protein Synthesis and Translational Control, A. G. Hinnebusch and S. W. Liebman, pp.626–736, in: The Molecular Biology of the Yeast Saccharomyces, J. R. Broach, J. R. Pringle, and E. W. Jones, eds., CHS Laboratory Press: N.Y., 1991), is used as a sensitive indicator of translation blockers since conditions that inhibit translation stimulate GCN4 expression, which is normally repressed to very low levels. The effect of test compounds on the synthesis or activity of GCN4 is detected using strains that synthesize a reporter gene product under GCN4 control. The reporter genes include but are not limited to: 1) genes whose products are required at elevated levels for cells to grow under selective conditions that prevent growth of cells in which GCN4 expression is repressed, or 2) genes whose products can be readily detected immunologically, pectrophotometrically, luminometrically, or with the aid of radioisotopes. The reporter genes may be physically separated from GCN4 such that their expression is regulated by the GCN4 gene product itself, or fused to a portion of the GCN4 gene 5 containing the necessary regulatory elements to make a genetic hybrid. The product of the genetic hybrid is synthesized under the control of the associated GCN4-regulatory elements while retaining reporter gene product activity.

By "fungal translation-responsive translational control nucleic acid sequence" is meant any nucleic acid which allows preferential translation of translationally associated RNA under translation-inhibitory conditions. Such nucleic acid is exemplified by the GCN4 mRNA leader which allows translation of associated ribonucleic acid during conditions of translation inhibition.

By "preferential translation" is meant that the mRNA is translated at a higher rate or with higher yield of protein under translation-inhibitory conditions, relative to that of total mRNA, when compared to the rate or yield under non-inhibitory conditions. In addition, the average of total cell mRNAs may be translated at a slower rate or with lower protein yield than in non-translation-inhibitory conditions. Such preferential translation can be readily detected as described below.

By "translation-inhibitory conditions" are meant conditions in which the overall rate of protein synthesis is reduced.

By "reporter polypeptide" is meant a peptide which is readily detectable, either by providing a colorimetric signal under certain environmental conditions or some other signal well known to those of ordinary skill in the art, as described below.

EXAMPLE 1

Monitoring GCN4 Expression

The General Amino Acid Control pathway is exquisitely sensitive to the translational status of the yeast cell (Protein Synthesis and Translational Control, A. G. Hinnebusch and S. W. Liebman, pp.626–736, in: *The Molecular Biology of the Yeast Saccharomyces*, J. R. Broach, J. R. Pringle, and E. W. Jones, eds., CHS Laboratory Press: N.Y., 1991). Referring to FIG. 1(A), in response to limitation for an amino acid, uncharged tRNA levels increase, and the GCN2 kinase is activated to phosphorylate eIF-2alpha on residue serine 51. This phosphorylated species inhibits the GDP-GTP exchange factor for eIF-2, known as eIF-2B or GEF, resulting in decreased levels of the active, GTP-bound form of eIF-2. In response to this deficiency, translation of the GCN4 ORF is derepressed. GCN4 binds to a consensus site found in the promoter of many genes encoding amino acid biosynthetic enzymes, which ultimately results in a net increase in amino acid biosynthesis. GCN4 binding sites are also present in the promoters of some tRNA synthetase genes, e.g., GCD5/KRS1, which encodes the lysine tRNA synthetase. In fact, a gcd5-1 mutant absolutely depends on an intact General Control pathway to increase expression to a level sufficient for growth (Autoregulation of the Yeast Lysyl-tRNA Synthetase Gene GCD5-KRS1 by Translational and Transcriptional Control Mechanisms, S. Lanker, J. L. Bushman, A. G. Hinnebusch, H. Trachsel, P. P. Mueller, Cell 70:647–657, 1992).

In the absence of the GCN2 kinase, the General Control pathway, and hence the expression of GCN4 gene, cannot be activated by amino acid starvation. On the other hand, strains carrying mutations that partially inactivate a subunit of eIF-2 or eIF-2B are constitutively derepressed for GCN4 translation. In addition, small molecules that inhibit translation initiation or elongation will mimic the effect of serine-51-phosphorylated eIF-2alpha or mutations in eIF-2 or eIF-2B, and derepress GCN4 translation. Therefore, a strain lacking GCN2 and having a wild-type set of translational components eIF-2 and eIF-2B can be used to identify inhibitors of translation initiation, and possibly elongation, by monitoring the level of GCN4 expression in the cell. Furthermore, an inhibitor of a GCN4-responsive tRNA synthetase will be much more toxic in a cell lacking the GCN2 kinase.

A. Reporter Systems

Two types of reporters are used in this embodiment of the invention; namely, one type that can be monitored readily by enzyme assay, e.qf, a β-galactosidase gene fusion, and another type that can be monitored by the growth characteristics of the cell culture, e.g., growth in the absence of histidine. In each case the synthesis of the reporter should be designed to be as sensitive as possible to a translational inhibitor.

The advantages of assaying an enzyme such as β-galactosidase are well known. The readily available GCN4-lacZ fusion, which uses this reporter, shows a 10–50 fold regulation in response to amino acid limitation or mutation of GCD1, a translation initiation factor gene. In a more sensitive assay for test compounds, a CYC1-lacZ fusion with two copies of the GCN4 binding site in place of the CYC1 UAS1-UAS2 sequence shows a 20–200 fold regulation under the same conditions, and may show even greater regulation with more than two copies of the GCN4 binding site (A. G. Hinnebusch, G. Lucchini, and G. Fink, PNAS, 82: 498–502, 1985). The latter fusion is constructed using the plasmid pCM83 (Association of RAP1 Binding Sites With Stringent Control of Ribosomal Protein Gene Transcription in *Saccharomyces cerevisiae*, C. M. Moehle and A. G. Hinnebusch, Mol. Cell. Biol. 11: 2723–2735, 1991) and a complementary pair of oligonucleotides, 5'-TCG ACT GAC TCA CGT TTT TGT CGA CTG ACT CAC GTT TTT GCT CGA GTG TCT GTC A (SEQ. ID. NO.: 1) and 5'-GAT CTG ACA GAC ACT CGA GCA AAA ACG TGA GTC AGT CGA CAA AAA CGT GAG TCA G (SEQ. ID. NO.: 2), which, when annealed together, contain two GCN4 binding sites. This pair of oligonucleotides is cloned into the XhoI-BglII sites of pCM83, resulting in a lost XhoI site, one GCN4 site, a SalI restriction site, a second GCN4 site, a new XhoI site, and a reconstructed BglII site, going from the 5' end to the 3' end relative to the lacZ ORF. The same oligonucleotide pair is cloned again into the SalI-BglII sites of the new plasmid to add one more GCN4 site (net), or into the XhoI-BglII sites to add two more GCN4 sites. Choice of the optimum configuration (constructs with 2, 4, or 6 GCN4 binding sites) is determined by testing each construct for β-galactosidase activity in a gcn2 deletion strain (repressing condition) and a gcn2 gcd1 strain (derepressing condition), as well as in the former strain in the presence of known translation inhibitors.

The second type of reporter assay monitors the growth characteristics of the cell culture. In one embodiment, the endogenous HIS3 gene is used as the reporter. Expression of HIS3, and hence growth-resistance to 3AT, increases with increasing GCN4 gene expression. In the more preferred embodiment, the his1-29 gene is used as the reporter. A strain lacking the GCN2 kinase and having his1-29 substituted for the wild-type HIS1 gene cannot synthesize sufficient histidine for growth. Impairment of translation by genetic mutation, such as gcd1 or qcd2, or by the addition of translation inhibitors, such as anisomycin and T-2 toxin, results in increased translation of the GCN4 protein, which in turn results in increased transcription of his1-29 (and other histidine-biosynthetic genes), such that the cell makes sufficient histidine for growth. In some strain backgrounds, this latter assay works better if an empirically-derived, low concentration (ca. 10 μM, final) of histidine is added to the medium.

Other reporters could be used for this assay, including, but not limited to, modified forms of the HIS3 gene, genes encoding enzymes for which inhibitors are available, and genes encoding enzymes that inactivate an inhibitor.

B. Test Strains

The purpose of this screen method is to find compounds that derepress GCN4 expression because they inhibit translation. If a strain with wild-type GCN2 gene were used, compounds that do not inhibit translation but do activate GCN2 (the eIF-2alpha kinase) would also be detected by the screen because the activated GCN2 would derepress GCN4. Use of mutant strains lacking a functional GCN2 gene eliminates this complication. In the preferred embodiment, test strains used for the growth assay should also contain the his1-29 allele, which encodes a partially defective HIS1 protein. The his1-29 mutant can grow on medium lacking histidine in a Gcn+ background, but not in a Gcn− background. The haploid strain YRG130, which has the relevant genotype his 1-29 gcn2::LEU2 GCN4, is used for the screen in the next section.

Strains used for the enzyme expression assays preferably have a reporter gene fusion, such as HIS4-lacZ, GCN4-lacZ, or CYC1-lacZ (with GCN4 binding sites in place of the CYC1 UAS1 and UAS2 sequences).

C. Screening for Antifungals

Referring to FIG. 3, in order to identify potential therapeutics from a library of compounds, a culture of strain YRG130 (his 1-29 gcn2 GCN4) is prepared and seeded on Paradoxical Medium 1 (described below), after which candidate compounds are applied and their impact on growth is evaluated. The first step in this process is to grow the strain overnight at 30° C. with agitation in 2 ml YEPD (1% yeast extract, 2% peptone, 2% dextrose) broth. This starter culture is pelleted by centrifugation, washed in 4 ml sterile deionized water, and resuspended in 34 ml sterile, deionized water. Sixteen ml of the washed and resuspended culture is spread across the surface of a 10 in. square plate containing 250 ml Paradoxical Medium 1. Immediately after spreading, as much of the excess liquid as possible is removed by aspiration; the remaining excess liquid is dried by incubating the plate, with the lid removed, for 45–90 minutes in a biosafety cabinet with the blower operating. After drying, 2.5 mm diameter pins are pushed into the medium to make wells into which 2–4 μl of test compounds are pipetted. As would be obvious to those skilled in the art, application of the test compound in this manner will result in a concentration gradient being formed, with the highest concentration being close to the well. This method of assay therefore tests a range of test-compound concentrations with each application. The plates are incubated at 30° C. for 1–4 days (typically 2 days). During this time, growth of the lawn is monitored. In the absence of test compounds, the lawn will grow only slightly or not at all. In the presence of some inhibitors of translation, such as the model compound anisomycin, which inhibits peptidyltransferase activity (cited in: Effect of Fungicides on Protein Synthesis, M. R. Siegel, pp.399–428, in: *Antifungal Compounds* (Vol. 2) M. R. Siegel and H. D. Sisler, eds., Marcel Dekker, Inc.: N.Y., 1977), or cycloheximide, which inhibits more than one step in translation (ibid.), there is a ring of no growth surrounding the disk because translation is completely inhibited. Surrounding the ring of no growth is a zone of stimulated growth, where there is a balance of partial translational inhibition: a sufficient reduction in translation to cause derepression of GCN4 expression and increased histidine synthesis, yet still enough residual translation for the cell to continue growing and dividing. In the presence of a compound that kills yeast via a non-translation target, such as canavanine or 10% SDS (sodium dodecyl sulfate), the disk is surrounded by a ring of no growth, but not by another concentric ring of stimulated growth.

Interesting compounds identified by this protocol are screened secondarily by the analogous assay with an otherwise isogenic gcn2 his1-29 gcn4 strain, YRG129, which was constructed by standard methods well known to those skilled in the art. In the absence of the GCN4 protein, the putative translational inhibitor can still restrict growth in the first zone, but can no longer stimulate growth in the second zone. Compounds that inhibit a tRNA synthetase (e.g., borrelidin) or an amino acid biosynthetic enzyme (e.g., 3AT), both of which provide substrates for translation in vivo, are identified by being much more potent against the Gcn− strain than the Gcn+ strain. The secondary assay with strain YRG129 is performed by the same protocol described for the primary assay with YRG130, except that Paradoxical Medium 1 is replaced by Paradoxical Medium 2. YRG129 requires more histidine for growth than does YRG130, due to the absence of the GCN4 protein.

The recipes for Paradoxical Medium 1 and Paradoxical Medium 2 are given below.

| Paradoxical Medium 1 | | |
|---|---|---|
| 5.0 | g | Bacto Agar |
| 1.68 | g | Difco yeast nitrogen base without amino acids |
| 0.25 | ml | 200 mM inositol |
| 1.25 | ml | 100 mM arginine |
| 5.0 | ml | 10 mM uracil |
| 7.5 | μl | 100 mM histidine |
| 230 | ml | distilled water |
| autoclave for 30–40 minutes, add: | | |
| 12.5 | ml | 40% dextrose |
| cool to 55° C. and pour all into (1) 25 cm × 25 cm sterile culture dish (e.g., Stratagene #400040) | | |
| Paradoxical Medium 2 | | |
| 5.0 | g | Bacto Agar |
| 1.68 | g | Difco yeast nitrogen base without amino acids |
| 0.25 | ml | inositol stock |
| 1.25 | ml | arginine stock |
| 5.0 | ml | uracil stock |
| 75 | μl | histidine stock |
| 230 | ml | distilled water |
| autoclave for 30–40 minutes, add: | | |
| 12.5 | ml | 40% dextrose |
| cool to 55° C. and pour all into (1) 25 cm × 25 cm sterile culture dish (e.g. Stratagene #400040) | | |

D. Enzyme Assay

In order to identify potential therapeutics from a library of compounds, a starter culture of the appropriate strain (a gcn2 strain with a GCN4-lacZ reporter gene in the current embodiment) is grown overnight in SD medium supplemented for auxotrophies (Guide to Yeast Genetics and Molecular Biology, C. Guthrie and G. Fink, eds. Methods in Enzymology, Vol. 194, 1991) and diluted 1:50 into the same medium. After the cells have resumed growing (2–4 hrs), the test compound is added at a concentration that limits, but does not absolutely stop, growth. Most preferably, the compound causes a three-fold increase in the cell doubling time, which is preferably measured by assaying the accumulation of total cell protein, and less preferably measured by determining the light-scattering property of the liquid culture. If the test compound causes a less than two-fold increase in the doubling time, it may score as a false negative because it is not at a high enough concentration, and would need to be assayed again at a higher concentration. If the compound causes a greater than five-fold increase in the doubling time, it may score as a false negative because all translation has been shut off too efficiently to observe a change in translational regulation, and would need to be assayed at a lower concentration. After an additional 5–6 hrs, the cultures are harvested and the activity of the reporter gene is assayed by methods well known to those skilled in the art (Association of RAP1 binding sites with stringent control of ribosomal protein gene transcription in *Saccharomyces cerevisiae*, C. M. Moehle and A. G. Hinnebusch, Mol. Cell. Biol. 11: 2723–2735, 1991, and references therein). The reporter activity is compared to a parallel culture that has not been treated with the compound.

A compound that inhibits translation will stimulate GCN4-lacZ expression and lead to significantly higher β-galactosidase activity. Interesting compounds that are identified by this protocol are screened secondarily by the analogous assay using an otherwise isogenic strain bearing GCN4-lacZ and GCN4 alleles with only the fourth upstream open reading frame (ORF) in the MRNA leader; this allele cannot respond to the translational control mechanism and therefore should not respond to the translational inhibitor (Protein Synthesis and Translational Control, A. G. Hinnebusch and S. W. Liebman, pp.626–736, in: *The Molecular Biology of the Yeast Saccharomyces*, J. R. Broach, J. R. Pringle, and E. W. Jones, eds., CHS Laboratory Press: N.Y., 1991).

4. Phenotypic Relaxation Assay

The invention features a method for screening for an antifungal agent, where particular yeast genes exhibiting transcriptional regulation that is sensitive to the translational capability of the cell are identified and used as indicators of test compound activity. Expression of these genes may be used to directly report test compound activity, either by measuring their gene products directly, by in vivo or in vitro assay, or by fusing their regulatory elements to suitable reporter genes and measuring production of the hybrid gene product in vivo or in vitro. Alternatively, the expression of the translational indicators may be used to drive expression of other genes that in turn function as the reporters of test compound activity.

This method utilizes a fungal translation-responsive transcriptional control nucleic acid sequence that allows increased transcription (and subsequent translation) of a specific RNA or RNAs under translation-inhibiting conditions. In the preferred embodiment, the sequence is transcriptionally linked to a gene encoding a reporter polypeptide. The method then further includes contacting a yeast cell or cell extract containing the sequence with a potential antifungal agent under conditions which allow littl'e or no synthesis of the reporter polypeptide in the absence of the agent. The method finally includes determining whether the agent increases the level of synthesis of the reporter polypeptide. Paradoxically, any agent that does increase this level is potentially useful as an antifungal agent, albeit at higher doses.

Alternatively, this method utilizes a bacterial translation-responsive transcriptional control nucleic acid sequence that allows increased transcription (and subsequent translation) of a specific RNA or RNAs under translation-inhibiting conditions. In the preferred embodiment, the sequence is transcriptionally linked to a gene encoding a reporter polypeptide. The method then further includes contacting a bacterial cell or cell extract containing the sequence with a potential antifungal agent under conditions which allow little or no synthesis of the reporter polypeptide in the absence of the agent. The method finally includes determining whether the agent increases the level of synthesis of the reporter polypeptide. Paradoxically, any agent that does increase this level is potentially useful as an antifungal agent, albeit at higher doses.

In the more preferred embodiment, referred to as the "Phenotypic Relaxation Assay", phenotypic relaxation (D. H. Ezekiel and B. N. Elkins, Biochim. Biophys. ACTA 166: 466–474, 1968) of the yeast stringent response (K. J. Gross and A. O. Pogo, Biochem. 15:2082–2086, 1976) is used to identify translation blockers (see FIG. 4). By analogy to bacteria (The Stringent Response, M. Cashel and K.E. Rudd, in: *Escherichia coli and Salmonella typhimurium, Cellular and Molecular Biolocy*, F. C. Neidhardt, ed., American society for Microbiology:Washington, D.C., 1987, and references therein), and in part by independent confirmation with yeast, it is known that amino acid starvation in yeast normally results in an increase in the ratio of uncharged-to-charged tRNA levels, which is recognized by the translating ribosome, which is believed to generate a starvation signal that in turn causes a decrease in the rate of synthesis of ribosomal RNAs and proteins ("stringent response"). Test compounds that inhibit translation will reduce the demand on aminoacyl tRNA pools, thereby offsetting the effect of amino acid starvation by blocking the generation of the starvation signal and causing partial restoration of synthesis of ribosomal proteins.

Thus, the level of synthesis of a ribosomal protein, such as the product of the gene RPL16A, can be used to monitor test compound activity. Although the ribosomal protein may itself be used as a reporter, the regulatory elements of RPL16A are fused to the 5' end of a suitable reporter gene or portion thereof in the preferred embodiment, and expression of this genetic hybrid can be used to detect protein synthesis inhibitors under conditions of partial amino acid starvation. More specifically, this translation-blocker-assay uses: a) 3-amino-1,2,4-triazole, a well-known inhibitor of imidazole-glycerolphosphate dehydrogenase, which is encoded by the *S. cerevisiae* HIS3 gene, to cause limitation for the amino acid histidine, thereby evoking the stringent response and also inhibiting yeast growth on minimal or supplemented medium lacking histidine, and b) the HIS3 gene fused as a reporter gene to the RPL16A regulatory elements. Paradoxically, at a low dosage, a test compound that inhibits translation causes the 3AT-treated cells to synthesize more of the RPL16A-linked HIS3 protein, allowing the cells to overcome the 3AT-mediated growth inhibition, and grow in conditions under which they otherwise would grow very slowly or not at all. Alternatively, the HIS3-reporter can be replaced by another gene, such as the *E. coli* lacZ gene, that is readily assayed by methods well known to those skilled in the art.

The use of RPL16A HIS3 and RPL16A lacZ is given as an example only, and-Lin no way should be construed as limiting the present invention to the use of these genes and their products. Those skilled in the art will recognize other ribosomal genes as usful reporter genes.

By "fungal translation-responsive transcriptional control nucleic acid sequence" is meant any nucleic acid which allows increased transcription of a specific RNA or RNAs under translation-inhibitory conditions. Such nucleic acid is exemplified by the regulatory elements of the RPL16A gene which, under conditions of amino acid limitation, allow increased transcription of transcriptionally linked gene sequences upon introduction of a translational inhibitor.

By "transcriptionally linked" is meant that the members are part of a transcription unit, consisting of (1) control elements, which determine the timing, frequency, and position of transcription initiation, as well as the position of transcription termination, and (2) transcribed sequences, i.e., the DNA sequences which are transcribed into RNA. Note that the sequences of a transcription unit may be separated by other DNA sequences that are not part of the unit. Furthermore, in many instances, the spacing of the members of the unit is also important for proper function.

By "increased transcription" is meant that the mRNA is transcribed at a higher rate or with higher yield, relative to total mRNA synthesis or yield, under translation-inhibitory conditions when compared to the rate or yield under non-translation-inhibitory conditions. In addition, the average of total cell mRNAs may be transcribed at a slower rate or with lower RNA yield than in non-translation-inhibitory conditions. Such alterations in transcription can be readily detected as described below.

By "stringent response" is meant the regulatory response of a microbial cell during conditions of amino acid limitation. Many aspects of cellular metabolism are affected, but the effect most salient to this application is a specific reduction in the transcription of many yeast genes encoding translational components.

By "relaxation of the stringent response" is meant the full or partial reversal of the effects of the stringent response, i.e., transcription of translational component genes is either unaffected, or is affected to a lesser extent, during conditions of amino acid limitation.

By "phenotypic relaxation of the stringent response" is meant a relaxation of the stringent response due to an environmental condition, such as the addition of a translational inhibitor, as opposed to a relaxation of the stringent response due to a genetic mutation.

EXAMPLE 2

Monitoring RPL16A Expression

Microorganisms use the stringent control pathway for monitoring and responding to intracellular amino acid levels. As a consequence of amino acid limitation, the cell experiences an increase in uncharged tRNA levels, in response to which it generates a starvation signal that causes a reduction in the synthesis of ribosomal constituents. In bacteria it is known that the ribosomeassociated factor RelA monitors the ribosomal A-site. When the ribosome stalls at a codon because the cognate amino-acylated tRNA is not available, RelA synthesizes the second messenger ppGpp. The intracellular concentration of ppGpp is inversely proportional to the synthesis rate of ribosomal constituents. If an inhibitor of elongation, such as chloramphenicol, is added to amino-acid-starved cells at sublethal concentrations, charged tRNAs are not consumed as quickly. Therefore, the ribosome does not stall as often, RelA does not synthesize as much ppGpp, and the synthesis of ribosomal constituents is not reduced as much. This latter phenomenon is known as phenotypic relaxation of the stringent response (D. H. Ezekiel and B. N. Elkins, Biochim. Biophys. ACTA 166: 466–474, 1968). The yeast Saccharomyces has been shown to have a stringent response much like bacteria, including the phenomenon of phenotypic relaxation, although less is known in yeast and cognates for RelA and ppGpp have not been identified (Association of RAP1 Binding Sites With Stringent Control of Ribosomal Protein Gene Transcription in *Saccharomyces cerevisiae*, C. M. Moehle and A. G. Hinnebusch, Mol. Cell. Biol. 11: 2723–2735, 1991, and references therein). Therapeutics that inhibit translation in yeast could be identified by observing phenotypic relaxation. However, monitoring synthesis of ribosomal constituents directly would be too cumbersome for large-scale applications. This invention describes a method for identifying anti-fungal agents that inhibit translation elongation, and possibly initiation, by monitoring phenotypic relaxation of the stringent response with gene fusions.

A. Reporter Systems

Two types of reporters are used in this embodiment of the invention; namely, one type that can be monitored readily by enzyme assay, such as a β-galactosidase gene fusion, and one type that can be monitored by the growth characteristics of the cell culture, e.g., growth in the absence of histidine. In each case the synthesis of the reporter should be designed to be as sensitive as possible to a translational inhibitor.

The advantages of assaying an enzyme such as β-galactosidase are well known. The readily available RPL16A-lacZ fusion, which uses this fusion, shows a 4–6 fold regulation in response to amino acid limitation. If a more sensitive assay for test compounds is required, a derivative of the RPL16A-lacZ fusion can be used in which part or all of the presumptive unregulated, or basal, transcriptional T-rich element is replaced with 2–4 extra copies of the stringent-control-responsive RAP1-binding sites.

The latter fusion is constructed by first ligating the double-stranded L16 oligonucleotide (Association of RAP1 Binding Sites With Stringent Control of Ribosomal Protein Gene Transcription in *Saccharomyces cerevisiae*, C. M. Moehle and A. G. Hinnebusch, Mol. Cell. Biol. 11: 2723–2735, 1991), which has the two RAP1-binding sites derived from RPL16A bracketed by a BqlII-compatible end and an XhoI-compatible end, to itself, and cloning the dimer into the SalI site of pRS306 (A System of Shuttle Vectors and Yeast Host Strains Designed for Efficient Manipulation of DNA in *Saccharomyces cerevisiae*, R. S. Sikorski and P. Hieter, Genetics 122:19–27, 1989). Since XhoI and SalI restriction fragments can be ligated together to create a hybrid site not recognized by either enzyme, this cloning step will create a plasmid with a pair of L16 oligonucleotides that are joined at the BqlII end. This dimer can be excised, by cleaving the plasmid at the XhoI and BamHI sites that bracket the original SalI site, and then ligated into the XhoI-BqlII sites of pCM54 (Association of RAP1 Binding Sites With Stringent Control of Ribosomal Protein Gene Transcription in *Saccharomyces cerevisiae*, C. M. Moehle and A. G. Hinnebusch, Mol. Cell. Biol. 11: 2723–2735, 1991). (Note that the relationship between SalI and XhoI is also true between BamHI and BglII.)

The second type of reporter, i.e., one that can be monitored by the growth characteristics of the cell culture, uses a gene encoding a product that can be inhibited by an externally supplied reagent. The HIS3 gene, which encodes imidazoleglycerolphosphate dehydrogenase, is used as the reporter, and 3-amino-1,2,4-triazole (3AT) is used as the inhibitor as described below. An RPL16A-HIS3 fusion was constructed and introduced into an appropriate yeast strain (his3 gcn4) by the method described below. The native HIS3 gene was removed, as described below, to eliminate background activity, and the GCN4 gene was removed in order to clamp the expression of other genes in the histidine pathway at a constant level, since most or all of them are responsive to GCN4 levels, which would fluctuate in response to 3AT (see, FIG. 2). At a minimally inhibitory concentration (MIC) of 3AT, expression of the RPL16A-HIS3 fusion decreases, due to the stringent response to amino acid limitation, and the culture does not grow.

Referring to FIGS. 6A and 6B, if an inhibitor of translation elongation, such as cycloheximide, is added to the 3AT MIC-treated culture, the starvation signal to repress the RPL16A promoter is attenuated, the cell synthesizes more RPL16A-HIS3 and grows. Other promoters could be used for this assay, including, but not limited to, modified forms of the promoter for the RPL16A gene and other promoters, native or recombinant, for genes that respond to amino acid limitation as described here for RPL16A.

By "MIC" is meant minimum inhibitory concentration.

B. RPL16A-HIS3 and CYC1-HIS3 fusion genes

A DNA fragment containing the entire HIS3 ORF was amplified by the PCR method from the larger HIS3 fragment in plasmid YIp1 using two oligonucleotides of sequence 5'-CG-AAG-gga-tcc-ATG-ACA-GAG-CAG-AAA-GCC (SEQ. ID. NO. 3) and 5'-ACC-ACT-gtc-gac-CTA-TCA-CCA-CAA-CTA-ACT (SEQ. ID. NO. 4), where the lowercase sequence denotes introduced BamHI and SalI restriction sites, respectively. The BamHI restriction site is immediately 5' of the ATG initiation codon and the SalI restriction site is 154 bp 3' of the termination codon of the HIS3 ORF. This fragment was cleaved with BamHI and SalI, and cloned into the BamHI and SalI restriction sites of pRS306 (A System of Shuttle Vectors and Yeast Host Strains Designed for Efficient Manipulation of DNA in *Saccharomyces cerevisiae*, R. S. Sikorski and P. Hieter, Genetics 122:19–27, 1989). A 1.1 kb BamHI fragment containing the promoter, transcription start sites, and the first 49 codons of the ORF of RPL16A from the RPL16A-lacZ fusion described above was then cloned into the BamHI site in the proper orientation to make an RPL16A-HIS3 fusion gene. The DNA sequence of the two ends of the HIS3 fragment was verified by methods well known to those skilled in the art. Subsequently, the URA3 gene contained on this plasmid was disabled by digesting the plasmid with the restriction enzymes NcoI and AatII, followed by incubation with the Klenow fragment of *E. coli* DNA polymerase I plus dNTPs, followed by incubation with T4 DNA ligase.

The resulting plasmid retains a fragment of the URA3 gene which can be used to target integration to the URA3 locus via homologous recombination. The CYC1-HIS3 fusion was made by replacing the BamHI-StuI fragment of the RPL16A-HIS3-containing plasmid with the analogous fragment from pCM61 (Association of RAP1 Binding Sites With Stringent Control of Ribosomal Protein Gene Transcription in *Saccharomyces cerevisiae*, C. M. Moehle and A. G. Hinnebusch, Mol. Cell. Biol. 11:2723–2735, 1991).

C. Test Strains

This assay makes it possible to discover translational inhibitors by screening for compounds that block repression of RPL16A expression during amino acid limitation. The screen is designed so that the yeast strain cannot grow except in the presence of an inhibitor of translation. In the preferred embodiment, the screen requires a yeast strain with the genotype his3-609 RPL16A-HIS3 gcn2 RPL16A-lacZ. The HIS3 gene is deleted to facilitate the use of the RPL16A-HIS3 selectable reporter gene. The his3-609 allele is preferred because this allele is lacking nearly the entire ORF (609 bp), and the deletion does not extend beyond the ORF. Similar alleles could be used as long as the deletion does not extend into important regulatory domains for the adjacent PET56 and DED1 genes. The his3-609 allele was made by transforming a HIS3 ura3 yeast strain with an 84-residue synthetic oligonucleotide (5'-G-CAG-GCA-AGA-TAA-ACG-AAG-GCA-AAG-atg-ACA-GAG-CAG-AAA-GCC-C/AT-GTT-CCC-TCC-ACC-AAA-GGT-GTT-CTT-ATG-tag-TGA-CAC-CG (SEQ. ID. NO.: 5), where the initiation and termination codons are in lower case, and the location of the deletion is indicated with a slash) annealed to its complement along with the episomal, URA3-containing plasmid YEp24.

The Ura+ transformants were then screened for His– mutants. The chromosomal deletion was confirmed by DNA blotting/hybridization methods well known to those skilled in the art. The GCN2 gene is deleted to facilitate the use of the RPL16A-HIS3 selectable reporter gene because strains having an intact general control pathway will derepress several steps of histidine biosynthesis during the amino acid limitation caused by 3AT. This variable metabolic flux through the pathway reduces the impact of the RPL16A-HIS3-encoded step on growth. A different gcn mutation, such as gcn4, could be used for this screen. The gcn2 mutation, however, has two advantages. First, since the GCN2 protein acts at or near the top of the general control pathway, compounds that activate GCN4 expression, as outlined above, will be identified because they induce growth on the 3AT medium. Second, a gcn2 mutant will have a constitutive low level of GCN4 expression, whereas a gcn4 mutant by definition has no GCN4 expression. In this embodiment, the low-level constitutive GCN4 expression causes the RPL16A-HIS3-encoded step to become even more rate-limiting for histidine synthesis and the sensitivity of the screen is further enhanced.

D. Growth Assay

In order to identify potential therapeutics from a large library of compounds, a starter culture of the appropriate strain (RPL16A-HIS3 his3 gcn4; an otherwise isogenic CYC1-HIS3 gcn2 strain lacking the RPL16A-HIS3 gene is used in parallel as a control) is lightly seeded onto a 100 mm diameter Petri plate of the appropriate yeast medium (given below) by transferring ca. 2 ml of the culture onto the plate and swirling it for 2 minutes before removing the excess liquid. The plates are allowed to dry for one to several hours on a level surface before filter disks that have been (or will be) impregnated with a high dose of the test compounds are placed on the surface of the medium. Ten microliters of a concentrated stock solution of the test compound is added to each disk immediately after placing it on the cell lawn, unless the solution was applied earlier. As would be obvious to those skilled in the art, application of the test compound in this manner will result in a concentration gradient being formed, with the highest concentration being close to the disk. This method of assay therefore tests a range of test-compound concentrations with each application. The plates are then incubated at 30° C. for 1–4 days (typically 2 days), and the growth of the lawn is monitored. In the absence of test compounds, the lawn will grow only slightly or not at all.

Referring again to FIGS. 6A and 6B, in the presence of some inhibitors of translation, such as anisomycin, cycloheximide, G418, hygromycin B, and T-2 toxin, there is a ring of no growth surrounding the disk because translation is completely inhibited. Surrounding the ring of no growth is a zone of stimulated growth, where there is a balance of partial translational inhibition with a reduction in translation sufficient to block repression of RPL16A expression and cause increased histidine synthesis, yet sufficient residual translation to allow the cell to continue growing and dividing. Similar results were obtained in the presence of other inhibitors of translation, such as gentamycin, gougerotin, and puromycin, except that no zone of growth inhibition was observed.

For compounds that kill yeast but do not target translation (e.g., canavanine, 0.5M EDTA, and 10% SDS), the disk is surrounded by a ring of no growth, but not by a second concentric ring of stimulated growth. To eliminate false positives, interesting compounds identified by this protocol are screened again by the analogous assay with an otherwise isogenic strain bearing a CYC1-HIS3 fusion and lacking the RPL16A-HIS3 fusion, which was constructed by standard methods well known to those skilled in the art. In the latter strain, a translational inhibitor can still restrict growth in the first zone, but can no longer stimulate growth in the second zone.

E. Medium for Assay

The following mixtures were prepared in separate flasks:

| Flask 1 | | |
|---|---|---|
| 1.7 | g | Difco yeast nitrogen base w/o amino acids and ammonium sulfate |
| 5.0 | g | ammonium sulfate |
| 20.0 | g | Bacto agar |
| 420 | μl | distilled or deionized water |
| Flask 2 | | |
| 0.1 | g | of each amino acid, except histidine and tryptophan |
| 0.3 | g | leucine |
| 0.1 | g | uracil |
| 0.1 | g | inositol |
| 0.05 | g | adenine |
| 0.01 | g | para-aminobenzoic acid |
| 1.0 | ml | 1 M 3AT stock solution (in water, filter, store at −20° C.) |
| 500 | ml | distilled or deionized water |

Flasks 1 and 2 are autoclaved separately, mixed, and the following are added: 50 ml 40% dextrose stock and 10 ml 40 mM tryptophan stock (filter sterilized and stored at 4° C. in the dark). The combined medium is cooled to 55° C. and poured into sterile dishes.

F. Enzyme Assays

In order to identify potential therapeutics from a library of compounds, a starter culture of the appropriate strain (e.g., a gcn2 strain with an RPL16A-lacZ reporter gene in the current embodiment) is grown overnight in synthetic minimal medium (2% dextrose, 0.5% ammonium sulfate, 1.7 g/l Difco yeast nitrogen base w/o amino acids and ammonium sulfate) supplemented for auxotrophies (*Laboratory Course Manual for Methods in Yeast Genetics*, F. Sherman, G. R. Fink, and J. B. Hicks, Cold Spring Harbor Laboratory: N.Y., 1986) and diluted 1:50 into the same medium. After the cells have resumed growing (2–4 hrs), the test compound is added at a concentration that limits, but does not absolutely stop, growth. Preferably the compound causes a three-fold increase in the cell doubling time, which is preferably measured by assaying the accumulation of total cell protein, and less preferably measured by determining the light-scattering property of the liquid culture. If the test compound causes a less than two-fold increase in the doubling time, it may score as a false negative because it is not at a sufficient high concentration, and would need to be assayed again at a higher concentration. If the compound causes a greater than five-fold increase in the doubling time, it may score as a false negative because all translation has been shut off too efficiently to observe a change in translational regulation, and would need to be assayed at a lower concentration.

After an additional 5–6 hrs, the cultures are harvested and the activity of the reporter gene is assayed by methods well known to those skilled in the art (Association of RAP1 binding sites with stringent control of ribosomal protein gene transcription in *Saccharomyces cerevisiae*, C. M. Moehle and A. G. Hinnebusch, Mol. Cell. Biol. 11: 2723–2735, 1991, and references therein). The reporter activity is compared to a parallel culture that has not been treated with the compound.

A compound that inhibits translation will stimulate RPL16A-lacZ expression and lead to significantly higher activity. To verify that interesting compounds that are identified by this protocol are acting specifically against translation, such compounds are screened secondarily by the analogous assay using an otherwise isogenic strain bearings a CYC1-lacZ fusion. This fusion cannot respond to the Stringent Control mechanism (Association of RAP1 Binding Sites With Stringent Control of Ribosomal Protein Gene Transcription in *Saccharomyces cerevisiae*, C. M. Moehle and A. G. Hinnebusch, Mol. Cell. Biol. 11: 2723–2735, 1991) and therefore should not respond to the translational inhibitor.

5. Translation-component Specific Assay

It is known that some steps of translation are sensitive to the stoichiometry of different components based on the phenotypes of certain mutant yeast cells. For example: 1) increased gene dosage of YEF3, which encodes EF-3, leads to increased sensitivity to drugs that interfere with translational accuracy (M. G. Sandbaken, J. A. Lupisella, B DiDomenico, and K. Chakraburtty, J. Biol. Chem. 265: 15838–15844, 1990); 2) increased gene dosage of SUI3 or GCD11, which encode eIF-2β and eIF-2gamma, respectively, leads to increased translation of GCN4, which is indicative of decreased efficiency of translational initiation; increased gene dosage of SUI2, which encodes eIF-2alpha, does not have any measurable effect; 3) partial or complete depletion of the GCN3-encoded protein, a non-essential subunit of eIF-2B, makes eIF-2B less sensitive to inhibition by phosphorylated eIF-2alpha (Protein Synthesis and Translational Control, A. G. Hinnebusch and S. W. Liebman, pp.626–736, in: *The Molecular Biology of the Yeast Saccharomyces*, J. R. Broach, J. R. Pringle, and E. W. Jones, eds., CSH Laboratory Press: N.Y., 1991).

These and other related observations suggest that overexpression or underexpression of any translation component or subunit could lead to altered sensitivity to an inhibitor of a relevant step in translation. In one case, a therapeutic could be an inhibitor of a given step or steps of translation. Such an inhibitor should be more potent against a cell or cell extract limited by a deficiency in the macromolecule catalyzing that step or steps, and/or less potent against a cell or cell extractcontaining an excess of said macromolecule, as compared to the wild-type cell or cell extract. In a second case, a therapeutic could be a type of pro-drug that is transformed from a benign to a toxic form by a macromolecule that normally catalyzes one or more steps in the translation pathway. Such a compound should be less potent against a cell or cell extract limited by deficiency in the macromolecule catalyzing that step or steps, and/or more potent against a cell or cell extract containing an excess of said macromolecule, as compared to the wild-type cell or cell extract. In a third case, a therapeutic could stimulate a macromolecule normally involved in translation to catalyze a reaction which is harmful when catalyzed in excess of the level catalyzed in the absence of said therapeutic. Such a compound should be less potent against a cell or cell extract limited by deficiency in the macromolecule catalyzing that step or steps, and/or more potent against a cell or cell extract containing an excess of said macromolecule, as compared to the wild-type cell or cell extract.

Thus, the invention features a method for screening for an antifungal agent utilizing mycotic cell systems that are sensitive to perturbation to one or several translational components.

In a preferred embodiment, referring to FIG. 8, the method includes providing a battery of yeast mutant strains derived from an isogenic background. Each strain differs from the others and the wild-type strain only by mutation(s) in a gene(s) encoding a translational component(s). Genes for these or for any macromolecule specifically required for translation can be obtained by several methods, such as, but not limited to, cloning by complementation of the relevant mutation with genomic plasmid libraries, screening an expression library with an antibody that recognizes the macromolecule, or screening a genomic plasmid or phage library by hybridization with labeled DNA or RNA sequences that are known to encode the macromolecule in yeast or another organism (Guide to Yeast Genetics and Molecular Biology, C. Guthrie and G. Fink, eds. Methods in Enzymology, Vol. 194, 1991).

This method of drug discovery may involve a simple assay to detect binding of an agent to any component of the translation apparatus. Preferably, however, the battery of strains is screened for altered growth sensitivity to test compounds. A mutant strain that differs from wild-type because it has a mutation that either alters the level of a given translation component or alters its activity will show altered sensitivity to a drug that targets that component. In contrast, the same mutant or a wild-type control will display wild-type sensitivity when challenged with test compounds that do not interact with this target. This same set of strains also is used to make a set of cell extracts for the purpose of in vitro translation, where it follows that each extract differs only in the amount or activity of a single protein or RNA that participates in translation. In general, the potency of a translational inhibitor that targets a specific step will be inversely proportional to the effective concentration of its target. In some cases however, a translation-based therapeutic will have the opposite effect; its potency will be directly proportional to the effective concentration of its target, insofar as its molecular target participates in generating the compound's therapeutic effect.

In a less preferred embodiment of this assay, not all members of the bank of strains would be from the same isogenic background. With this method it is possible to develop both a whole-cell assay and a simplified cell-extract assay that can be tailored to target any macromolecule required for protein synthesis. This assay not only can be used to discover potential translational-component-specific drugs, but also can be used to identify the specific target of translational inhibitors whose precise molecular target was not previously known.

By "screening" is preferably meant a process in which a large number of potentially useful agents are processed. It is a process distinct from a single experiment in which a single agent is studied in detail to determine its method of action.

By "large number" in the previous paragraph is meant more than twenty, or preferably more than a hundred, potentially useful agents.

By "antifungal" is meant a compound that has the effect of either killing or significantly slowing the growth of an organism commonly referred to as a fungus, including, but not limited to, fungi that can be pathogenic to humans.

By "yeast" is preferably meant *Saccharomyces cerevisiae*, although other yeasts or fungal organisms may be used.

By "wild-type yeast" is meant a yeast strain defined, in part arbitrarily, as being the standard or control for a given set of experiments. A wild-type strain may have one or more "mutations" in genes that are not deemed relevant to the experiments at hand, e.g., a strain carrying a leu1 mutation, conferring a requirement for leucine, may still be considered "wild-type" for the purpose of examining translation, but not for the purpose of examining leucine biosynthesis.

By "mutant yeast" is meant a yeast strain differing from the defined wild-type at one or more known or unknown genes or genetic loci. The genetic differences may be of several different types, including, but not limited to, point mutations where a single base pair is changed to one of the three other possible base pairs, an insertion of one or more base pairs, a deletion of one or more base pairs up to the full length of the locus, fusion of one gene to another, introduction of additional copies of an existing gene, introduction of one or more copies of a new gene not formerly present, or any combination of the above.

By "isogenic background" is meant "genetically uniform" (*A Dictionary of Genetics*, second edition, revised. R. C. King, Oxford University Press: New York, 1976). In other words, an isogenic background means that there are no known genetic differences between members of the set of strains or organisms, except for those explicitly specified. In the present definition, this can only be achieved by some forms of DNA transformation experiment, several of which are well known to those skilled in the art. The genetic difference may be one of several different types, including, but not limited to, point mutations where a single base pair is changed to one of the three other possible base pairs, an insertion of one or more base pairs, a deletion of one or more base pairs even up to the full length of the locus, fusion of one gene to another, introduction of additional copies of an existing gene, introduction of one or more copies of a new gene not formerly present, or any combination of the above.

By "translational component" is meant a gene product, either protein or nucleic acid, which is known or believed to be involved in the process of translation, including, but not limited to, aminoacyl-tRNA synthetases, translational initiation factors, such as, but not limited to, those listed in Mechanism and Regulation of Eukaryotic Protein Synthesis, William C. Merrick, Microbiological Reviews 56:291–315, 1992, or J. Hershey, Ann. Rev. of Biochem. 60:717–755, 1991, translational elongation factors, such as, but not limited to, those listed in ibid., translational termination factors (also known as release factors), such as, but not limited to, those listed in ibid., proteins that can act as omnipotent suppressors, such as, but not limited to, proteins encoded by the genes SUP35 and SUP45 and their synonyms (Protein Synthesis and Translational Control, A. G. Hinnebusch and S. W. Liebman, pp.626–736, in: *The Molecular Biology of the Yeast Saccharomyces*, J. R. Broach, J. R. Pringle, and E. W. Jones, eds., CSH Laboratory Press: N.Y., 1991), proteins, the genes for which often are named SUP, SUF, or SAL, for which the precise function may not be known except that they affect the fidelity of translation, for example, but not limited to, those described, (ibid.), proteins for which the precise function may not be known except that they are required for efficient translation in vivo and may act by affecting protein-protein interactions, for example, but not limited to, the yeast SIS1 protein (T. Zhong and K. T. Arndt, Cell 73:1175–1186, 1993) and the 70 kd heat shock protein (R. J. Nelson, T. Ziegelhoffer, C. Nicolet, M. Werner-Washburne, and E. A. Craig, Cell 71:97–105, 1992), less well-defined proteins physically associated with ribosomes, but removable by a "salt wash", integral ribosomal proteins that comprise the large and small ribosomal subunits, ribosomal RNAs, tRNAs, signal recognition particle (SRP), any protein or RNA required for the translation of specific mRNAs, such as, but not limited to, PET494, PET122, and PET54, all of which are required for COXIII translation (Biogenesis of Yeast Mitochondria, L. Pon and G. Schatz, pp.333–406, in: *The Molecular Biology of the Yeast Saccharomyces*, J. R. Broach, J. R. Pringle, and E. W. Jones, eds., CSH Laboratory Press: N.Y., 1991; Diversity of mechanisms in the regulation of translation in prokaryotes and lower eukaryotes, L. Lindahl and A. Hinnebusch, Curr. Opin. in Gen. and Dev. 2:720–726, 1992), any protein or RNA required for the translational repression of specific mRNAs, such as, but not limited to, SKI2 protein (W. R. Widner and R. B. Wickner, Mol. Cell. Biol. 13: 4331–4341, 1993), and any protein or RNA that modifies any of the above named so as to change its activity in a measurable way, such as, but not limited to, ribonucleases, protein kinases and phosphatases, enzymes that modify RNA bases, enzymes that remove bases from polynucleotides, ADP ribosylating enzymes, enzymes that generate hypusine, enzymes that generate diphthamide, enzymes that generate selenocysteine or selenocysteine-containing polypeptides, enzymes that methylate or demethylate proteins or ribonucleic acids, components that increase or decrease the half-life of mRNAs (C. F. Higgins, S. W. Peltz and A. Jacobson, Curr. Opin. in Gen. and Dev. 2:739–747, 1992), such as, but not limited to, UPF1 protein (which promotes mRNA turnover in *Saccharomyces cerevisiae*, P. Leeds, J. M. Wood, B. S. Lee, and M. R. Culbertson, Mol. Cell. Biol. 12:2165–2177, 1992) and "dodecamer sequence-binding protein" (which binds to a dodecamer sequence found at the 3' ends of yeast mitochondrial mRNAs, J. Min and H. P. Zassenhaus, Mol. Cell. Biol. 13: 4167–4173, 1993), and enzymes that acetylate or deacetylate proteins or ribonucleic acids.

By "translational component" also is meant any gene product, either protein or nucleic acid, which can be added to an in vitro reaction with the result of stimulating translation, or any partial reaction of translation, preferably by a factor of 10 or greater, or less preferably, by a factor,of 2 or greater.

By "translational component" also is meant any gene product, either protein or nucleic acid, which can be altered and shown to affect translation in vivo, preferably by a factor of 10 or greater, or less preferably, by a factor of 2 or greater. This can be measured by its effect on synthesis of a translationally-regulated reporter protein, or by determining its effect on the quantity or status of any known translation component.

By "altered growth sensitivity" is meant either an increase or decrease in the growth rate of the mutant cell culture compared to a wild-type cell culture from an isogenic, or less preferably, from a similar, genetic background, as determined by protein or cell yield, as measured by methods known to those skilled in the art, such as by determinations of cell number, viable cell number, colony forming units, total cell mass, total cell protein, or turbidity, after a predetermined amount of time, typically 12 sours to 3 days. The altered growth sensitivity of the mutant results preferably in a greater than 10-fold difference, or less preferably a greater than 2-fold difference, in the growth rate or yield of the mutant strain when compared to that of the wild-type strain.

By "salt wash" is meant a procedure known to those skilled in the art. In the procedure, a sub-cellular fraction greatly enriched for ribosomes is treated with a moderately high concentration of salt, typically 500 mM KCl, resulting in the stripping or removal of macromolecules which are said to be "ribosome-associated" as opposed to "integral" ribosomal constituents which are not removed by the "salt wash" treatment. Afterwards, the "salt wash" or ribosome-associated fraction is separated from the integral components by differential centrifugation.

By "altered activity" is meant any increase or decrease in the rate, or any increase or decrease in the specificity, of any step of translation, which is defined as the biochemical steps necessary for the synthesis of proteins by decoding (translating) an RNA template, where the altered translational activity is of sufficient magnitude either to change the growth characteristics of the cell culture in a manner that can be distinguished by human or mechanical monitors as described above, or to alter the biochemical characteristics of an in vitro translation extract, made partially or fully from the mutant cells and compared to the wild-type cell extract.

The means for measuring these differences are explained more fully in the preferred embodiments.

A. Molecules Involved in Translation

The "Component-Specific Assays" described in the preceding pages require a set of strains constructed such that each one is altered for a single translational component or subunit thereof. Components that may be examined include, but are not limited to, any gene product, either protein or nucleic acid, that is known or believed to be a translational component or subunit of such a component, such as those described in preceding sections and others which have not been identified yet. A protein or polynucleotide can be considered to be a translational component if its presence stimulates translation, or any partial reaction of translation, by two fold or greater, or preferably, five fold or greater, or more preferably, ten fold or greater. Furthermore, a protein or polynucleotide can be considered to be a translational component if it makes a product that stimulates translation, or any partial reaction of translation, by two fold or greater, or preferably, five fold or greater, or more preferably, ten fold or greater. Specifically exempted from this latter criterion are ATP, GTP, NADH, NADPH, and their metabolites, all of which would affect translation, but also affect more than 15 other metabolic pathways.

Methods that can be used to analyze components involved in translation include, but are not limited to, functional assays of enzyme activity, in vitro translations, coupled in vitro transcription-translation reactions, incubations with [gamma-$^{32}$P]ATP to allow determination of phosphorylation status, immunoprecipitation, one-dimensional and two-dimensional gel electrophoresis, Western blotting, differential centrifugation, chromatographic purification, UV-crosslinking, gel retardation assays, other DNA-binding and RNA-binding assays, and the like.

Components involved in translation may be purified for characterization and for use in the methods of this invention. Fractionation methods which can be used include, but are not limited to, centrifugation, ammonium sulfate precipitation, other differential precipitations, gel filtration, ion exchange chromatography, hydrophobic interaction chromatography, reverse phase chromatography, affinity chromatography, differential extractions, isoelectric focusing, electrophoresis, isotachophoresis, and the like.

Since translation depends on the availability of mRNA templates, it is also important to extend the analyses to cover the synthesis, processing, transport, and degradation of mRNA. mRNA synthesis (transcription) can be examined in a manner analogous to protein synthesis by utilizing the incorporation of labeled precursors into MRNA in order to determine overall rates of mRNA synthesis and to generate labeled material that can be examined by gel electrophoresis, in this case on agarose as well as polyacrylamide gels. Processing and transport of mRNA can also be examined by using labeled precursors to analyze the sizes and quantities of various labeled RNA species in nuclear and cytoplasmic extracts of cells. Alternatively, the sizes and quantities of these RNAs can be examined by the Northern blot hybridization procedure, in which RNAs separated by electrophoresis and transferred to a hybridization membrane are detected by a labeled nucleic acid probe specific for the RNAs of interest.

Degradation of mRNAs can be followed by similar procedures, using radiolabeled mRNAs or Northern blot hybridizations to trace the fate of mRNAs. For all stages of mRNA synthesis, processing, and degradation it may also be useful to measure the activities and concentrations of the enzymes and other proteins involved, such as RNA polymerases, splicing enzymes, splice-junction binding proteins, and ribonucleases responsible for degrading mRNAs. Alterations in transcriptional activity may also be detected and analyzed utilizing cell extracts for in vitro transcription reactions.

B. Underexpressing Mutants

Expression levels of a cloned gene are manipulated by altering the gene's non-coding sequences and then using the altered construct to replace the native gene by transformation and homologous recombination in vivo, using methods known to those skilled in the art (Molecular Cloning, a Laboratory Manual, Second Edition, J. Sambrook, E. F. Fritsch, and T. Maniatis, eds., Cold Spring Harbor Laboratory Press: New York, 1989; Guide to Yeast Genetics and Molecular Biology. C. Guthrie and G. Fink, eds. Methods in Enzymology, Vol. 194, 1991). The alterations can be in the form of deletions in the region upstream of the transcription unit made by taking advantage of existing restriction enzyme. sites in combination with DNA ligase, polymerase or exonuclease. Alternatively, when a known consensus sequence for transcriptional activation such as a RAP1-binding site or a poly-pyrimidine tract is recognized in the promoter region, the consensus sequence can be altered by a site-directed mutagenesis scheme.

For example, the region upstream of the YEF3 gene (encoding EF-3) contains the sequence CCACcC ATGCATAA (SEQ. ID. NO.: 6), which is a consensus sequence for the binding of the transcriptional activator protein RAP1, can be altered to a less effective consensus sequence (Nieuwint et al. 1989; Vignais et al. 1990) with the effect of reducing the net synthesis of EF-3, a translation factor essential for cell growth.

Specifically, a plasmid bearing the YEF3 gene is linearized with the restriction enzyme NsiI, which recognizes the ATGCAT sequence underlined above. A yeast or bacterial cell that is homologous-recombination-proficient (i.e., wild-type) is transformed with the linearized plasmid plus a double-stranded oligonucleotide of ca. 40 bp that is nearly identical to YEF3 and straddles the NsiI restriction site. The viability of the cells after transformation with the linear plasmid and selection for a plasmid-born marker (e.g., ampicillin resistance or uracil prototrophy) will be dependent on recombination of the plasmid and the double-stranded oligonucleotide since the cell is unable to maintain or ligate a linear plasmid. Candidate plasmids are first screened by digestion with NsiI, and then verified by DNA sequencing. The non-identities with YEF3 are a single base change that destroys the NsiI site and a change that causes a decrease in RAP1- mediated transcriptional activation, such as changing the lower-case "c" in the preceding sequence to an "A" (Nieuwint et al. 1989; Vignais et al. 1990 —This particular change is merely presented by way of example but it probably would decrease YEF3 expression to a level too low to support growth. In this case, other changes could be made and tested to generate a suitable, viable mutant).

The NsiI site is destroyed to facilitate later screening for the desired mutant allele since nearly all of the plasmids that have lost the site will contain the other mutation as well. Those retaining the site are probably derived from contaminating uncut plasmid used in the transformation. The effect of these changes can be monitored by subcloning a reporter gene, such as the E. coli genes lacZ or uidA, in frame at the XbaI site at ca. the tenth codon of the YEF3 ORF, and measuring the reporter gene activity with the wild-type and mutant promoter sequences. Alterations used to decrease gene expression also include, but are not limited to, sequence changes and deletions that decrease the message stability or yield, changes that make the initiation context less favorable, or changes that alter the ORF to a less favorable codon bias.

After the mutant allele is constructed, it is used to replace the wild-type allele by the "two-step" gene replacement strategy (F. Winston, F. Chumley, and G. R. Fink, Methods Enzymol. 101: 211–228, 1983).

First, the appropriate yeast recipient (leu2 ura3) is transformed with the wild-type YEF3 gene on a replicating plasmid that has a selectable marker other than URA3, such as LEU2. Afterwards, a plasmid bearing the 1.6 kb EcoRI-XbaI fragment of the mutant yef3 promoter, the URA3 gene, and having no yeast ARS or centromere sequences is linearized in the yef3 gene at the XhoI site and transformed into the recipient with selection for uracil prototrophy by standard methods. This procedure is designed to produce a strain that has wild-type YEF3 on the episome, the wild-type YEF3 promoter fused to a truncated ORF, and the mutant promoter fused to the wild-type ORF, with the latter two being in a tandem array in the order described. These transformants are then screened for loss of the LEU2 marker after growth on non-selective medium, with four possible outcomes: 1) the Leu$^-$ colonies will also be Ura$^-$, which means that the linear plasmid integrated into the episome rather than the chromosome; 2) no Leu$^-$ colonies will be obtained, which suggests that expression of YEF3 from the mutant promoter is too low to support growth; 3) the Leu$^-$ colonies are Ura$^+$ and have no growth defect, suggesting that the mutation has a negligible effect on expression; 4) the Leu$^-$ colonies are Ura$^-$ and have some degree of growth defect, which is the desired result.

For the "second" step, the Leu$^+$ Ura$^+$ transformant is replica-plated to synthetic medium containing 5-fluoro-orotic acid (5-FOA), which selects recombinants that have lost the URA3 gene (This is a positive selection for mutants lacking orotidine-5'-phosphate decarboxylase activity in yeast *Saccharomyces cerevisiae*: 5-fluoro-orotic acid resistance, J. D. Boeke, F. LaCroute, and G. R. Fink, Mol. Gen. Genet. 197:345–346, 1984). The Ura$^-$ cells are the result of homologous recombination with excision of the plasmid sequences and one of the two chromosomal copies of yef3. One portion of the recombinants will have a wild-type YEF3 gene, and the other portion will have an altered vef3 gene with the mutant promoter fused to the wild-type ORF. These two products can be distinguished quickly by a PCR screen followed by digestion with NsiI enzyme.

Alternatively, the mutant allele can be integrated at another locus in the genome of a strain lacking the native, wild-type copy of the gene. This can be accomplished, for example, by deleting or disrupting one copy of the wild type gene in a diploid strain, integrating the mutant copy at another locus, such as URA3, sporulating the diploid, and screening for haploids lacking the wild-type allele, but having the mutant allele. Other, similar methods known to those skilled in the art can also be used.

Several genes encoding a translational component in yeast are duplicated. The two copies are often expressed differentially, and deletion of one has no effect on growth, while deletion of the other causes a slow growth phenotype. For these components, underexpression mutants are generated by deletion of one of the gene copies using techniques well known to those skilled in the art.

C. Defective Variant Mutants

Yeast mutants with a mutation in a translational-component-encoding gene have been widely reported in the scientific literature and are available from the appropriate researchers or central depositories such as the American Type Culture Collection or the Berkeley Yeast Genetics Stock Center. In general the mutants will be in diverse genetic backgrounds that will complicate comparisons between them should they be used directly for screening test compounds. In the preferred embodiment, the desired mutations are cloned and reintroduced into an isogenic background. The mutant allele is recovered by PCR or by using the cloned wild-type gene in a gapped plasmid repair or marker rescue experiment according to methods known to those skilled in the art (e.g., T. L. Orr-Weaver, J. W. Szostak, and R. J. Rothstein, Methods Enzymol. 101: 228–245, 1983).

D. Overexpressing Mutants

Genes that are cloned from an appropriate plasmid library can be used as is if the copy number of the plasmid is greater than one. Genes obtained from other sources can be cloned into plasmid vectors known to exist in high copy numbers in yeast using standard laboratory techniques (Molecular Cloning, a Laboratory Manual, Second Edition, J. Sambrook, E. F. Fritsch, and T. Maniatis, eds., Cold Spring Harbor Laboratory Press: New York, 1989; Guide to Yeast Genetics and Molecular Biology. C. Guthrie and G. Fink, eds. Methods in Enzymology, Vol. 194, 1991), or by selecting for homologous recombination between the original vector and an appropriate vector as described by J. R. Erickson and M. Johnston, Genetics 134:151–157, 1993). In another variation of this scheme, genes encoding more than one subunit of a translational component can be combined into one plasmid by the same techniques. The most common of these high copy vectors contains either an ARS (autonomous replication sequence) with no accompanying centromeric sequences, or part or all of the 2-micron plasmid of yeast. Higher copy number can also be achieved by integrating multiple copies of the gene into chromosomal DNA. As an alternative to, or in combination with, these high copy schemes, the gene of interest can be altered so as to increase its net expression, for example, by improving codon bias or the context of translational initiation, by altering the promoter so as to increase transcription, or by altering the mRNA sequence so as to increase its stability in vivo. The gene or genes of interest can then be transformed separately into the same yeast strain, thereby forming a collection of transformed strains sharing an otherwise isogenic makeup.

EXAMPLE 3

Screening with Translation-Component Mutant Cells

In order to identify potential therapeutics from a large library of compounds, the collection of mutants is grown in parallel in liquid yeast media in the presence and absence of the compound. If sufficient compound is available, the test is repeated in a set of different media, such as rich medium with dextrose (YEPD) or glycerol (YEPG) as a carbon source, or synthetic medium (SD) with ammonium sulfate or proline as a nitrogen source, that are known to have significant effects on yeast metabolism (Guide to Yeast Genetics and Molecular Biology, C. Guthrie and G. Fink, eds. ethods in Enzymology, Vol. 194, 1991; The Molecular Biology of the Yeast Saccharomyces, J. Strathern, E. W. Jones, and J. R. Broach, eds., CSH Laboratory Press: N.Y., 1981; The Molecular Biology of the Yeast Saccharomyces, J. R. Broach, J. R. Pringle, and E. W. Jones, eds., CSH Laboratory Press: N.Y., 1991).

Referring to FIG. 8, the cultures are pre-grown overnight (12–24 hours) in 3 ml SD minimal medium (2% dextrose, 0.67% Difco yeast nitrogen base without amino acids, and any supplements required for growth by the test strains) in 18×150 mm test tubes on a tube roller at 30° C. The overnight cultures are diluted in fresh SD minimal medium: the absorption plus light scattering of the culture is measured at 600 nm (i.e. measured by the reduction of light transmission through the sample and commonly referred to as $A_{600}$), and based on the value so obtained, the culture is diluted to give an absorbance plus light scattering value equivalent to $3 \times 10^{-5}$. This dilution protocol was empirically derived with the intention of delivering 4–15 cells per well. The diluted culture is dispensed into 96-well microtiter dishes, 0.2 ml per well. Candidate compounds are mixed with the cell suspensions in the microtiter disher, 2 $\mu$l per well. The plates are incubated for 2 days at 30° C. with no disturbance. At the end of the incubation period, a well with no growth inhibition has the appearance of several small colonies growing on the bottom of the well. Because the correlation between light scattering and cell density may not be entirely reproducible form one spectrophotometer to the next, a small amount of experimentation would be required in adjusting the dilutions to get precisely the same effect. However, the density of the cells is not critical to the success of the protocol.

Growth inhibition of a subset of the mutant collection implies that the compound targets a specific step in translation. Growth inhibition of all of the strains implies that the compound either is at too high of a dose for interpretation or inhibits growth through a non-translation target. In either case, the test is repeated using a lower dose of the compound. The target or targets of the compound can be inferred from the response of the various mutant cell cultures, e.g., a mutant partially deficient for EF-2 would be expected to be more sensitive to hygromycin (Protein Synthesis, M. F. Tuite, in: The Yeasts, Vol. 3, 2nd ed., ISBN # 0–12–596413–7, 1989) than either a wild-type strain or a mutant partially deficient for eIF-4A, which is not a target for this inhibitor.

EXAMPLE 4

Screening with YEF3 Wild-Type and Mutant Cells

Applying the general procedure described in Example #3, a screening system was established as follows to identify potential antifungal agents whose activities are mediated through or enhanced by the fungal-specific translation factor EF-3. This system is based on the principle that agents which affect EF-3 can be identified from a large library of compounds by their differential effects on isogenic yeast strains that differ in YEF3 gene dosage, and thus in intracellular concentration of EF-3. Using published information concerning the cloning and sequencing of the YEF3 gene (J. Biol. Chem. 265:1903–1912, 1990, and Biochim. Biophys. Acta 1050:230–234, 1990), primers were designed which enabled amplification by the polymerase chain reaction of a DNA fragment corresponding to base pairs 3939 to 4574 listed in the GenBank™/EMBL Data Bank accession file number J06197. The amplified fragment was used as a hybridization probe to identify a YEF3-containing clone in a *Saccharomyces cerevisiae* genomic library. Isogenic strains were then constructed by introducing two similar plasmids, in parallel, into the same yeast strain. The first plasmid, pRS426 (Gene 110:119–122, 1992), contained DNA seqeunces that in *Saccharomyces cerevisiae* confer maintenance at a high copy number, which is typically between 10 and 50 copies per cell, and also confer uracil prototrophy in a ura3 mutant. The second plasmid was derived from the first, but contained the cloned YEF3 gene. Cell cultures were prepared as described in Example #3. The system was tested using compounds known to have an impact on translational elongation: cycloheximide, paromomycin, and hygromycin B. Growth of the yeast strain bearing the high-copy YEF3 plasmid was inhibited at paromomycin and hygromycin B concentrations four-fold lower than those required to inhibit the strain bearing the control plasmid, pRS426. In contrast, the inhibitory concentration of cycloheximide was similar for both strains. Thus the screening system was capable of identifying differential effects of elongation-influencing compounds on the two strains, and of distinguishing between compounds whose effects appear to be mediated or enhanced by YEF3 (such as paromomycin and hybromycin B) and those whose are not (such as cycloheximide).

EXAMPLE 5

Screening With Mutant-Cell Extracts

Cell extracts can be made from the translational-component mutants described above and used to screen for translation inhibitors in vitro. Each of the translational-component mutants described above is identical to a wild-type strain except for one of the translational components. Cell extracts can be made from the wild-type and mutant strains and used for in vitro translation by methods known to those skilled in the art (e.g., mRNA-Dependent Yeast Cell-Free Translation Systems: Theory and Practice, M. F. Tuite and J. Plesset, Yeast 2:35–52, 1986; Protein Synthesis, M. F. Tuite, in: *The Yeasts*, Vol. 3, 2nd ed., ISBN # 0-12-596413-7, 1989).

A given compound can be added in parallel to an extract made from the wild-type strain and to an extract or extracts from one or more of the mutant strains. The effect of the compound on translation can be determined by methods known to those skilled in the art, such as by incorporation of a radioactively-labeled amino acid into polypeptides, which can be measured by liquid-scintillation counting of TCA-precipitable material, by fluorography of electropherograms of the translation products, by direct staining of the electropherograms for protein, by immunological or enzymatic tests for a protein encoded by a mRNA included in the translation mix, or by other such methods known by those skilled in the art. The target or targets of the compound,can be inferred from the response of the various mutant cell extracts.

6. Suppression of Termination Assay

Referring to FIG. 5, the invention features a method for screening for an antifungal agent, in which a particular yeast gene is identified or constructed such that production of its complete gene product is dependent upon interference in translation termination, and the gene product is used as an indicator of test compound activity. The gene product may be used directly to report test compound activity, for example by measuring its concentration or activity by in vivo or in vitro assay. Alternatively, the expression of the gene product may be used to drive expression of other genes that in turn function as the reporters of test compound activity.

The method thus includes contacting a yeast cell or cell extract containing a mRNA encoding the gene product, whose complete translation depends on interference in the process of translation termination, with a potential antifungal agent under conditions that allow little or no synthesis of the gene product in the absence of the agent. The method finally includes determining whether the agent increases the level of translation of the gene product or of a reporter molecule whose synthesis is dependent on the gene product. Paradoxically, any agent that does increase this level is potentially useful as an antifungal agent, albeit at higher doses.

In the more preferred embodiment of this "Suppression of Termination Assay", any suitable reporter, such as the acid phosphatase encoded by the *S. cerevisiae* PHO5 gene, the protein product of which can be readily quantitated by enzyme assay, immunodetection, or any other method known to those skilled in the art, is altered by introducing a translation termination codon in the ORF, preferably near the beginning of the ORF, with the result that the reporter protein is expressed at very low levels, and a weak signal is obtained with the chosen assay. Compounds that interfere with the ability of the ribosome to terminate translation cause misreading of this introduced termination codon for a sense codon, which results in increased expression of the reporter protein.

Note that this assay does not rely on discrimination between the introduced termination codon and naturally occurring ones, because the anti-termination event can still be relatively rare and score well in the assay. This assay can be performed in vitro with cell-free translation extracts, or preferably, with intact cells.

Although the mechanics of this screen for anti-fungals bear some similarity to an assay devised for measuring the strength of interactions between termination codons and genetic suppressors of translation termination in Saccharomyces (Quantitation of Readthrough of Termination Codons in Yeast Using a Novel Gene Fusion Assay, M. Firoozan, C. M. Grant, J. A. B. Duarte, and M. F. Tuite, Yeast 7:173–183, 1991), the current application is distinct from the previous report in significant ways. 1) The current application is directed towards identifying exogenous compounds which interfere with the process of translation termination and act as antifungal agents, while the previous report was concerned with measuring the strength of interactions of endogenous components of the yeast cell. There was no suggestion in, nor is it obvious from, the previous report that their assay could be used or modified for identifying translation inhibitors or antifungal agents. 2) The assay described in the previous paper has technical limitations that would make it unwieldy and less useful as a large-scale screen for genetic mutants or therapeutics. The current method has both subtle and significant differences which make it well-suited as a large-scale screen. In the preferred embodiment, the reporter gene is integrated into a yeast chromosome. Integration dramatically increases the stability of the reporter gene's copy number. Also in the preferred embodiment, PHO5 is used because the enzyme it encodes is secreted to, and is retained on, the cell surface. This location facilitates enzymatic and immunological assays because it obviates the need to break open the cells, and thereby simplifies the screening process.

By "translation termination" is meant the event wherein a translating ribosome meets one of the three common termination codons and successfully reads it as a signal to stop adding amino acids to the nascent polypeptide.

By "termination codon" or the equivalent expression "nonsense codon" is meant one of the three codons, UAA, UGA, or UAG, that normally signals the end of an ORF.

By "sense codon" is meant any one of the 61 codons that normally encodes an amino acid and can signal a beginning or continuation of an ORF.

By "ribosome release" is meant the separation of the ribosome from the mRNA molecule.

A. Reporters and Strains

The current embodiment utilizes a modified form of the yeast PHO5 gene, which encodes a secreted acid phosphatase, however, there is no unique requirement or restriction that PHO5 be used for the underlying concepts to work. Site-directed mutagenesis is used to introduce a stop codon to PHO5, preferably near the beginning of the ORF. Several of these alleles are made. While the native promoter can be used; it is preferable to use a replacement to avoid the limitations of the phosphate regulon. A good replacement for the native promoter is a version of the GCN4 promoter and 5' mRNA leader lacking the four short upstream ORFs. This is a strong promoter that is not subject to any known significant transcriptional regulation. In this preferred embodiment, the PHO4 gene is deleted by methods well known to those skilled in the art. The PHO4 protein is a transcriptional activator of the acid phosphatases encoded by PHO3, PHO5, PHO10, and PHO11. The altered PHO5 gene is intergrated into the yeast chromosome using methods well known to those skilled in the art.

EXAMPLE 6

Screening with the "Suppression of Termination Assay"

The acid phosphatase enzyme can be readily assayed as described (Construction of a Promoter-Probe Vector with the PHO5 Gene Encoding Repressible Acid Phosphatase in *Saccharomyces cerevisiae*, Y.-I. Hwang, S. Harashima and Y. Oshima, Appl. Microbiol. Biotechnol. 28:155–159, 1988). In the preferred embodiment, cells are grown to approximately $1-5 \times 10^7$ cells/ml, and 0.1 ml of culture is aliquoted to 96-well microtiter plate wells containing test compounds or controls. The microtiter plates are then incubated at 30° C. for 5 hours, after which the cells are separated from the medium by centrifugation and aspiration. The cells are then washed once with 0.1 ml 0.05M sodium acetate, pH 4.0, resuspended in 0.2 ml of the same buffer containing 0.025 mg p-nitrophenyl-phosphate, and monitored spectrophotometrically at 410 nm for 60 minutes. The change in absorbance per minute is a measure of the total acid phosphatase activity in the well; an increase in this rate indicates that the test compound interfered with translation termination.

A compound that inhibits termination may be toxic to the cell, and the increase in phosphatase expression could be canceled by a decrease in the number of living cells that are capable of translation. In order to provide a control for this, for each concentration of each test or control compound used, a parallel microtiter plate is prepared and incubated, however, this parallel plate is assayed for an external reductase either encoded or controlled by the FRE1 gene (Ferric Reductase of *Saccharomyces cerevisiae*: Molecular Characterization, Role in Iron Uptake, and Transcriptional Control by Iron, A. Dancis, D. G. Roman, G. J. Anderson, A. G. Hinnebusch, and R. D. Klausner, Proc. Natl. Acad. Sci. 89:3869–3873, 1992). An increase or decrease of more than three fold in the phosphatase:reductase ratio also indicates that the test compound interfered with translation termination. Furthermore, a decrease in the level of reductase expression indicates that the compound is toxic to the fungal cell.

7. Frameshifting Assay

The invention features a method for screening for an antifungal agent, wherein synthesis of a carefully chosen reporter protein is dependent on translational frameshifting. Expression of this protein may be used to directly report test compound activity, either by measuring the gene product directly, by in vivo or by in vitro assay, or the expression of the translational indicator may be used to drive expression of other genes that in turn function as the indicators of test compound activity. This method utilizes a fungal translation-frameshift nucleic acid sequence that allows translation of RNA encoding the reporter protein under frameshifting conditions. A compound that either increases or decreases the frequency of frameshifting may be toxic to the cell.

In the preferred embodiment, the fungal translation-frameshift nucleic acid sequence is located within the same RNA that encodes the reporter protein. The method thus includes contacting a yeast cell or cell extract containing the translation-frameshift nucleic acid sequence with a potential antifungal agent under conditions that allow little or no synthesis of the reporter protein in the absence of the agent. The method finally includes determining whether the agent increases the level of translation of the reporter protein. Paradoxically, any agent that does increase this level is potentially useful as an antifungal agent, albeit at higher doses.

In the more preferred embodiment of this "Frameshifting Assay", any suitable reporter, such as the acid phosphatase encoded by the *S. cerevisiae* PHO5 gene, the protein product of which can be readily quantitated, whether by enzyme assay, immunodetection, or by any other method known to those skilled in the art, is altered by introducing a translation frameshift in the ORF, preferably near the beginning of the ORF, with the result that the reporter protein is expressed at very low levels, and a weak signal is observed with the chosen assay. Compounds that interfere with translation fidelity cause misreading of the introduced frameshift and cause a return to the ORF at some detectable frequency, which results in increased expression of the reporter protein. This assay can be performed in vitro with cell-free translation extracts, or preferably, with intact cells.

By "introduced frameshift" is meant an alteration that is introduced to the ORF of a reporter protein such that the ORF on the 3' side of the alteration is out of frame by plus one or minus one nucleotide relative to the ORF on the 5' side of the alteration. This can be accomplished by many methods known to those skilled in the art, including, but not limited to, the addition or deletion of a number of base pairs, which is not divisible by three, in the ORF, or the addition of a longer sequence which has been demonstrated to be a natural frame-shift sequence, such as, but not limited to the "slip" sequence of the yeast retrotransposons TY1 and TY2 (Ribosomal Frameshifting in the Yeast Retrotransposon TY: tRNAs Induce Slippage on a 7 Nucleotide Minimal Site, M. F. Belcourt and P. Farabough, Cell 62:339–352, 1990).

By "slip" sequence is meant the DNA sequence CTTAGGC (ibid.; SEQ. ID. NO.: 15) which promotes, in cis, a frame-shift of +1 during translation in yeast. However, this sequence is given by way of example only, and is not intended to imply limitation to this specific sequence. Moreover, a sequence that facilitates a −1 frame-shift could also be used in this method.

A. Design of reporters and strains

The current embodiment utilizes a modified form of the yeast PHO5 gene, which encodes a secreted acid phosphatase. However, there is no unique requirement or restriction that PHO5 be used for the underlying concepts to work. Site-directed mutagenesis is used to introduce a stop codon to PHO5, preferably near the beginning of the ORF. Several of these alleles are made. While the native promoter can be used, it is preferable to use a replacement to avoid the limitations of the phosphate regulon. A good replacement for the native promoter is a version of the GCN4 promoter and 5' mRNA leader lacking the four short upstream ORFs. This is a strong promoter that is not subject to any known significant transcriptional regulation. In this preferred embodiment, the PHO4 gene is deleted by methods well known to those o skilled in the art. The PHO4 protein is a transcriptional activator of the acid phosphatases encoded by PHO3, PHO5, PHO10, and PHO11. The altered PHO5 gene is intergrated into the yeast chromosome using methods well known to those skilled in the art.

EXAMPLE 7

Screening with the "Frameshifting Assay"

The acid phosphatase enzyme can be readily assayed as described (Construction of a Promoter-Probe Vector with the PHO5 Gene Encoding Repressible Acid Phosphatase in *Saccharomyces cerevisiae*, Y.-I. Hwang, S. Harashima and Y. Oshima, Appl. Microbiol. Biotechnol. 28:155–159, 1988). In the preferred embodiment, cells are grown to approximately $1-5 \times 10^7$ cells/ml, and 0.1 ml of culture is aliquoted to 96-well microtiter plate wells containing test compounds or controls. The microtiter plates are then incubated at 30° C. for 5 hours, after which the cells are separated from the medium by centrifugation and aspiration. The cells are then washed once with 0.1 ml 0.05M sodium acetate, pH 4.0, resuspended in 0.2 ml of the same buffer containing 0.025 mg p-nitrophenyl-phosphate, and monitored spectrophotometrically at 410 nm for 60 minutes. The change in absorbance per minute is a measure of the total acid phosphatase activity in the well; an increase in this rate indicates that the test compound increased or translation frameshifting; a decrease in this rate indicates that the test compound decreased or translation frameshifting.

A compound that alters the frequency of frames-hifting may be toxic to the cell, and the increase in phosphatase expression could be canceled by a decrease in the number of living cells that are capable of translation. In order to provide a control for this, for each concentration of each test or control compound used, a parallel microtiter plate is prepared and incubated, however, this parallel plate is assayed for an external reductase either encoded or controlled by the FRE1 gene. An increase or decrease of more than three fold in the phosphatase:reductase ratio also indicates that the test compound interfered with frameshifting. Furthermore, a decrease in the level of reductase expression indicates that the compound is toxic to the fungal cell.

8. eIF-2alpha Kinase Activation Assay

The invention features a method for screening for antifungal agents which identifies activators of a kinase that phosphorylates residue serine 51 on the alpha subunit of the translation initiation factor eIF-2, which is encoded in Saccharomyces by the GCN2 gene and is known as the eIF-2alpha kinase or the GCN2 kinase. Phosphorylation of this site on eIF-2alpha is a key step in translational and growth regulation in organisms from yeast to man: translation initiation decreases with increasing kinase activity, and with enough kinase activity, translation is blocked entirely. However, the signals which activate the kinase are very different in these two organisms.

In yeast, the kinase is activated by limitation for an amino acid, presumably due to the consequential increase in uncharged tRNA, an aspect of the "General Amino Acid Control" pathway (Protein Synthesis and Translational Control, A. G. Hinnebusch and S. W. Liebman, pp.626–736, in: *The Molecular Biology of the Yeast Saccharomyces*, J. R. Broach, J. R. Pringle, and E. W. Jones, eds., CSH Laboratory Press: N.Y., 1991).

In man, there is one form of the eIF-2alpha kinase which is activated by heme starvation and another form which is activated by double-stranded RNA; neither of these appear to be activated by amino acid starvation.

This information can be exploited to look for activators of the yeast kinase which have no effect on the mammalian kinases. Such an activator will inhibit fungal growth and give the host a better chance at eliminating the infection.

In the preferred embodiment, known as the "GCN2 Kinase Activation Assay", yeast cells are grown on a medium containing a lethal concentration of an amino acid analog, such as, but not limited to, 5-fluorotryptophan, which exerts its toxic effects by being incorporated into polypeptides during protein translation and not by affecting aminoacyl-tRNA synthesis. A compound which activates the GCN2 kinase to a moderate degree causes a moderate inhibition of translation initiation, which causes an increase in translation of the GCN4 protein, which causes an increase in amino acid biosynthesis, which will "dilute out" the toxic analog. At higher doses, the compound will hyperactivate the GCN2 kinase, which will cause a severe inhibition of translation initiation, which will inhibit growth. In another embodiment, this assay can be performed in vitro by measuring kinase activity on eIF-2alpha substrate (Phosphorylation of Initiation Factor 2alpha by Protein Kinase GCN2 Mediates Gene-Specific Translation Control of GCN4 in Yeast, T. D. Dever, L. Feng, R. C. Wek, A. M. Cigan, T. F. Donahue, and A. G. Hinnebusch, Cell 68:585–596, 1992).

By "General Amino Acid Control", also known as "Cross Pathway Control", is meant the regulatory network, best characterized in Saccharomyces, that is used by the cell to overcome an amino acid limitation or imbalance. Aspects of this metabolic control pathway have been demonstrated in *Aspergillus nidulans* and *Neurospora crassa*, and probably exist in most or all fungi and other mycoses. A comprehensive description of this phenomenon can be found (Protein Synthesis and Translational Control, A. G. Hinnebusch and S. W. Liebman, pp.626–736, in: *The Molecular Biology of the Yeast Saccharomyces*, J. R. Broach, J. R. Pringle, and E. W. Jones, eds., CHS Laboratory Press: N.Y., 1991, and references therein).

EXAMPLE 8

Screening for Hyperactivation of the GCN2 kinase

Some toxic amino acid analogs, such as 5-fluorotryptophan (5-FT), act by being able to substitute for the legitimate amino acid at the level of protein translation, but not being able to substitute for the legitimate amino acid at the level of protein function. This type of toxicity can be ameliorated by increasing the concentration of the legitimate amino acid, either by adding more of it to the medium, or by increasing its synthesis within the cell. Activation of the GCN2 kinase causes an increase in amino acid biosynthesis and an increase in resistance to toxic amino acid analogs like 5-FT. The GCN2 kinase can be activated by genetic mutation, by increasing intra-cellular levels of uncharged tRNA, and possibly by exogeneously-added compounds. This assay is designed to identify compounds that activate the GCN2 kinase. In this assay, a yeast strain that is wild-type for general amino acid control is grown in the presence of a MIC of an amino acid analog such as 5-FT. Candidate compounds are introduced to the culture and growth is measured. Any compound that stimulates the GCN2 kinase will cause increased growth in the presence of 5-FT. In the preferred embodiment, the culturing conditions in this assay would be the same as for the Phenotypic Relaxation Assay, except that 5-FT would be added and tryptophan and 3-aminotriazole would not be added to the medium.

9. eIF-2alpha Kinase Inhibition Assay

The invention features a method for screening for antifungal agents, which will identify inhibitors of a kinase that phosphorylates residue serine 51 on the alpha subunit of the translation initiation factor eIF-2, which is encoded in Saccharomyces by the GCN2 gene and is known as the eIF-2alpha kinase or the GCN2 kinase. Phosphorylation of this site on eIF-2alpha is required for derepression of amino acid biosynthesis during amino acid limitation via General Amino Acid Control (Protein Synthesis and Translational Control, A. G. Hinnebusch and S. W. Liebman, pp.626–736, in: *The Molecular Biology of the Yeast Saccharomyces*, J. R. Broach, J. R. Pringle, and E. W. Jones, eds., Cold Spring Harbor Laboratory Press: N.Y. , 1991). While the GCN2 kinase is not required for growth on balanced-amino-acid medium, it is required for growth on amino-acid-limitation medium.

Such amino-acid-limitation conditions occur frequently in nature, and mammalian-tissue "medium" may represent such conditions from the fungal point of view. The General Amino Acid Control pathway also is known to exist in at least two other fungi, *Neurospora crassa* and *Aspergillus nidulans*, and probably exists in other fungi as well.

In one embodiment of this assay, a yeast strain is constructed that bears a constitutively activated allele of GCN2 that confers a moderately severe slow-growth phenotype; several such strains have been described (Mutations Activating the Yeast eIF-2-alpha Kinase GCN2: Isolation of Alleles Altering the Domain Related to Histidyl-tRNA Synthetases, M. Ramirez, R. C. Wek, C. R. Vazquez de Aldana, B. M. Jackson, B. Freeman, A. G. Hinnebusch, Mol. Cell. Biol. 12:5801–5815, 1992). Any compound which inhibits the kinase, or antagonizes the activity of the kinase by other means, such as, but not limited to, activation of an opposing phosphatase (cf. Truncated Protein Phosphatase GLC7 Restores Translational Activation of GCN4 Expression in Yeast Mutants Defective for the eIF-2-alpha Kinase GCN2, R. C. Wek, J. F. Cannon, T.E. Dever, A. G. Hinnebusch, Mol. Cell. Biol. 12:5700–5710, 1992), will ameliorate the slow growth phenotype and cause the culture to grow faster. At higher concentrations, the compound will block the kinase function entirely, and not permit derepression of amino acid biosynthesis during conditions of amino acid limitation.

Another embodiment of this assay uses a reporter gene which is both positively regulated by GCN2 and produces a toxic, or conditionally toxic, product, e.g., galactokinase in the presence of 2-deoxygalactose. In another embodiment, this assay is performed in vitro by measuring kinase activity on purified eIF-2alpha substrate.

In yet another embodiment of the assay, the constitutively activated kinase is derived from another organism, such as, but not limited to, the GCN2-type kinase from mammalian cells known variously as "p68", "DAI", or "PKR". When introduced into Saccharomyces cells, this kinase functions like a constitutively activated GCN2 kinase.

By "balanced-amino-acid medium" is meant either a defined or undefined (rich) medium containing each of the twenty common amino acids at a concentration high enough to support growth, which could be as little as zero amino acids for a prototroph, yet not so high as to interfere in the utilization or uptake of one or more of the other 20 amino acids, or any other essential nutrient or metabolite.

By "amino-acid-limitation medium " is meant either a defined or underfined (rich) medium which either (1) contains one or more of the twenty common amino acids at a concentration that is not high enough to support growth, (2) lacks an amino acid that is required for growth, (3) contains one or more amino acids at a concentration so high as to interfere in the utilization or uptake of one or more of the other 20 amino acids (or another essential nutrient or metabolite), or (4) contains an inhibitor of amino acid biosynthesis.

By "constitutively activated allele" in the preceding section is meant a mutant allele (version) of a gene encoding a GCN2 protein which is phenotypically active under conditions that keep the wild-type protein inactive, i.e., on amino-acid-balanced medium, also referred to as repressing conditions. Wild-type GCN2 kinase shows very little activity in vivo under such conditions, whereas constitutively activated alleles show more activity. Many alleles have been described with activity levels ranging from slightly elevated to highly elevated. In general, the more activity the allele has, the more slowly the strain containing it grows (Mutations Activating the Yeast eIF-2-alpha Kinase GCN2: Isolation of Alleles Altering the Domain Related to Histidyl-tRNA Synthetases, M. Ramirez11 R. C. Wek, C. R. Vazquez de Aldana, B. M. Jackson, B. Freeman, A. G. Hinnebusch, Mol. Cell. Biol. 12:5801–5815, 1992). Note that a "constitutively activated allele" need not be constitutive in the sense of having no regulation; the protein may instead have a blunted range of regulation.

By "moderately severe slow-growth phenotype" is meant a decrease in the growth rate of at least two fold, but not more than ten fold.

EXAMPLE 9

Screening for Inactivation of the GCN2 kinase

Certain mutant alleles of GCN2 are considered "activated", or "constitutive", because the encoded kinase is active in the absence of the normal stimulation signal. The activity of some of these alleles is high enough to impede the growth of the strain carrying them. Any compound that inhibits the GCN2 kinase would restore the strain to a faster growth rate. In the preferred embodiment, the culturing conditions would be the same as for the Phenotypic Relaxation Assay, except that 3AT would not be added to the medium.

10. Protein-protein Interaction Assay: Dominant Negative Alleles

The invention features a method for screening for antifungal agents by identifying dominant negative alleles of mycotic or bacterial translational components which act by interfering with normal interactions between translation components. This type of interaction allele has been characterized before, e.g., the K136E allele of *E. coli* EF-Tu is a dominant negative mutation that "exerts its effect by sequestering EF-Ts" (Y. W. Hwang, M. Carter, and D. L. Miller, J. Biol. Chem. 267:22198–22205, 1992: Y. W. Hwang, A. Sanchez, and D. L. Miller, J. Biol. Chem. 264:8304–8309, 1989). Note, however, that these authors did not suggest any relevance to therapeutics discovery in their papers. Once isolated, the gene products of the dominant negative alleles are reduced progressively in size to the smallest fragment possible. Small peptides containing the dominant negative mutation then are used either as therapeutics or as lead compounds for systematic chemical drug design.

By "dominant allele" is meant either a wild-type or mutant allele that exerts its effect or phenotype in the presence of a recessive allele of the same gene. Note that the terms dominant and recessive alleles are defined relative to one another, and are not absolute.

By "dominant negative allele" is meant a dominant allele that overrides or interferes in the function of recessive alleles.

By "normal interaction" is meant the common or consensus interaction that occurs in strains bearing no known mutations affecting the metabolic pathway in question.

By "interfering with normal interaction" is meant a perturbation of the normal interaction, such as, but not limited to, perturbations which cause the interaction to be much stronger, weaker, more specific, or less specific.

By "smallest fragment possible" is meant the smallest representation, preferably fewer than ten and more preferably fewer than five amino acids long, that still retains the activity of interest. Short peptides like this are already known in other applications, e.g., the tetrapeptide GLY-PRO-ARG-PRO blocks fibrin polymerization, and leupeptin, an N- and C-terminal-blocked tripeptide, mimics the substrate and thereby competitively inhibits serine protease activity. Multiple examples of this type, along with scientific references, can be found on pages 1035–1102 in the 1993 catalog of the Sigma Chemical Company, St. Louis, Mo.

A. Screening for Dominant Negative Alleles

The following is a brief outline of a protocol useful in this invention: 1) Start with cloned translational component genes. 2) Mutagenize said genes by methods well known to those skilled in the art. 3) Put the mutant genes under the control of an inducible promoter in a plasmid. 4) Transform the plasmid into yeast or bacteria. 5) Screen for plasmids which inhibit growth under inducing conditions. 6) Subclone the open reading frames (ORFs) to look for the smallest peptide that inhibits yeast growth. 7) Chemically modify the peptide to find even more potent analogs.

11. Protein-protein Interaction Assay: Two-hybrid Methods

The invention features a method for screening for antifungal agents using methods based in part on the "two-hybrid approach." Under the "two-hybrid approach," two test proteins or protein domains which interact physically with each other are separately fused to two heterologous domains, e.g., the DNA-binding and transcription-activation domains of a protein, such as the GAL4 protein from Saccharomyces, which when brought into proximity by an interaction between the two test proteins or protein domains under study cause the generation of a detectable signal, such as the synthesis of a reporter polypeptide. In this invention, the size of one or both of the interacting translational component domains is then reduced by deletion until the minimum fragment required for interaction is isolated. In the preferred embodiment, this small peptide is then amplified by methods known to those skilled in the art, and tested for its ability to cause inhibition of translation in vitro and for anti-fungal activity in vivo. In the more preferred embodiment, the small inhibitory peptide serves as a model compound for drug design studies.

In a second embodiment of this aspect, one of the two interacting domains is separated from the DNA-binding or transcription-activation domain, mutagenized by methods known to those skilled in the art, and then introduced separately under the control of a regulatable promoter. The mutagenized copies are then screened to find derivatives with the highest potency at blocking the interaction of the wild-type domains. The derivatives are then amplified by methods known to those skilled in the art and tested for inhibition of translation in vitro and for anti-fungal activity in vivo.

In a third embodiment of this aspect, a library of compounds is screened for their ability to block the interaction of the two domains in vitro, or more preferably, in vivo.

By "two hybrid approach" is meant a methodology described (The Two-Hybrid System: A Method to Identify and Clone Genes for Proteins that Interact with a Protein of Interest, C.-T. Chien, P. L. Bartel, R. Sternglanz, and S. Fields, Proc. Natl. Acad. Sci, 88:9578–9582, 1991) for the purpose of identifying an unknown protein, the gene for which is in a plasmid library, which interacts with a protein of interest, the gene for which has been cloned. As a method for identifying such unknown proteins, this is a method well known to those skilled in the art. The use of this method as described above for the purposes of drug discovery is very different from that envisioned by the authors of the original paper, and is in no way anticipated by those authors.

A. Screening with the Two-hybrid System

The following is a brief outline of a protocol useful in this invention:

1) Start with cloned genes for two mycotic or bacterial translational components that physically interact. 2) Attach one to the GAL4 DNA-binding domain under the control of an inducible promoter; attach the other to the GAL4 transcription-activation domain under an inducible promoter. 3) Determine whether they interact with each other by screening for transcription activation. 4) Reduce the size of the translational components to find the smallest functional fragments. 5) Chemically modify the smallest fragments to increase potency. 6) Screen for compounds which interrupt the transcription activation in part 3.

12. Inhibition of Mitochondrial Protein Synthesis

Mitochondrial translation can be distinguished from cytoplasmic translation using cycloheximide, a potent inhibitor of cytoplasmic translation. A cell culture is grown to approximately $1-5 \times 10^7$ cells/ml, cycloheximide is added to 5 mg/l. After 30 min, the culture is divided into aliquots and mixed with the test compounds. After an additional 30 min, a radioactive amino acid is added, and the cultures are incubated for an additional hour. Cold trichloroacetic acid is added to 10% final concentration, and the sample is then incubated at 4° C. for 20 minutes and centrifuged. The pellet is washed 3 times with approximately 0.2 ml acetone, and the retained radioactive label is assayed by liquid scintillation counting. This protocol will remove unincorporated radioactive amino acids, and retain radioactive amino acids which have been incorporated into polypeptides through the action of mitochondrial protein synthesis. An inhibitor of mitochondrial protein synthesis will cause a reduction in the amount of radioactivity present at the end of this protocol.

13. Method for Increasing Test Organism's Utility

The invention provides a novel method for increasing the efficiency of screening for useful agents by making the target cell, or organism, more vulnerable to penetration by test compounds. In a preferred embodiment, the method includes identifying gene products that confer a natural net permeability barrier to exogeneously applied compounds and a method for removing the genes encoding these products, which will result in the production of a cell line that is susceptible to many more compounds and to smaller amounts of many compounds.

In one embodiment, the method uses the yeast *S. cerevisiae* as the target cell to identify translational inhibitors, but the underlying concepts are applicable to other cell types and organisms, including, but not limited to, other fungi, bacteria, amoebae, dinoflagellates, plasmodia, plasmodia cell lines, nematodes, nematode cell lines, insects, insect cell lines, green plants, plant cell lines, animals, animal cell lines, tumors, and tumor cell lines, for the purposes of identifying not only translation-inhibitory compounds, but also any other therapeutic that acts on an intracellular target.

Once a useful lead compound is identified that is effective with the genetically permeabilized target organism, it can be tested for efficacy with the original target organism. Even if the original target organism is less permeable or impermeable to the lead compound, the compound can be rationally modified by methods well known to those skilled in the art so as to improve its permeability qualities while retaining its useful therapeutic qualities.

This embodiment takes advantage of the knowledge that Saccharomyces cells use a net permeability barrier, provided for by a network of gene products, to resist partiallly or completely a large number of compounds that are capable of inhibiting essential biochemical reactions in whole cell extracts. Furthermore, when yeast cells are grown in the presence of a growth-inhibitory compound, they frequently mutate into resistant cells that unexpectedly show cross-resistance to a large number of compounds unrelated in structure or target.

In the literature, this phenomenon is referred to as "pleiotropic drug resistance" (PDR), and bears many similarities to the "multi-drug resistance" (MDR) phenomenon observed in mammalian cells, Plasmodia and other organisms. Cells in which a PDR gene, such as PDR1 or PDR5, has been deleted become hypersensitive to these compounds (E. Balzi and A. Goffeau, Biochim. Biophys. Acta, 1073: 241–252, 1991, and references therein). From the perspective of drug discovery, this baseline PDR phenomenon causes inefficiency since many potentially useful compounds are not accumulated by the cell and therefore are overlooked during screening. Systematic deletion of these PDR (or MDR) genes from the genome will result in more effective drug discovery assays, be they the translation-blocker assays of this invention, another assay with yeast using other biochemical targets, or similar drug-discovery assays with an organism other than yeast using any intracellular target. Once a lead compound is identified using these hyper-permeable organisms, its effectiveness against (ability to permeate) the wild-type organism can be improved by chemical modification.

At least 12 genes conferring pleiotropic gene resistance are known in yeast, including, but not limited to, PDR1, PDR2, PDR3, two different genes called PDR4, one of which is also known as YAP1, PDR5, PDR6, PMA1, CPR1, STE6 (E. Balzi and A. Goffeau, Biochim. Biophys. Acta, 1073: 241–252, 1991, and references therein), and any other gene which can be altered so as to confer increased resistance or sensitivity to more than one compound not related in target or structure. Any or all of these, as well as others either not described in the reference, or not known at this time, can be deleted from the genome by methods well known to those of ordinary skill in the art in order to obtain the described benefit of increased efficiency of drug discovery assays.

By "PDR" or "MDR" gene is meant any gene encoding a polypeptide or polynucleotide that can act in vivo to increase the cell's net permeability barrier to two or more small molecules which are not obviously related structurally. Genes encoding a polypeptide or a polynucleotide, which can act in vivo to decrease the cell's net permeability barrier to two or more small molecules that are not obviously related structurally, can also be considered to be "PDR" or "MDR" genes if overexpression of the gene product makes the cell more sensitive to the compounds.

In the Example delineated in this Application, "PDR4" is used to designate the gene described within GenBank accession number X53830.

By "net permeability barrier" is meant a barrier to the accumulation of an active form of an exogeneously applied compound inside of the cell boundary. This barrier to accumulation can be due to an actual barrier to, or blockade of, the compound, i.e., the compound never crosses the cell boundary, or due to a kinetic barrier, i.e., the compound crosses the cell boundary, but is either quickly excluded from the cell or quickly sequestered or inactivated within the cell, such that the compound does not have an opportunity to interact with its intracellular target, or a combination of these types of barriers. Note that this definition also includes enzymes such as, but not limited to, glutathione-S-transferases, cytochrome P-450s, and monooxygenases, that act relatively non-specifically to chemically inactivate a range of compounds (e.g., Gene-Specific Oligonucleotide Probes for alpha, mu, pi and Microsomal Rat Glutathione-S-Transferases: Analysis of Liver Transferase Expression and Modulation by Hepatic Enzyme Inducers and Platinum Anticancer Drugs, D. J. Waxman, S. S. Sundseth, P. K. Srivastava, D. P. Lapenson, Cancer Res. 52:5797–5802, 1992; Species Differences in the Toxicity and Cytochrome P450 IIIA-Dependent Metabolism of Digitoxin, D. C. Eberhart, B. Gemzik, M. R. Halvorson, A. Parkinson, Mol. Pharmacol. 40:859–867, 1991; Detoxification of the Organophosphorous Insecticide Chlorfenvinphos by Rat, Rabbit and Human Liver Enzymes, D. H. Hutson and C. J. Logan, Xenobiotica 16:87–93, 1986; Flavin-Containing Monooxygenase: A Major Detoxifying Enzyme for the Pyrrolizidine Alkaloid Senecionine in Guinea-Pig Tissues, C. L. Miranda, W. Chung, R. E. Reed, X. Zhao, M. C. Henderson, J.-L. Wang, D. E. Williams, D. R. Buhler, Biochem. Biophys. Res. Commun 178:546–552, 1991).

EXAMPLE 10

Improved Yeast Strains for Drug Screening

The genes PDR1 and PDR4 were deleted from *S. cerevisiae*. The DNA sequence for PDR1 and PDR4 can be found in the GenBank database under the accession numbers J03487 and X53830, respectively. Both of these genes are deleted by following a parallel procedure, as follows. Four oligonucleotides (oligos) were synthesized for each gene. For PDR1: oligo PDR1-1 (ggg cat gcA CGC CAA ACG ATC GCG (SEQ. ID. NO.: 7), nucleotides 34–49), oligo PDR1-2 (ggg gat ccA GCC TCG CAT CTC CAG (SEQ. ID. NO.: 8), complement to nucleotides 466–451), oligo PDR1-3 (ggagat cTA TCC TGT GGA GCG ACG (SEQ. ID. NO.: 9), nucleotides 3615–3631), oligo PDR1-4 (gg g aat tcA TGG TGG CGA GAC GGG (SEQ. ID. NO.: 10), complement to nucleotides 4136–4121); for PDR4: oligo PDR4-1 (ggg cat gcA AGT ACG GGA ACG AGG (SEQ. ID. NO.: 11), nucleotides 1168–1193), oligo PDR4-2 (gg g cat ccA GCG ACC TCT TGG CGG (SEQ. ID. NO.: 12), complement of nucleotides 1659–1644), oligo PDR4-3 (gg a gat ctG TTC CAT CTA AGG AAG G (SEQ. ID. NO.: 13), nucleotides 3392–3408), oligo PDR4-4 (GGG AAT TCA TAC ATA GTC TAA ATA TAT TTA (SEQ. ID. NO.: 14), complement of nucleotides 3761–3734), where restriction enzyme sites are underlined, native DNA sequences are in upper case, and the numbering is according to the GenBank file.

The pairs of oligonucleotides, PDR1-1/1-2, PDR1-3/1-4, PDR4-1/1-2, and PDR4-3/4-4, were each used to amplify a fragment of the respective PDR gene from yeast genomic DNA by the polymerase chain reaction, and ligated directly into a vector prepared for cloning PCR fragments (TA-Cloning Kit from Invitrogen, Inc.). These fragments were then subcloned into the vector pNK294 (E. Alani, L. Cao, and N. Kleckner, Genetics 116: 541–545, 1987) as follows: The PCR fragment made with oligos PDR1-1/1-2 was digested with the restriction enzymes SphI and BamHI, and subcloned into the same sites in the plasmid pNK294; in parallel, the same was done with the PCR fragment made with oligos PDR4-1/4-2. After verification of the subclones, the PCR fragment made with oligos PDR1-3/1-4 was subcloned into the EcoRI and BqlII restriction sites after digestion with the same enzymes; in parallel, the same was done with the PCR fragment made with oligos PDR4-3/4-4. At this point, both of the plasmids contained a fragment of DNA that has an interrupted copy of a PDR gene, where the center part of the gene was replaced by a cassette containing the yeast URA3 gene flanked by two repeats of an 1150 bp fragment from the *E. coli* hisG gene.

The Pdr1 deletion/disruption allele was excised from its plasmid with the restriction enzymes SphI and EcoRI, and the fragment was used to transform, with selection for uracil prototrophy, a yeast strain that has no functional URA3 gene. The resultant $Ura^+$ transformants were checked by Southern blotting or PCR assay to verify that the endogenous PDR1 gene had been replaced through homologous recombination with the deletion/disruption allele. The $Ura^+$ transformant was then grown on medium containing uracil and 5-fluoro-orotic acid (5-FOA), which is converted into a toxic metabolite by the enzyme encoded by the URA3 gene, and therefore selects for loss of the gene. Loss of the URA3 gene was facilitated by the presence of the hisG DNA repeats, which provide a substrate for homologous recombination, leaving one copy of the repeat in the middle of the PDR1 gene. The process was then repeated by transforming the resulting pdr1 ura3 double mutant with the analogous pdr4 deletion/disruption allele. In this way, several or all of the genes conferring pleiotropic drug resistance can be removed from the same cell line.

14. Efficacy-testing of Putative Anti-fungal Agents

Methods for testing the efficacy of putative anti-fungal compounds are provided. Each candidate compound is first tested for its effects on in vitro translation in extracts from Saccharomyces, using methods known to those skilled in the art. Each compound is also tested for efficacy in inhibiting the growth of more medically or commercially relevant fungi on defined and rich media, in animal models, and in controlled clinical studies using methods known to those skilled in the art and approved by the Food and Drug Administration, such as, but not limited to, those promulgated in The Federal Register 47 (no. 56): 12558–12564, Mar. 23, 1982.

15. Toxicity-testing of Putative Anti-fungal Agents

Methods are provided for determining whether an agent active in any of the methods listed above has little or no effect on the translational machinery of a human cell line and is not toxic to human cells, and further determining whether the agent is active under in vivo conditions (ibid.). Such agents are then formulated in a pharmaceutically acceptable buffer or in buffers useful for standard in vitro tests.

By "pharmaceutically acceptable buffer" is meant any buffer which can be used in a pharmaceutical composition prepared for storage and subsequent administration, which comprise a pharmaceutically effective amount of an agent as described herein in a pharmaceutically acceptable carrier or diluent. Acceptable carriers or diluents for therapeutic use are well known in the pharmaceutical art, and are described, for example, in *Remington's Pharmaceutical Sciences*, Mack Publishing Co. (A. R. Gennaro edit. 1985). Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

A. Additional screens for Toxicity: Method 1

Agents identified as having antimycotic or anti-fungal activity are assessed for toxicity to cultured human cells. This assessment is based on the ability of living cells to reduce 2,3, -bis[2-methoxy-4-nitro-5-sulphonylphenyl]-5-[(phenylamino)carbonyl]-2H-tetrazolium hydroxide] otherwise referred to as XTT (Paull et al., J. Heterocyl. Chem. 25: 763–767 (1987); Weislow et al., 1989, J. Natl. Canc. Inst. 81:577). Viable mammalian cells are capable of reductive cleavage of an N—N bond in the tetrazole ring of XTT to form XTT formazan. Dead cells or cells with impaired energy metabolism are incapable of this cleavage reaction. The extent of the cleavage is directly proportional to the number of living cells tested. Cells from a human cell line such as HeLa cells are seeded at $10^3$ per well in 0.1 ml of cell culture medium (Dulbecco's modified minimal essential medium supplemented with 10% fetal calf serum) in the wells of a 96 well microtiter plate. Cells are allowed to adhere to the plate by culture at 37° C. in an atmosphere of 95% air, 5% $CO_2$. After overnight culture, solutions of test substances are added in duplicate to wells at concentrations that represent eight half-decade log dilutions. In parallel, the solvent used to dissolve the test substance is added in duplicate to other wells. The culture of the cells is continued for a period of time, typically 24 hours. At the end of that time, a solution of XTT and a coupler (methylphenazonium sulfate) is added to each of the test wells and the incubation is continued for an additional 4 hours before the optical density in each of the wells is determined at 450 nm in an automated plate reader. Substances that kill mammalian cells, or impair their energy metabolism, or slow their growth are detected by a reduction in the optical density at 450 nm in a well as compared to a well which received no test substance.

B. Additional screens for Toxicity: Method 2

Antifungal compounds are tested for cytotoxic effects on cultured human cell lines using incorporation of $^{35}S$ methionine into protein as an indicator of cell viability. HeLa cells are grown in 96 well plates in Dulbecco's minimal essential medium supplemented with 10% fetal calf serum and 50 μg/ml penicillin and streptomycin. Cells are initially seeded at $10^3$ cells/well, 0.1 ml/well. Cells are grown for 48 hrs without exposure to the anti-fungal, then medium is removed and varying dilutions of the antifungal prepared in complete medium are added to each well, with control wells receiving no antifungal. Cells are incubated for an additional 48–72 hrs. Medium is changed every 24 hrs and replaced with fresh medium containing the same concentration of the antifungal. Medium is then removed and replaced with complete medium without antifungal. Cells are incubated for 24 hr in the absence of antifungal compounds, then viability is estimated by the incorporation of $^{35}S$ into protein. Medium is removed, replaced with complete medium without methionine, and incubated for 30 min. Medium is again removed, and replaced with complet medium without methionine but containing 0.1 μCi/ml $^{35}S$ methionine. Cells are incubated for 3 hrs. Wells are washed 3 times in PBS, then cells are permeabilized by adding 100% methanol for 10 min. Ice cold 10% trichloroacetic acid (TCA) is added to fill wells; plates are incubated on ice for 5 min. This TCA wash is repeated two more times. Wells are again washed in methanol, then air dried. 50 μl of scintillation cocktail are added to each well and dried onto the wells by centrifugation. Plates are used to expose X ray film. Densitometer scanning of the autoradiogram, including wells without antifungal, is used to determine the dosage at which 50% of cells are not viable ($ID_{50}$) (Culture of Animal Cells. A manual of basic technique. (1987). R. Ian Freshney. John Wiley & Sons, Inc., New York).

16. Administration of Antimycotic Agents

The invention features a method for treating a subject infected with a mycotic organism by administering to that subject a therapeutically effective amount of an antimycotic agent able to selectively block translation of one or more fungal RNAs required for fungal growth. Such administration can be by any method known to those skilled in the art, for example, by topical application or by systemic administration. In addition, antimycotic agents of the present invention can be used to treat mycoticinfected items, such as wood, metal or plastic and the like, by methods such as, but not limited to, spraying or dusting of that agent onto the infected item, or impregnating that agent into the item. As discussed above, antimycotic agents of the present invention are also useful in general scientific assays well known to those of ordinary skill in the art.

By "therapeutically effective amount" is meant an amount that relieves (to some extent) one or more symptoms of the disease or condition in the patient. Additionally, by "therapeutically effective amount" is meant an amount that returns to normal, either partially or completely, physiological or biochemical parameters associated with or causative of a mycotic disease or condition. Generally, it is an amount between about 1 nmole and 1 µmole of the molecule, dependent on its $EC_{50}$ and on the age, size, and disease associated with the patient.

17. Antimycotic Afents Identified by Methods of the Invention

The invention features novel antifungal agents discovered by the methods described above. It also includes novel pharmaceutical compositions which include antifungal agents discovered as described above formulated in pharmaceutically acceptable formulations.

18. Packaged Kits

The invention also features the use of nucleic acid constructs containing fungal nucleic acid transcriptionally or translationally linked to a reporter-encoding sequence to discover antifungal agents, and kits for use of these constructs in antifungal agent screening methods.

Other embodiments are within the following claims.

What is claimed is:

1. A method for screening for an inhibitor of mycotic cell translation, comprising the steps of:

providing a mycotic cell system comprising a reporter gene transcriptionally linked to a sequence constructed and arranged to increase the level of transcription of said reporter gene, relative to overall transcription, when total translation in said system is reduced;

contacting said mycotic cell system with a potential inhibitor of mycotic cell translation; and measuring the level of synthesis of the gene product of said reporter gene, wherein an increased level of synthesis in the presence of said potential inhibitor compared to in the absence of said potential inhibitor is indicative of said inhibitor being an effective inhibitor of mycotic translation.

2. The method of claim 1 wherein said sequence comprises a promoter of a ribosomal protein-encoding gene or a promoter of a ribosomal RNA-encoding gene.

3. The method of claim 1, wherein said sequence comprises a promoter from an RPL16A-type gene.

4. The method of claim 1, further comprising contacting said mycotic cell system with an agent or putting said mycotic cell under a condition that causes limitation for an amino acid, with the effect of evoking a stringent response in said mycotic cell system.

5. The method of claim 4 wherein said agent is 3-amino-1,2,4-triazole.

6. The method of claim 1 wherein said cell system is a whole mycotic cell having a defective GCN-type gene.

7. The method of claim 1 wherein said reporter gene encodes an enzyme necessary for the growth of said mycotic cell.

8. The method of claim 7 wherein said defective GCN-type gene is gcn2.

9. The method of claim 7 wherein said defective GCN-type gene is gcn4.

10. The method of claim 7 wherein said reporter gene encodes an enzyme necessary for amino acid synthesis.

11. The method of claim 7, 8, 9, or 10 wherein said reporter gene is HIS3.

12. The method of claim 1, wherein a second reporter gene is transcriptionally linked to a second sequence which fails to cause an increase in the level of synthesis of the gene product of said second reporter gene in the presence of an inhibitor of translation in said cell system;

and said method further comprises measuring the level of synthesis of the gene product of said second reporter gene and comparing the level of synthesis of the gene product of said first and second reporter genes as a measure of the effectiveness of said potential inhibitor.

13. The method of claim 1 wherein the product of said reporter gene acts on a second reporter gene which encodes an enzyme detectable by an enzyme assay.

14. The method of claim 12 wherein said enzyme encoded by said second reporter gene is β-galactosidase.

15. A method for screening for an inhibitor of mycotic cell translation, comprising the steps of:

providing one or more isogenic mycotic cell systems each able to overexpress or underexpress a translation component, or to express a defective variant of said translation component; and measuring the growth or activity of each of said one or more mycotic cell systems in the presence of a potential inhibitor of mycotic cell translation, wherein differential growth or activity of said one or more mycotic cell systems is indicative of said potential inhibitor being an effective inhibitor of mycotic translation.

16. The method of claim 15 wherein said cell system is a whole mycotic cell.

17. The method of claim 15 wherein said cell system is an extract of a mycotic cell.

18. The method of claim 15 wherein said cell system is a Saccharomvces cerevisiae cell system.

19. The method of claim 15 wherein said translational component is a translational initiation factor.

20. The method of claim 15 wherein said translational component is a translational elongation factor.

21. The method of claim 15 wherein said translational component is a translational termination factor.

22. The method of claim 18 wherein said translational component is a gene product of a gene selected from the group consisting of YEF3, SUI3, GCD 11, SUI2 and GCN3.

23. The method of claim 15 further comprising the step of assaying for mRNA synthesis, processing and transport, and/or degradation.

24. A method for screening for a compound able to perturb mycotic cell translation, comprising the steps of:

providing a mycotic cell system comprising a gene encoding an mRNA having a first termination codon 5' of a second termination codon, wherein termination at said first termination codon produces a first-termination-codon protein which can be distinguished readily from a second-termination-codon protein produced by termination at said second termination codon;

contacting said cell system with a compound potentially able to perturb mycotic cell translation; and measuring the level of expression of said second-termination-codon protein, wherein an increased level of expression in the presence of said compound compared to in the absence of said compound is indicative of said compound being an effective compound for perturbation of mycotic cell translation.

25. The method of claim 24 wherein said second-termination-codon protein is an enzyme or provides a vital function for cell growth.

26. The method of claim 25 wherein said enzyme is a secreted enzyme.

27. The method of claim 26 wherein said secreted enzyme is the product of PHO5.

28. The method of claim 24 wherein said mycotic cell system is a fungal cell.

29. The method of claim 28 wherein said fungal cell is a S. cerevisiae cell.

30. Method for screening for a compound able to perturb mycotic cell translation, comprising the steps of:

providing a mycotic cell system comprising a gene encoding a protein, wherein said gene encodes mRNA having a translational-frameshift signal 5' of a termination codon, wherein translation according to said frameshift signal produces a first protein different from a second protein produced without frameshifting;

contacting said mycotic cell system with a compound potentially able to perturb mycotic cell translation; and measuring the level of expression of said first protein, wherein an increased or decreased level of expression in the presence of said compound compared to in the absence of said compound is indicative of said compound being an effective compound for perturbation of mycotic cell translation.

31. The method of claim 30 wherein said first protein and said second protein are measured.

32. The method of claim 30 or 31 wherein said second protein is an enzyme or provides a vital function for cell growth.

33. The method of claim 32 wherein said enzyme is a secreted enzyme.

34. The method of claim 33 wherein said secreted enzyme is the product of PHO5.

35. A method for screening for a compound which activates a kinase able to inhibit mycotic cell translation, comprising the steps of:

growing a mycotic cell system in a medium containing a toxic amino acid or purine analog and a compound potentially able to activate said kinase; and measuring the growth of said cell system, wherein increased growth is indicative of said compound being an effective inhibitor of mycotic cell translation.

36. The method of claim 35 wherein said kinase is a GCN2-type kinase.

37. The method of claim 35 wherein said toxic amino acid analog is 5-fluorotryptophan.

38. The method of claims 35, 36, or 37 wherein said compound acts by inhibiting a function that antagonizes said kinase.

39. The method of claim 38 wherein said function is a phosphatase.

40. The method of claim 38 wherein said function is a translation component that is normally inhibited by the kinase.

41. The method of claim 40 wherein said translation component is eIF-2 or eIF-2B.

42. The method of claim 38, 39, 40, or 41 wherein said cell system bears an allele of the mammalian GCN2-type kinase DAI.

43. Method for in vitro screening for an activator of a kinase required for mycotic cell growth, said activator being able to inhibit mycotic cell translation, comprising the steps of:

contacting said kinase with a potential activator of said kinase; and measuring activity of said kinase, wherein an increased activity of said kinase is indicative of said potential inhibitor being an effective inhibitor of mycotic cell translation.

44. The method of claim 43 wherein said kinase is a GCN2-type kinase.

45. A method for screening for a compound that inhibits a kinase, said kinase being required for mycotic cell growth at normal levels but being inhibitory for mycotic cell growth when constitutively activated, comprising the steps of:

growing a mycotic cell system having a constitutively activated allele of said kinase in a medium containing a potential inhibitor of said kinase; wherein said allele causes poor growth of said mycotic cell system compared to a normal allele; and measuring the growth or activity of said cell system, wherein an increased growth in the presence of said potential inhibitor is indicative of utility of said potential inhibitor as an inhibitor of mycotic cell growth.

46. The method of claim 45 wherein said cell system bears a constitutively activated allele of a GCN2-type gene.

47. The method of claim 45 wherein said cell system contains a reporter gene which is both positively regulated by a GCN2-type gene and produces a toxic, or conditionally toxic, product.

48. The method of claim 47 wherein said reporter gene encodes galactokinase.

49. The method of claims 45, 46, 47 or 48 wherein said compound acts by activating a function that antagonizes said kinase.

50. The method of claim 49 wherein said function is a phosphatase.

51. The method of claim 49 wherein said function is a translation component that is normally inhibited by the kinase.

52. The method of claim 51 wherein said translation component is eIF-2 or eIF-2B.

53. The method of claims 49, 50, 51, or 52 wherein said cell system bears an allele of the mammalian GCN2-type kinase DAI.

54. The method of claim 49 wherein said cell system bears an allele of the mammalian GCN2-type kinase DAI.

55. Method for in vitro screening for an inhibitor of a kinase required for mycotic cell growth, said inhibitor being able to inhibit mycotic cell translation, comprising the steps of:

contacting said kinase with a potential inhibitor of said kinase; and measuring activity of said kinase, wherein a decreased activity of said kinase is indicative of said potential inhibitor being an effective inhibitor of mycotic cell translation.

56. The method of claim 55 wherein said kinase is a GCN2-type kinase.

57. A method for screening for an inhibitor of mycotic cell translation, comprising the steps of:
- identifying two components of a mycotic cell translational system which interact,
- providing a polypeptide, or derivative or analog thereof which mimics one portion of one said component,
- growing a mycotic cell system in a medium containing said polypeptide, derivative, or analog; and
- measuring the growth of said cell system, wherein a decreased growth is indicative of said polypeptide, derivative, or analog tbeing an effective inhibitor of mycotic cell translation.

58. The method of claim 57 wherein said polypeptide is the gene product of a dominant negative allele of a translational component.

59. The method of claim 57 wherein said polypeptide is a portion of the gene product of a dominant negative allele of a translational component.

60. The method of claim 58 or 59 wherein said polypeptide is chemically modified.

61. A Method for screening for a dominant negative allele of a translational component, comprising the steps of:
- mutagenizing a gene encoding said translational component;
- placing the mutagenized gene under the control of an inducible promoter in a vector;
- introducing said vector into a mycotic cell system; and
- measuring inhibition of growth of said mycotic cell system under conditions which induce expression of said promoter, wherein a decreased growth is indicative of the gene product of said mutagenized gene being an effective inhibitor of mycotic cell translation.

62. The method of claim 61 wherein said gene encoding a translational component is a portion of a gene encoding a translational component.

63. A method for screening for an inhibitor of mycotic cell translation, comprising the steps of:
- providing one translational component fused to a first heterologous domain;
- providing another translational component fused to a second heterologous domain; wherein said first and second heterologous domains interact to provide a signal when brought together by interaction of said one component and said other component, and
- measuring the level of said signal in the presence of a potential inhibitor of mycotic cell translation, wherein a reduced signal is indicative of said translational components being useful inhibitors of mycotic cell translation.

64. The method of claim 63 wherein said translational components are two proteins.

65. The method of claim 63 wherein said translational components are two domains of a protein.

66. The method of claim 63 wherein said translational components are portions of two translational proteins.

67. The method of claim 63 wherein said translational components are portions of two domains of a translation protein.

68. The method of claim 63, 64, 65, 66, or 67 wherein said translational components are chemically modified.

69. The method of claim 63 wherein said first heterologous domain is a GAL4 DNA-binding domain, and said second heterologous domain is a GAL4 transcription-activation domain, and said measuring comprises measuring said signal as an indication of transcription activation as an indication of the strength of interaction between said translational components.

70. The method of claim 63, 64, 65, 66, 67, 68, or 69 wherein said translational components are mycotic translational components.

71. A Method for screening for an inhibitor of mycotic mitochondrial translation, comprising the steps of:
- growing a mycotic cell system in a medium containing an inhibitor of mycotic cytoplasmic translation and a potential inhibitor of mycotic mitochondrial translation; and
- measuring protein synthesis, wherein a decrease in protein synthesis is indicative of said potential inhibitor being an effective inhibitor of mycotic mitochondrial translation.

72. The method of claim 71 wherein said inhibitor of mycotic cytoplasmic translation is cycloheximide.

* * * * *